(12) United States Patent
Mrsny

(10) Patent No.: US 7,611,714 B2
(45) Date of Patent: Nov. 3, 2009

(54) METHODS AND COMPOSITIONS FOR IMMUNIZING AGAINST PSEUDOMONAS INFECTION

(75) Inventor: Randall J. Mrsny, Los Altos Hills, CA (US)

(73) Assignee: Trinity Biosystems, Inc., Menlo Park, CA (US)

( * ) Notice: Subject to any disclaimer, the term of this patent is extended or adjusted under 35 U.S.C. 154(b) by 324 days.

(21) Appl. No.: 11/244,348

(22) Filed: Oct. 4, 2005

(65) Prior Publication Data

US 2006/0104993 A1    May 18, 2006

Related U.S. Application Data

(60) Provisional application No. 60/616,125, filed on Oct. 4, 2004.

(51) Int. Cl.
   *A61K 39/02* (2006.01)
   *G01N 33/53* (2006.01)

(52) U.S. Cl. .................................. 424/190.1; 435/7.1

(58) Field of Classification Search ............... 424/190.1
   See application file for complete search history.

(56) References Cited

U.S. PATENT DOCUMENTS

| | | | |
|---|---|---|---|
| 4,892,827 A | 1/1990 | Pastan et al. | |
| 5,082,927 A | 1/1992 | Pastan et al. | |
| 5,223,604 A | 6/1993 | Hodges et al. | |
| 5,328,984 A | 7/1994 | Pastan et al. | |
| 5,445,818 A | 8/1995 | Hodges et al. | |
| 5,458,878 A | 10/1995 | Pastan et al. | |
| 5,468,484 A | 11/1995 | Hodges et al. | |
| 5,494,672 A | 2/1996 | Hodges et al. | |
| 5,512,658 A | 4/1996 | Pastan et al. | |
| 5,573,916 A | 11/1996 | Cheronis et al. | |
| 5,602,095 A | 2/1997 | Pastan et al. | |
| 5,612,036 A | 3/1997 | Hodges et al. | |
| 5,696,237 A | 12/1997 | Fitzgerald et al. | |
| 5,705,156 A | 1/1998 | Pastan et al. | |
| 5,705,163 A | 1/1998 | Pastan et al. | |
| 5,854,044 A | 12/1998 | Pastan et al. | |
| 5,863,745 A | 1/1999 | Fitzgerald et al. | |
| 5,965,406 A | 10/1999 | Murphy | |
| 5,980,895 A | 11/1999 | Pastan et al. | |
| 6,011,002 A | 1/2000 | Pastan et al. | |
| 6,022,950 A | 2/2000 | Murphy | |
| 6,074,644 A | 6/2000 | Pastan et al. | |
| 6,086,900 A | 7/2000 | Draper | |
| 6,423,513 B1 | 7/2002 | Fitzgerald et al. | |
| 6,426,075 B1 | 7/2002 | Fitzgerald et al. | |
| 6,498,233 B1 | 12/2002 | Weis et al. | |
| 7,314,632 B1 * | 1/2008 | Fitzgerald | 424/236.1 |
| 2002/0106370 A1 | 8/2002 | Cardy et al. | |
| 2003/0054012 A1 | 3/2003 | Fitzgerald et al. | |
| 2004/0071731 A1 | 4/2004 | Fitzgerald | |
| 2005/0079171 A1 | 4/2005 | Fitzgerald et al. | |
| 2006/0153798 A1 | 7/2006 | Mrsny | |
| 2007/0003578 A1 | 1/2007 | Fitzgerald | |
| 2007/0141070 A1 | 6/2007 | Mrsny | |
| 2007/0148131 A1 | 6/2007 | Mrsny | |

FOREIGN PATENT DOCUMENTS

| | | |
|---|---|---|
| EP | 0439954 | 8/1991 |
| WO | WO90/13563 | 11/1990 |
| WO | WO93/11791 | 6/1993 |
| WO | WO95/31483 | 11/1995 |
| WO | WO97/13529 | 4/1997 |
| WO | WO98/20135 | 5/1998 |
| WO | WO99/02712 | 1/1999 |
| WO | WO99/57142 | 11/1999 |

OTHER PUBLICATIONS

Sastry et al. (FEBS Letters, vol. 151, No. 2, 1983).*
sequence alignment AC PO2973;Q53390.*
Sastry et al. FEBS Letters, vol. 151, No. 2, 1983.*
sequence alignment AC PO2973;Q53390. Nov. 1990.*
U.S. Appl. No. 09/462,682, filed Apr. 28, 2000, Fitzgerald et al.
U.S. Appl. No. 10/110,880, filed Apr. 16, 2002, Fitzgerald et al.
Ashorn, P. et al., "Elimination of infectious human immunodeficiency virus from human T-cell cultures by synergistic action of CD4-Pseudomonas exotoxin and reverse transcriptase inhibitors" PNAS USA 87:8889-8893 (1990).
Benhar, I. et al., "Pseudomonas Exotoxin A Mutants: Replacement of surface-exposed residues in domain III with cysteine residues that can be modified with polyethylene glycol in a site-specific manner" J. Biol. Chem. 269(18):13398-13404 (1994).
Berger, E. et al., "CD4-Pseudomonas exotoxin hybrid protein blocks the spread of human immunodeficiency virus infection in vitro and is active against cells expressing the envelope glycoproteins from diverse primate immunodeficiency retroviruses" PNAS USA 86:9539-9543 (1989).

(Continued)

*Primary Examiner*—Robert B. Mondesi
*Assistant Examiner*—Khatol Shahnan-Shah
(74) *Attorney, Agent, or Firm*—Jones Day

(57) ABSTRACT

Methods and compositions for inducing an immune response against *Pseudomonas aeruginosa* are provided herein. In one aspect, the invention provides a chimeric immunogen, comprising a receptor binding domain, a translocation domain, and a *Pseudomonas* pilin peptide comprising an amino acid sequence that is TAADGLWKCTSDQDEQFIPKGCSK (SEQ ID NO.:1), wherein the chimeric immunogen, when administered to a subject, induces an immune response in said subject that is effective to reduce adherence of a microorganism that expresses said *Pseudomonas* pilin peptide to epithelial cells of said subject. In other aspects, the invention provides nucleic acids encoding chimeric immunogens of the invention, kits comprising chimeric immunogens of the invention, cells expressing chimeric immunogens of the invention, and methods of using chimeric immunogens of the invention.

22 Claims, 13 Drawing Sheets

OTHER PUBLICATIONS

Figure 2:
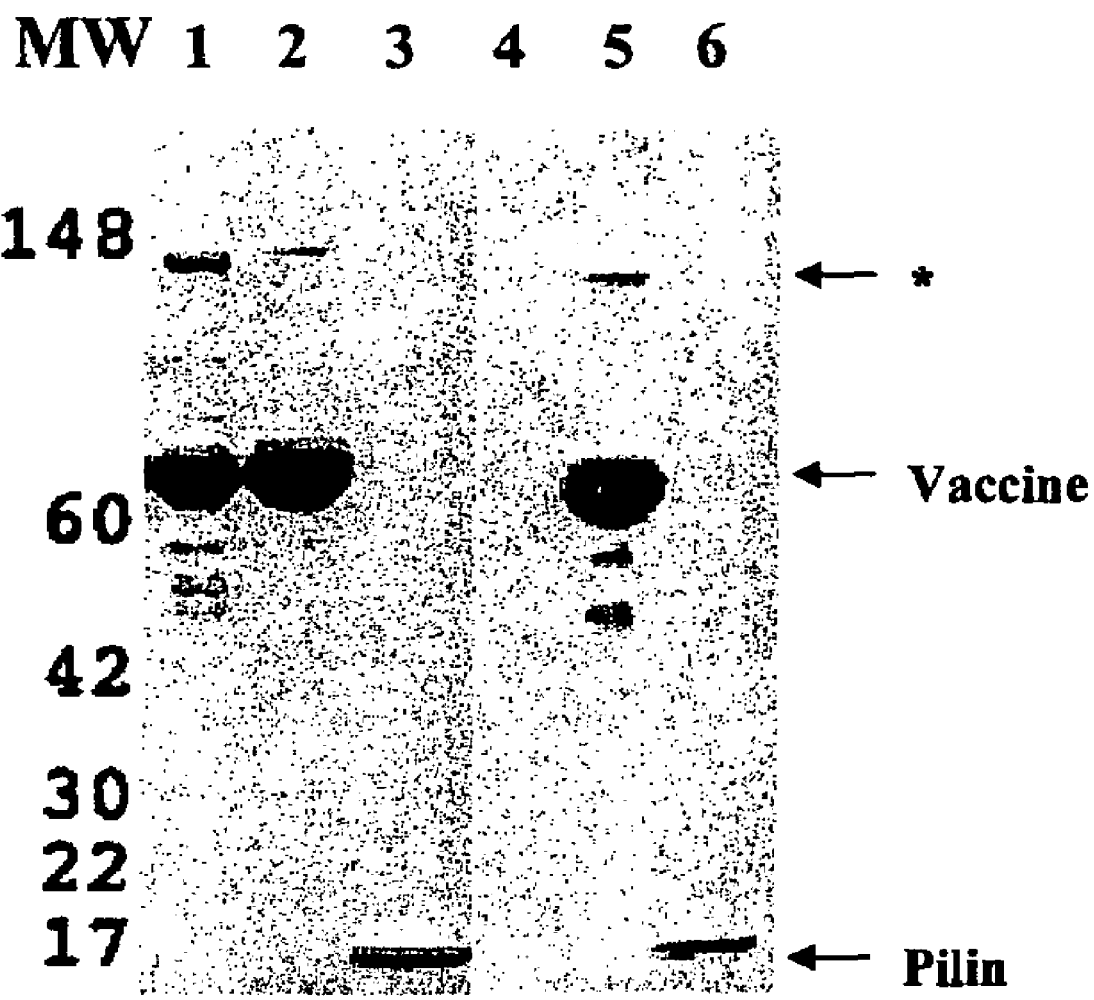

Brinkmann, U. et al., "Alteration of a protease-sensitive region of Pseudomonas exotoxin prolongs its survival in the circulation of mice" PNAS USA 89:3065-3069 (1992).

Brinkmann, U. et al., "Independent domain folding of Pseudomonas exotoxin and single-chain immunotoxins: Influence of interdomain connections" PNAS USA 89:3075-3079 (1992).

Brinkmann, U. et al., "Immunotoxins against cancer" Biochimica et Biophysica Acta 1198:27-45 (1994).

Chaudhary, V. et al., "Selective killing of HIV-infected cells by recombinant human CD4-Pseudomonas exotoxin hybrid protein" Nature 335:369-372 (1988).

Chaudhary, V. et al., "Pseudomonas exotoxin contains a specific sequence at the carboxyl terminus that is required for cytotoxicity" PNAS USA 87:308-312 (1990).

Chandhary, V. et al., "Mutagenesis of Pseudomonas exotoxin in identification of sequences responsible for the animal toxicity" J. Biol. Chem. 265(27):16303-16310 (1990).

Choe, M. et al., "B3(Fab)-PE38$^M$: A recombinant immunotoxin in which a mutant form of Pseudomonas exotoxin is fused to the Fab fragment of monoclonal antibody B3" Cancer Res. 54:3460-3467 (1994).

Cryz, Jr., S. et al., "Safety and immunogenicity of a Pseudomonas aeruginosa O-polysaccharide toxin A conjugate vaccine in humans" J. Clin. Invest. 80:51-56 (1987).

Cryz, Jr., S. et al., "Safety and immunogenicity of *Escherichia coli* O18 O-specific polysaccharide (O-PS)-toxin A and O-PS-cholera toxin conjugate vaccines in humans" J. Infect. Dis. 163:1040-1045 (1991).

Cryz, Jr., S. et al., "Human immunodeficiency virus-1 principal neutralizing domain peptide-toxin A conjugate vaccine" Vaccine 13(1):67-71 (1995).

Fattom, A. et al., "Comparative immunogenicity of conjugates composed of the Staphylococcus aureus type 8 capsular polysaccharide bound to carrier proteins by adipic acid dihydrazide or N-Succinimidyl-3-(2-pridyldithio)propionate" Infection and Immunity 60(2):584-589 (1992).

Fattom, A. et al., "Laboratory and clinical evaluation of conjugate vaccines composed of Staphylococcus aureus type 5 and type 8 capsular polysaccharides bound to Pseudomonas aeruginosa recombinant exoprotein A" Infection and Immunity 61(3):1023-1032 (1993).

Fitzgerald, D.J. et al., "Characterization of V3 loop-Pseudonomas exotoxin chimeras. Candidate vaccines for human immunodeficiency virus-1." J. Biol. Chem., vol. 273, No. 16; pp. 9951-9958 (1998).

Hahn, H. et al., "Pilin-Based Anti-Pseudomonas Vaccines: Latest Developments and Perspectives" Behring Institute: Mitteilungen, Marburg, DE 98:315-325 (1997).

Hertle, R. et al., "Dual-Function Vaccine for Pseudomonas Aeruginosa: Characterization of Chimeric Exotoxin A-Pilin Protein" Infection and Immunity 69(11):6962-6969 (2001).

Jinno, Y. et al., "Domain II mutants of Pseudomonas exotoxin deficient in translocation" J. Biol. Chem. 264(27):15953-15959 (1989).

Johnson, K. et al., "Nucleotide sequence and transcriptional initiation site of two Pseudomonas aeruginosa pilin genes" J. Biol. Chem. 261(33):15703-15708 (1986).

Kasturi, S. et al., "Alanine scanning mutagenesis identifies surface amino acids on domain III of Pseudomonas exotoxin required for cytotoxicity, proper folding, and secretion into periplasm" J. Biol. Chem. 267(32):23427-23433 (1992).

Kondo, T. et al., "Activity of immunotoxins constructed with modified Pseudomona exotoxin A lacking the cell recognition domain" J. Biol. Chem. 263(19):9470-9475 (1988).

Kreitman, R. et al., "Properties of chimeric toxins with two recognition domains: Interleukin 6 and transofrming growth factor α at different locations in Pseudomonas exotoxin" Biocon. Chem 3:63:68 (1992).

Kuan, C. et al., "Pseudomonas exotoxin A mutants: Replacement of surface exposed residues in domain II with cysteine residues that can be modified with polyethylene glycol in a site-specific manner" J. Biol. Chem. 269(10):7610-7616 (1994).

Kuan, C. et al., "Improved antitumor activity of a recombinant anti-Lewis$^y$immunotoxin not requiring proteolytic activation" PNAS USA 93:974-978 (1996).

Lukac, M et al., "Toxoid of Pseudomonas aeruginosa Exotoxin A Generated by Deletion of an Active-Site Residue" Infection and Immunity 56(12):3095-3098 (1988).

Mansfield, E. et al., "Characterization of RFB4-Pseudomonas exotoxin A immunotoxins targeted to CD22 on B-cell malignancies" Bioconj. Chem. 7:557-563 (1996).

Ogata, M. et al., "Processing of Pseudomonas exotoxin by a cellular protease results in the generation of a 37,000-da toxin fragment that is translocated to the cytosol" J. Biol. Chem. 265(33):20678-20685 (1990).

Ogata, M. et al., "Cell-mediated cleavage of Pseudomonas exotoxin between Arg$^{279}$ and Gly$^{280}$ generates the enzymatically active fragment which translocates to the cytosol" J. Biol. Chem. 267(35):25396-25401 (1992).

Pastan, I. et al., "Pseudomonas exotoxin: chimeric toxins" J. Biol. Chem. 264(26):15157-15160 (1989).

Que, J. et al., "Effect of carrier selection on immunogenicity of protein conjugate vaccines against Plasmodium falciparum circumsporozoites" Infect. and Immun. 56(10):2645-2649 (1988).

Reiter, Y. et al., "Engineering antibody Fv fragments fro cancer detection and therapy: disulfide-stabilized Fv fragments" Nature Biotech. 14:1239-1245 (1996).

Seetharam, S. et al., "Increased cytotoxic activity of Pseudomonas exotoxin and two chimeric toxins ending in KDEL" J. Biol. Chem. 266(26):17376-17381 (1991).

Siegall, C. et al., "Functional analysis of domains II, Ib, and III of Pseudomonas exotoxin" J. Biol. Chem. 264(24):14256-14261 (1989).

Siegall, C. et al., "Analysis of sequences in domain II of Pseudomonas exotoxin A which mediate translocation" Biochemistry 30:7154-7159 (1991).

Theuer, C. et al., "A recombinant form of Pseudomonas exotoxin directed at the epidermal growth factor receptor that is cytotoxicwithout requiring proteolytic processing" J. Biol. Chem. 267(24):16872-16877 (1992).

Theuer, C. et al., "Immunotoxins made with a recombinant form of Pseudomonas exotoxin A that do not require proteolysis for activity" Cancer Res. 53:340-347 (1993).

Wall, D. and Kaiser, D., "Type IV Pili and Cell Motility." Mol. Microbiol. 32(1):1-10 (1999).

Zdanovsky, A. et al., "Mechanism of action of Pseudomonas exotoxin" J. Biol. Chem. 268(29):21791-21799 (1993).

U.S. Appl. No. 09/462,682, filed Apr. 28, 2000, Fitzgerald.

U.S. Appl. No. 11/664,786, filed Apr. 3, 2007, Mrsny.

U.S. Appl. No. 11/664,787, filed Apr. 3, 2007, Mrsny.

U.S.P.T.O. Declaration of Randall Thomas Irvin, Under Rule 1.132, dated Aug. 23, 1993, in U.S. Appl. No. 07/927,797, filed Aug. 10, 1992.

ISA PCT International Search Report dated, Oct. 1, 2008, for International Application No. PCT/US2005/035802, filed Oct. 4, 2005.

AC P02973; Q53390, Jul. 21, 1986.

Johnson et al., 1986 . "Nucleotide Sequence and Transcriptional Initiation Site of Two Pseudomonas Aeruginosa Pilin Genes," The Journal of Biological Chemistry, vol. 261(33):15703-15708.

Lee et al., 1989, "Immunological Studies of the Disulfide Bridge Region of Pseudomonas Aeruginosa PAK and PAO Pilins, Using Anti-PAK Pilus and Antipeptide Antibodies," Infection and Immunity, vol. 57(2):520-526.

Paranchych et al., 1985, "Pseudomonas Pili Studies on Antigenic Determinants and Mammallian Cell Receptors," Antibiot. Chemother., vol. 36:49-57.

Paranchych et al., 1979, "Biochemical Studies on Pili Isolated from Pseudomonas Aeruginosa Strain PAO," Can. J. Microbiol., vol. 25:1175-1181.

Paranchych et al., 1986, "Fimbriae (PILI): Molecular Basis of Pseudomonas Aeruginosa Adherence," Clinical and Investigative Medicine, vol. 9(2):113-118.

Sastry et al., 1984, "Studies on the Primary Structure and Antigenic Determinants of Pilin Isolated from Pseudomonas Aeruginosa K," Can. J. Biochem. Cell Biol., vol. 63:284-291.

Sastry et al., 1985, "Comparative Studies of the Amino Acid and Nucleotide Sequences of Pilin Derived from Pseudomonas Aeruginosa PAK and PAO," Journal of Bacteriology, vol. 164(2):571-577.

Watts et al., 1983, "Mapping of the Antigenic Determinants of Pseudomonas Aeruginosa PAK Polar Pili,". Infection and Immunity, vol. 42(1):113-121.

* cited by examiner

Figure 1 ntPE

Ib loop
S-S

Vaccine

Pilin loop
S-S

360 AGAANADVVSLTCPVAAGECAG      Native ntPE Ib loop
360 ATSTAADGLWKCTSDQDEQFIPKGCSKQG   Inserted pilin loop

Figure 4
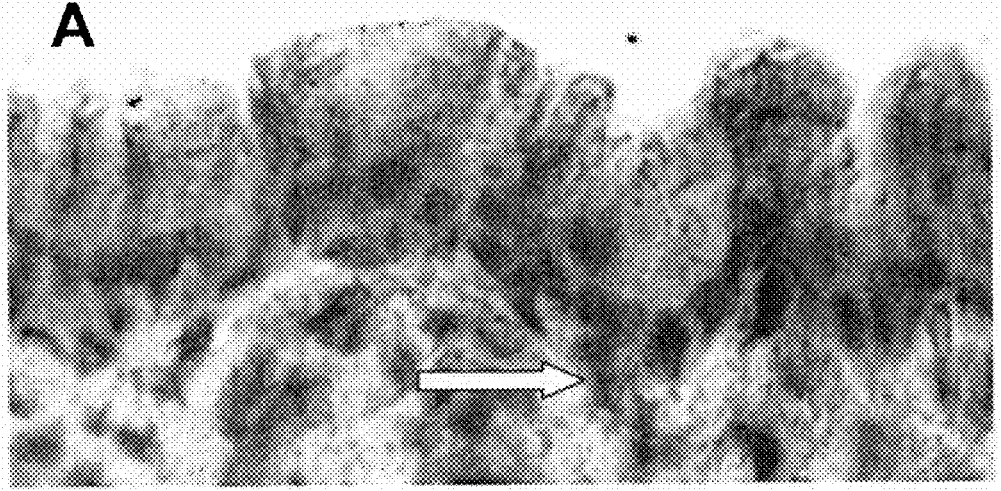
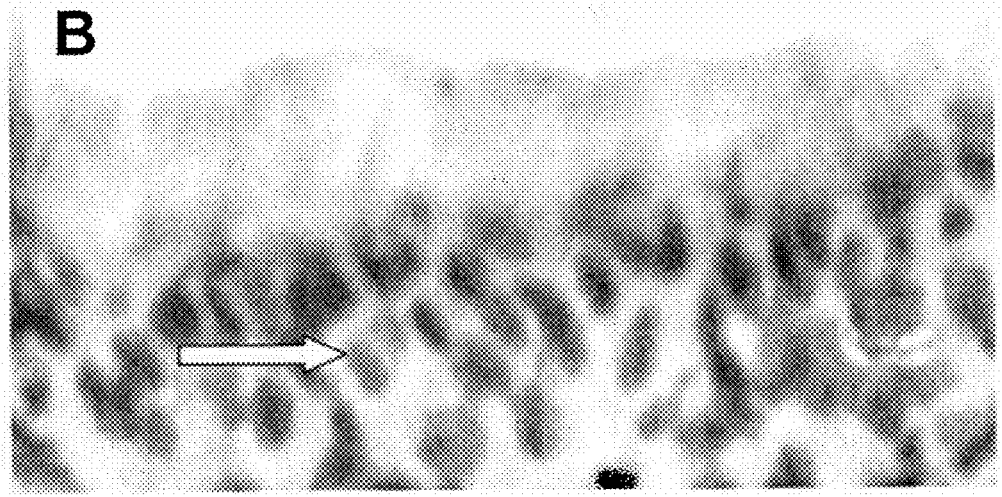
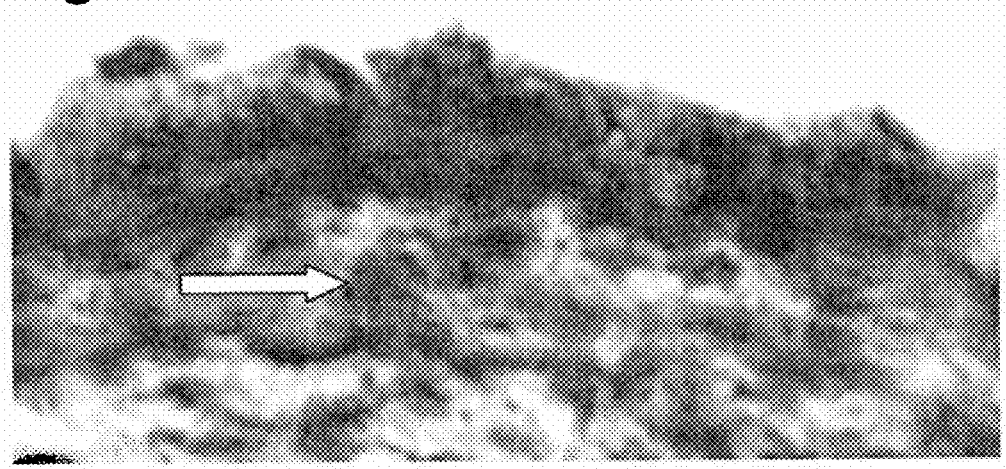
Arrows identify phagocyte-like cells in nasal subepithelium

Figure 5
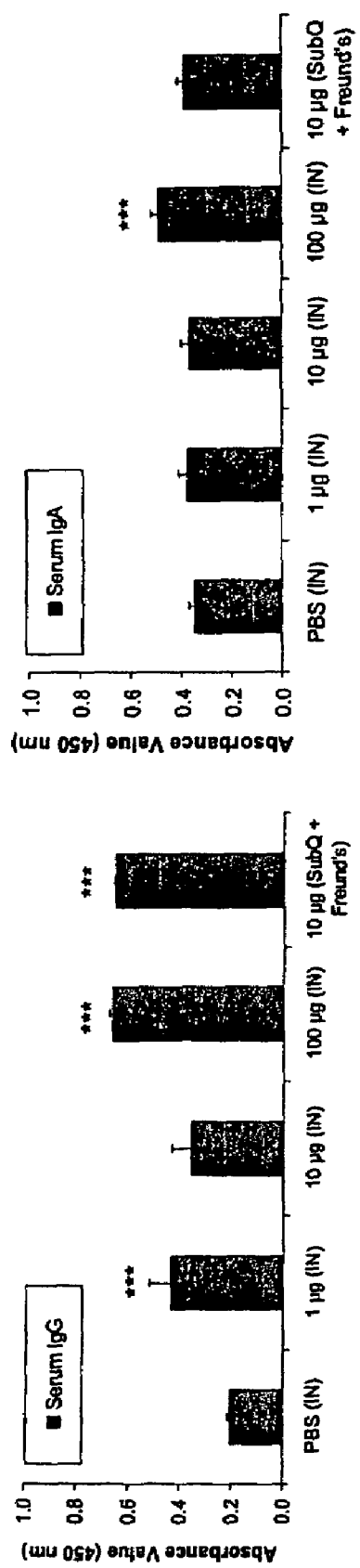
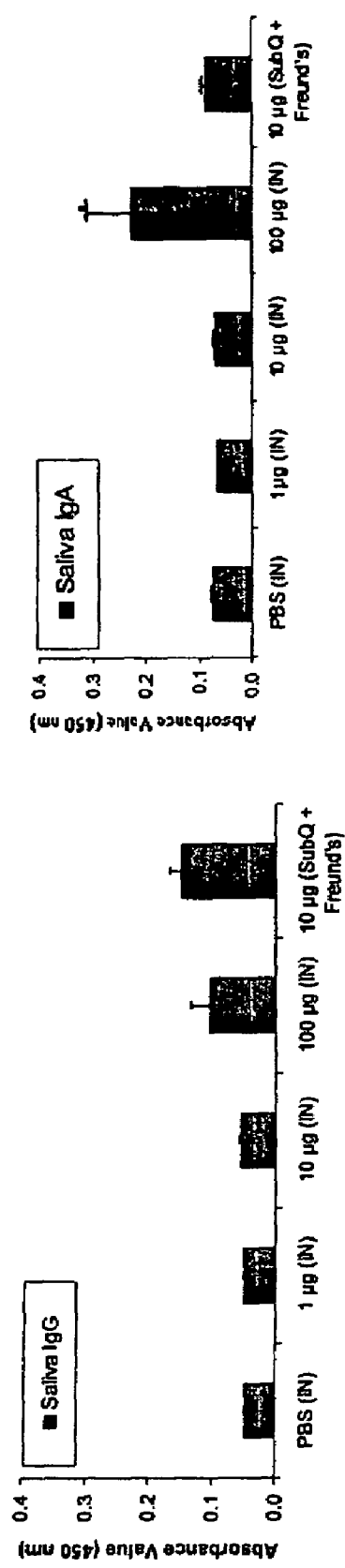

Figure 7
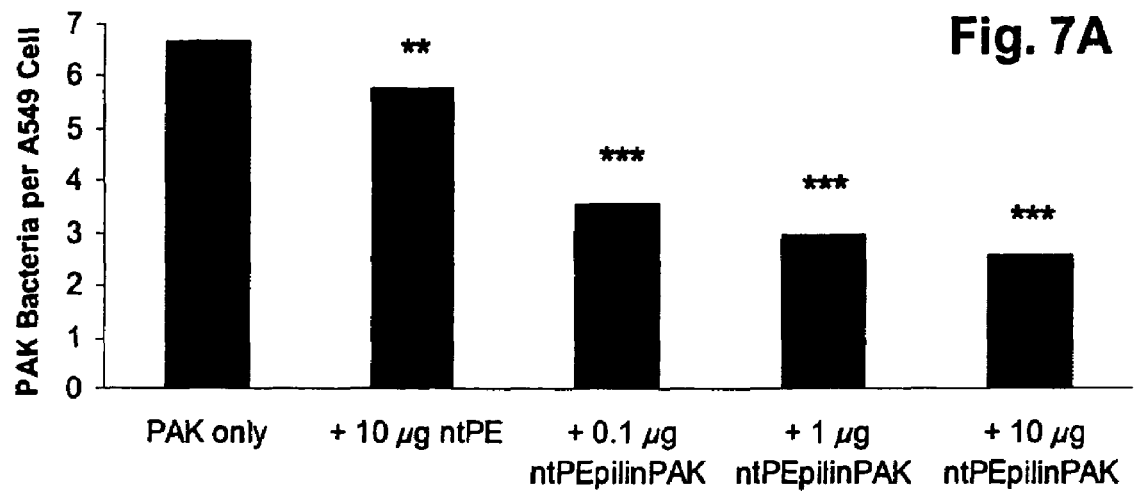
Fig. 7A
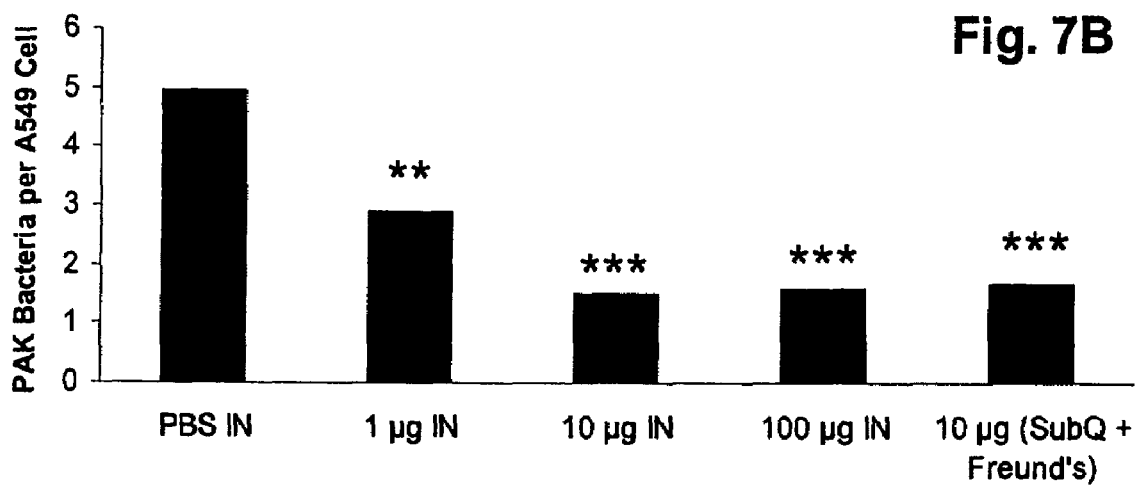
Fig. 7B
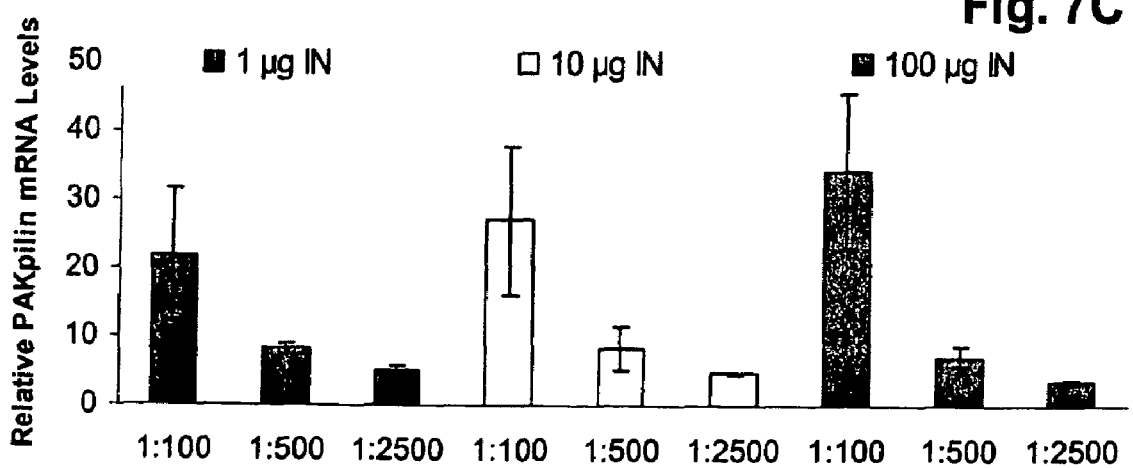
Fig. 7C

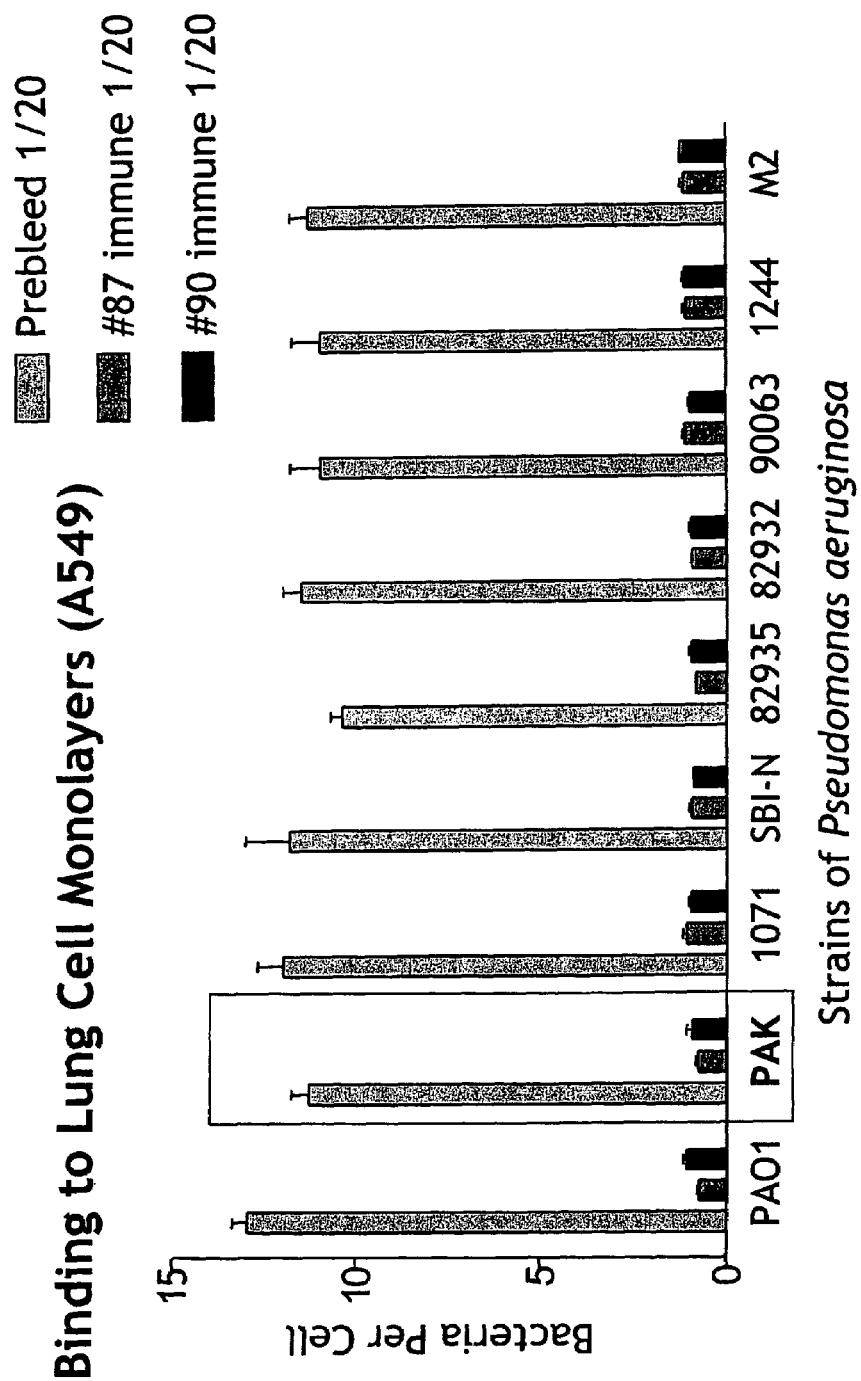

Figure 13

Pseudomonas Aeruginosa Exotoxin A Amino Acid Sequence (SEQ ID NO.:13)

```
  1 mhliphwipl vaslgllagg ssasa aeeaf dlwnecakac vldlkdgvrs srmsvdpaia 61 dtngqgvlhy smvleggnda lklaidnals itsdgltirl eggvepnkpv rysytrqarg 121 swslnwlvpi ghekpsnikv fihelnagnq lshmspiyti emgdellakl ardatffvra 181 hesnemqptl aishagvsvv maqtqprrek rwsewasgkv lclldpldgv ynylaqqrcn
```

Start of Domain II↓
```
241 lddtwegkiy rvlagnpakh dldikptvis hrlhfpeggs laaltahqac hlpletftrh
```

⇓Furin clip site
```
301 rqprgweqle qcgypvqrlv alylaarlsw nqvdqvirna laspgsggdl geaireqpeq
```
                                Start of Domain III↓
```
361 arlaltlaaa eserfvrqgt gndeagaana dvvsltcpva agecagpads gdallernyp 421 tgaeflgdgg dvsfstrgtq nwtverllqa hrqleergyv fvgyhgtfle aaqsivfggv 481 rarsqdldai wrgfyiagdp alaygyaqdq epdargrirn gallrvyvpr sslpgfyrts 541 ltlaapeaag evErlighpl plrldaitgp eeeggrleti lgwplaertv vipsaiptdp 601 rnvggdldps sipdkeqais alpdyasqpg kppredlk
```

SEQUENCE LISTING

<160> NUMBER OF SEQ ID NOS: 12

<210> SEQ ID NO 1
<211> LENGTH: 24
<212> TYPE: PRT
<213> ORGANISM: Pseudomonas sp.

<400> SEQUENCE: 1

```
Thr Ala Ala Asp Gly Leu Trp Lys Cys Thr Ser Asp Gln Asp Glu Gln
1               5                   10                  15

Phe Ile Pro Lys Gly Cys Ser Lys
            20
```

<210> SEQ ID NO 2
<211> LENGTH: 4
<212> TYPE: PRT
<213> ORGANISM: Pseudomonas sp.

<400> SEQUENCE: 2

```
Arg Asp Glu Leu
1
```

<210> SEQ ID NO 3
<211> LENGTH: 4
<212> TYPE: PRT
<213> ORGANISM: Pseudomonas sp.

<400> SEQUENCE: 3

```
Lys Asp Glu Leu
1
```

<210> SEQ ID NO 4
<211> LENGTH: 266
<212> TYPE: PRT
<213> ORGANISM: Pseudomonas sp.

<400> SEQUENCE: 4

```
Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60

Gln Gly Val Leu His Tyr Ser Met Val Leu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
```

```
                225                 230                 235                 240
Leu Asp Asp Thr Trp Glu Gly Lys Ile Tyr Arg Val Leu Ala Gly Asn
                    245                 250                 255

Pro Ala Lys His Asp Leu Asp Ile Lys Pro
                260                 265

<210> SEQ ID NO 5
<211> LENGTH: 644
<212> TYPE: PRT
<213> ORGANISM: Pseudomonas sp.

<400> SEQUENCE: 5

Met His Leu Ile Pro His Trp Ile Pro Leu Val Ala Ser Leu Gly Leu
  1               5                  10                  15

Leu Ala Gly Gly Ser Ser Ala Ser Ala Glu Glu Ala Phe Asp Leu
                 20                  25                  30

Trp Asn Glu Cys Ala Lys Ala Cys Val Leu Asp Leu Lys Asp Gly Val
             35                  40                  45

Arg Ser Ser Arg Met Ser Val Asp Pro Ala Ile Ala Asp Thr Asn Gly
         50                  55                  60

Gln Gly Val Leu His Tyr Ser Met Val Leu Glu Gly Asn Asp Ala
 65                  70                  75                  80

Leu Lys Leu Ala Ile Asp Asn Ala Leu Ser Ile Thr Ser Asp Gly Leu
                 85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
                260                 265                 270

Leu His Phe Pro Glu Gly Gly Ser Leu Ala Ala Leu Thr Ala His Gln
            275                 280                 285

Ala Cys His Leu Pro Leu Glu Thr Phe Thr Arg His Arg Gln Pro Arg
        290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335
```

```
Ile Arg Asn Ala Leu Ala Ser Pro Gly Ser Gly Gly Asp Leu Gly Glu
                340                 345                 350

Ala Ile Arg Glu Gln Pro Glu Gln Ala Arg Leu Ala Leu Thr Leu Ala
            355                 360                 365

Ala Ala Glu Ser Glu Arg Phe Val Arg Gln Gly Thr Gly Asn Asp Glu
        370                 375                 380

Ala Thr Ser Thr Ala Ala Asp Gly Leu Trp Lys Cys Thr Ser Asp Gln
385                 390                 395                 400

Asp Glu Gln Phe Ile Pro Lys Gly Cys Ser Lys Gln Gly Pro Ala Asp
                405                 410                 415

Ser Gly Asp Ala Leu Leu Glu Arg Asn Tyr Pro Thr Gly Ala Glu Phe
            420                 425                 430

Leu Gly Asp Gly Gly Asp Val Ser Phe Ser Thr Arg Gly Thr Gln Asn
        435                 440                 445

Trp Thr Val Glu Arg Leu Leu Gln Ala His Arg Gln Leu Glu Glu Arg
    450                 455                 460

Gly Tyr Val Phe Val Gly Tyr His Gly Thr Phe Leu Glu Ala Ala Gln
465                 470                 475                 480

Ser Ile Val Phe Gly Val Arg Ala Arg Ser Gln Asp Leu Asp Ala
                485                 490                 495

Ile Trp Arg Gly Phe Tyr Ile Ala Gly Asp Pro Ala Leu Ala Tyr Gly
            500                 505                 510

Tyr Ala Gln Asp Gln Glu Pro Asp Ala Arg Gly Arg Ile Arg Asn Gly
        515                 520                 525

Ala Leu Leu Arg Val Tyr Val Pro Arg Ser Ser Leu Pro Gly Phe Tyr
    530                 535                 540

Arg Thr Ser Leu Thr Leu Ala Ala Pro Glu Ala Ala Gly Glu Val Arg
545                 550                 555                 560

Leu Ile Gly His Pro Leu Pro Leu Arg Leu Asp Ala Ile Thr Gly Pro
                565                 570                 575

Glu Glu Glu Gly Gly Arg Leu Glu Thr Ile Leu Gly Trp Pro Leu Ala
            580                 585                 590

Glu Arg Thr Val Val Ile Pro Ser Ala Ile Pro Thr Asp Pro Arg Asn
        595                 600                 605

Val Gly Gly Asp Leu Asp Pro Ser Ser Ile Pro Asp Lys Glu Gln Ala
    610                 615                 620

Ile Ser Ala Leu Pro Asp Tyr Ala Ser Gln Pro Gly Lys Pro Pro Arg
625                 630                 635                 640

Glu Asp Leu Lys

<210> SEQ ID NO 6
<211> LENGTH: 153
<212> TYPE: PRT
<213> ORGANISM: Pseudomonas sp.

<400> SEQUENCE: 6

Thr Val Ile Ser His Arg Leu His Phe Pro Glu Gly Gly Ser Leu Ala
1               5                   10                  15

Ala Leu Thr Ala His Gln Ala Cys His Leu Pro Leu Glu Thr Phe Thr
            20                  25                  30

Arg His Arg Gln Pro Arg Gly Trp Glu Gln Leu Glu Gln Cys Gly Tyr
        35                  40                  45

Pro Val Gln Arg Leu Val Ala Leu Tyr Leu Ala Ala Arg Leu Ser Trp
    50                  55                  60
```

```
Asn Gln Val Asp Gln Val Ile Arg Asn Ala Leu Ala Ser Pro Gly Ser
 65                  70                  75                  80

Gly Gly Asp Leu Gly Glu Ala Ile Arg Glu Gln Pro Glu Gln Ala Arg
             85                  90                  95

Leu Ala Leu Thr Leu Ala Ala Ala Glu Ser Glu Arg Phe Val Arg Gln
            100                 105                 110

Gly Thr Gly Asn Asp Glu Ala Gly Ala Ala Asn Ala Asp Val Val Ser
        115                 120                 125

Leu Thr Cys Pro Val Ala Ala Gly Glu Cys Ala Gly Pro Ala Asp Ser
    130                 135                 140

Gly Asp Ala Leu Leu Glu Arg Asn Tyr
145                 150

<210> SEQ ID NO 7
<211> LENGTH: 17
<212> TYPE: PRT
<213> ORGANISM: Pseudomonas sp.

<400> SEQUENCE: 7

Lys Cys Thr Ser Asp Gln Asp Glu Gln Phe Ile Pro Lys Gly Cys Ser
 1               5                  10                  15

Lys

<210> SEQ ID NO 8
<211> LENGTH: 5
<212> TYPE: PRT
<213> ORGANISM: Pseudomonas sp.

<400> SEQUENCE: 8

Arg Asp Glu Leu Lys
 1               5

<210> SEQ ID NO 9
<211> LENGTH: 1839
<212> TYPE: DNA
<213> ORGANISM: Pseudomonas sp.

<400> SEQUENCE: 9
gccgaagaag ctttcgacct ctggaacgaa tgcgccaaag cctgcgtgct cgacctcaag      60
gacggcgtgc gttccagccg catgagcgtc gacccggcca tcgccgacac caacggccag     120
ggcgtgctgc actactccat ggtcctggag ggcggcaacg acgcgctcaa gctggccatc     180
gacaacgccc tcagcatcac cagcgacggc ctgaccatcc gcctcgaagg cggcgtcgag     240
ccgaacaagc cggtgcgcta cagctacacg cgccaggcgc gcggcagttg gtcgctgaac     300
tggctggtac cgatcggcca cgagaagccc tcgaacatca aggtgttcat ccacgaactg     360
aacgccggca accagctcag ccacatgtcg ccgatctaca ccatcgagat gggcgacgag     420
ttgctggcga agctggcgcg cgatgccacc ttcttcgtca gggcgcacga gagcaacgag     480
atgcagccga cgctcgccat cagccatgcc ggggtcagcg tggtcatggc ccagacccag     540
ccgcgccggg aaaagcgctg gagcgaatgg gccagcggca aggtgttgtg cctgctcgac     600
ccgctggacg gggtctacaa ctacctcgcc cagcaacgct gcaacctcga cgatacctgg     660
gaaggcaaga tctaccgggt gctcgccggc aacccggcga agcatgacct ggacatcaaa     720
cccacggtca tcagtcatcg cctgcacttt ccgagggcg gcagcctggc cgcgctgacc     780
gcgcaccagg cttgccacct gccgctggag actttcaccc cgtcatcgcca gccgcgcggc     840 tgggaacaac tggagcagtg cggctatccg gtgcagcggc tggtcgccct ctacctggcg     900
```

```
gcgcggctgt cgtggaacca ggtcgaccag gtgatccgca acgccctggc cagccccggc      960
agcggcggcg acctgggcga agcgatccgc gagcagccgg agcaggcccg tctggccctg     1020
accctggccg ccgccgagag cgagcgcttc gtccggcagg gcaccggcaa cgacgaggcc     1080
ggcgcggcca acgccgacgt ggtgagcctg acctgcccgg tcgccgccgg tgaatgcgcg     1140
ggcccggcgg acagcggcga cgccctgctg gagcgcaact atcccactgg cgcggagttc     1200
ctcggcgacg gcggcgacgt cagcttcagc acccgcggca cgcagaactg gacggtggag     1260
cggctgctcc aggcgcaccg ccaactggag gagcgcggct atgtgttcgt cggctaccac     1320
ggcaccttcc tcgaagcggc gcaaagcatc gtcttcggcg gggtgcgcgc gcgcagccag     1380
gacctcgacg cgatctggcg cggtttctat atcgccggcg atccggcgct ggcctacggc     1440
tacgcccagg accaggaacc cgacgcacgc ggccggatcc gcaacggtgc cctgctgcgg     1500
gtctatgtgc cgcgctcgag cctgccgggc ttctaccgca ccagcctgac cctggccgcg     1560
ccggaggcgg cgggcgaggt cgaacggctg atcggccatc cgctgccgct cgcctggac     1620 gccatcaccg gccccgagga ggaaggcggg cgcctggaga ccattctcgg ctggccgctg     1680
gccgagcgca ccgtggtgat tccctcggcg atccccaccg acccgcgcaa cgtcggcggc     1740
gacctcgacc cgtccagcat ccccgacaag gaacaggcga tcagcgccct gccggactac     1800
gccagccagc ccggcaaacc gccgcgcgag gacctgaag                            1839
```

<210> SEQ ID NO 10
<211> LENGTH: 27
<212> TYPE: DNA
<213> ORGANISM: Pseudomonas sp.

<400> SEQUENCE: 10

```
aggtacagag gacgctacta agaaaga                                            27
```

<210> SEQ ID NO 11
<211> LENGTH: 19
<212> TYPE: DNA
<213> ORGANISM: Pseudomonas sp.

<400> SEQUENCE: 11

```
tcagcaggat cgggtttga                                                     19
```

<210> SEQ ID NO 12
<211> LENGTH: 17
<212> TYPE: PRT
<213> ORGANISM: Artificial Sequence
<220> FEATURE:
<223> OTHER INFORMATION: Peptide

<400> SEQUENCE: 12

```
Lys Cys Asp Asp Phe Lys Gln Gly Thr Gln Glu Pro Ile Ser Cys Ser
  1               5                  10                  15

Lys
```

US 7,611,714 B2

METHODS AND COMPOSITIONS FOR IMMUNIZING AGAINST PSEUDOMONAS INFECTION

This application is entitled to and claims benefit of U.S. Provisional Application No. 60/616,125, file Oct. 4, 2004, which is hereby incorporated by reference in its entirety.

1. FIELD OF THE INVENTION

The present invention relates, in part, to methods and compositions for immunizing against infection by *Pseudomonas* ssp. The methods and compositions rely, in part, on administering a chimeric immunogen comprising certain *Pseudomonas* pilin peptides to a subject to be immunized.

2. BACKGROUND

Immunization against bacterial or viral infection has greatly contributed to relief from infectious disease. Generally, immunization relies on administering an inactivated or attenuated pathogen to the subject to be immunized. For example, hepatitis B vaccines can be made by inactivating viral particles with formaldehyde, while some polio vaccines consist of attenuated polio strains that cannot mount a full-scale infection. In either case, the subject's immune system is stimulated to mount a protective immune response by interacting with the inactivated or attenuated pathogen. See, e.g., Kuby, 1997, *Immunology* W.H. Freeman and Company, New York.

This approach has proved successful for immunizing against a number of pathogens. Indeed, many afflictions that plagued mankind for recorded history have been essentially eliminated by immunization with attenuated or inactivated pathogens. See id. Nonetheless, this approach is not effective to immunize against infection by many pathogens that continue to pose significant public health problems. In particular, no vaccine presently exists that has been approved for immunization against *Pseudomonas* ssp. infection. The absence of such a vaccine presents significant public health problems.

For example, *Pseudomonas aeruginosa* infections account for between 10% and 20% of all infections acquired in most hospitals. *Pseudomonas* commonly infects patients with a variety of other afflictions, such as cystic fibrosis, burns, organ transplants, and intravenous-drug addiction. Such infections can lead to serious conditions, including endophthalmitis, endocarditis, meningitis, pneumonia, and septicemia. In subjects with cystic fibrosis, *Pseudomonas aeruginosa* colonization of the lungs represents a significant negative milestone in the progression of this disease. See, for example, Ratgen, 2001, *Int J Antimicrob Agents* 17:93-96. Once colonized, such subjects suffer both the damaging effects of virulence factors secreted by the bacteria and the inflammatory response of the host immune system.

Initially, *Pseudomonas* colonization of the lungs requires adhesion of the bacteria to the lung epithelium. Such adhesion is mediated, in part, by an interaction between the *Pseudomonas* pilus and extracellular glycoproteins present on lung epithelial cells. The *Pseudomonas* pilus is composed of many subunits of Type IV pilin protein that polymerize to form the pilus. See, e.g., Forest et al., 1997, *Gene* 192(1): 165-9 and Parge, 1995, *Nature* 378(6552):32-8.

More specifically, *Pseudomonas aeruginosa* Type IV pilin proteins bind to asialoGM1 receptors on epithelial cells. See, e.g., Saiman et al., 1993, *J. Clin. Invest.* 92 (4): 1875-80; Sheth et al., 1994, *Mol. Microbiol.* 11(4):715-23; Imundo et al., 1995, *Proc. Natl. Acad. Sci. USA* 92(7):3019-23; and Hahn, 1997, *Gene* 192(1):99-108. The portion of pilin responsible for this interaction has been mapped to a C-terminal loop present in the tip of the bacterial pilus. See Lee et al., 1994, *Mol. Microbiol.* 11(4):705-13. This C-terminal loop is formed by amino acids 122-148 of the pilin protein in a β-turn loop subtended from a disulfide bond. See, e.g., Campbell et al., 1997, *Biochemistry* 36(42):12791-80; Campbell et al., 1997, *J. Mol. Biol.* 267(2):382-402; Hazes et al., 2000, *J. Mol. Biol.* 299(4):1005-1017; and McInnes et al., 1993, *Biochemistry* 32(49):13432-40. Disruption of the interaction between this region of Type IV pilin and asialoGM1 receptors prevents adherence of the bacteria to the epithelial cell and prevents effective bacterial colonization. See Hertle et al., 2001, *Infect. Immun.* 69:6962-6969.

Previous efforts to vaccinate against *Pseudomonas* infection by immunizing with *Pseudomonas* pilin protein or derivatives thereof have yielded lackluster results. Immunization with whole pilin protein, with or without adjuvant, is not effective to prevent *Pseudomonas* infection because the most immunogenic portion of the pilin protein is not the loop that mediates adherence to epithelial cells. See, e.g., Sastry et al., 1985, *Ca. J. Biochem. Cell Biol.* 63:284-291. Thus, antibodies raised against the entire pilin protein are principally specific for another region of the pilin protein and thus do not disrupt the interaction that mediates bacterial adherence.

Vaccine compositions that comprise only the C-terminal loop (residues 128-144) of the pilin protein have also been tested for the ability to protect against *Pseudomonas* infection. See, e.g., U.S. Pat. Nos. 5,612,036 and 5,445,818. These vaccines induce a humoral immune response specific for the C-terminal loop, and antibodies produced in the response can prevent *Pseudomonas* adherence to epithelial cells in vitro. Experiments by these researchers showed that pilin vaccine compositions that comprise the same adjuvant and peptides that correspond to amino acids 121-148 of Type IV pilin were not effective to induce a protective immune response.

Further, chimeric proteins constructed from *Pseudomonas* exotoxin A ("PE") derivatives and peptides corresponding to amino acids 128-144 of Type IV pilin protein have also been tested for their ability to induce a protective immune response. See Hertle et al., 2001, *Infect. Immun.* 69:6962-6969. Nonetheless, none of these attempts has to date resulted in a vaccine that has been approved as effective to immunize against *Pseudomonas* infection. Thus, there remains an unmet need for methods and compositions for immunizing against *Pseudomonas* infection.

3. SUMMARY OF THE INVENTION

The chimeric immunogens of the invention comprise a heterologous antigen and can elicit humoral, cell-mediated and secretory immune responses against the heterologous antigen. Such chimeras are useful, for example, in vaccines against infection by organisms for which conventional vaccines are not practical.

Accordingly, in certain aspects, the invention provides a chimeric immunogen that comprises a receptor binding domain, a translocation domain, and a *Pseudomonas* pilin peptide comprising an amino acid sequence that is TAADG-LWKCTSDQDEQFIPKGCSK (SEQ ID NO.:1). In certain embodiments, the chimeric immunogen, when administered to a subject, induces an immune response in the subject that is effective to reduce adherence of a microorganism that expresses the *Pseudomonas* pilin peptide to epithelial cells of the subject.

Figure 8:
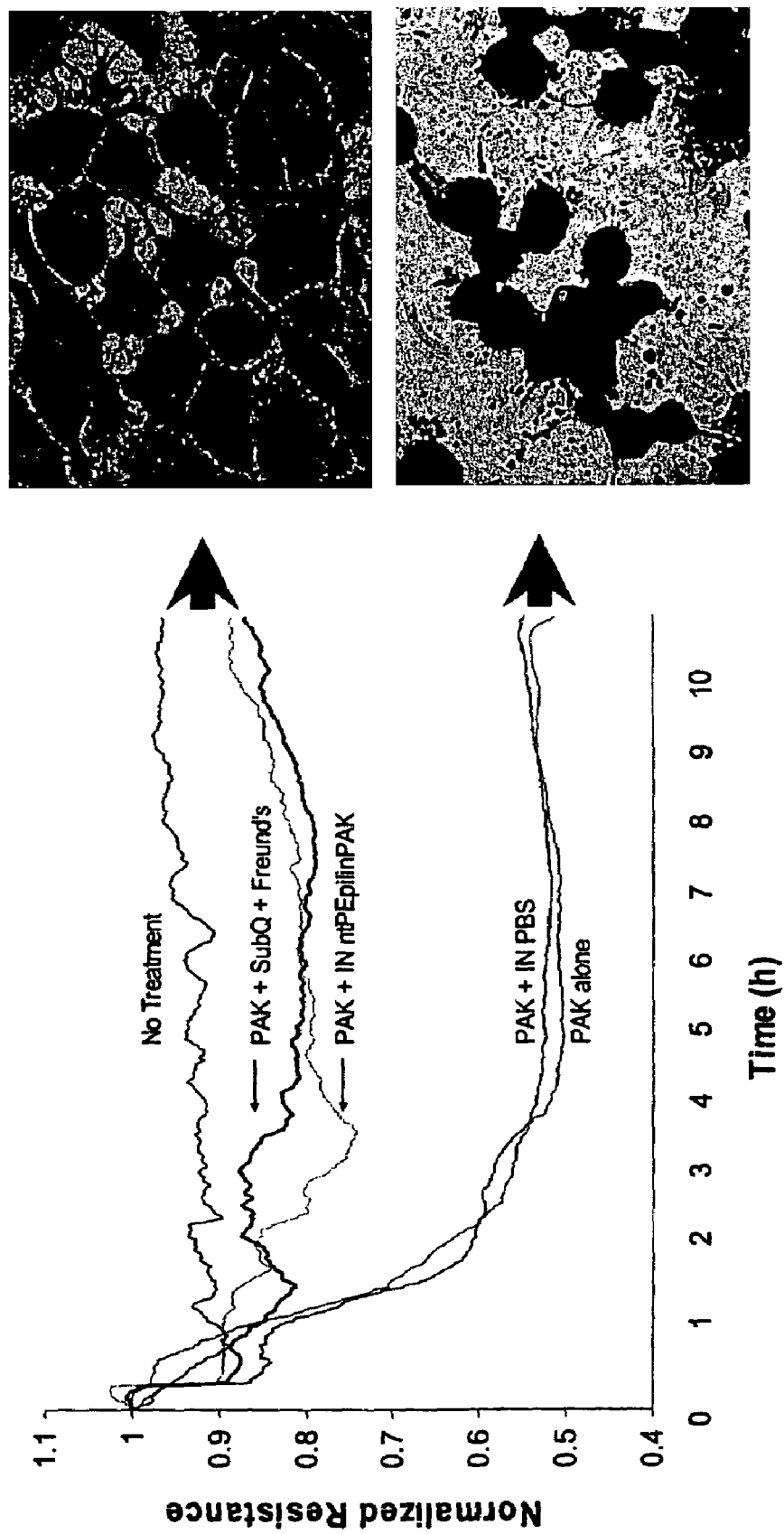

In another aspect, the invention provides a method for inducing an immune response in a subject that comprises administering to the subject an effective amount of a chimeric immunogen comprising a receptor binding domain, a translocation domain, and a *Pseudomonas* pilin peptide that comprises an amino acid sequence that is TAADGLWKCTS-DQDEQFIPKGCSK (SEQ ID NO.: 1). Administration of the chimeric immunogen induces an immune response in the subject that is effective to reduce adherence of a microorganism expressing the *Pseudomonas* pilin peptide to epithelial cells of the subject when the chimeric immunogen is administered to the subject.

In yet another aspect, the invention provides a method for generating in a subject antibodies specific for a *Pseudomonas* pilin peptide having an amino acid sequence that is TAADGLWKCTSDQDEQFIPKGCSK (SEQ ID NO.:1). The method comprises administering to said subject an effective amount of a chimeric immunogen comprising a receptor binding domain, a translocation domain, and a *Pseudomonas* pilin peptide that comprises an amino acid sequence that is TAADGLWKCTSDQDEQFIPKGCSK (SEQ ID NO.:1).

In still another aspect, the invention provides a polynucleotide that encodes a chimeric immunogen that comprises a receptor binding domain, a translocation domain, and a *Pseudomonas* pilin peptide that comprises an amino acid sequence that is TAADGLWKCTSDQDEQFIPKGCSK (SEQ ID NO.:1).

In yet another aspect, the invention provides expression vectors that comprise a polynucleotide of the invention.

In still another aspect, the invention provides cells comprising an expression vector of the invention.

In yet another aspect, the invention provides a composition comprising a chimeric immunogen that comprises a receptor binding domain, a translocation domain, and a *Pseudomonas* pilin peptide that has an amino acid sequence that is TAADGLWKCTSDQDEQFIPKGCSK (SEQ ID NO.:1) In certain embodiments, the composition further comprises a pharmaceutically acceptable diluent, excipient, vehicle, or carrier.

4. BRIEF DESCRIPTION OF THE DRAWINGS

FIG. 1 presents a diagram of a chimeric immunogen. The gene encoding *Ps. aeruginosa* exotoxin A (PE) where a glutamic acid in the 553 position has been deleted (ΔE553) to produce a nontoxic form of the enzyme (ntPE) was cut to remove twenty amino acid that included the Ib loop domain. This segment was replaced by ligation with an oligonucleotide duplex encoding 24 amino acids of the C-terminal domain sequence of the PAK strain of *Ps. aeruginosa*. Cysteine residues available for cross-linking are underlined. Three amino acids not derived from either ntPE or *Ps. aeruginosa* that were introduced by the cloning strategy are italicized.

FIG. 2 presents the results of SDS-PAGE (FIG. 2A) and Western blot (FIG. 2B) analysis of ntPE, ntPEpilinPAK and pilin protein purified from the PAK strain of *Ps. aeruginosa*. The monoclonal antibody used in the Western blot presented in FIG. 2B, 1D10, was produced at A&G Pharmaceutical, Inc. (Columbia, Md.) in BALB/c mice following immunization with a chimeric immunogen comprising amino acids 128-144 of *Ps. aeruginosa* PAK pilin protein short insert and was shown by ELISA to react with this chimeric immunogen and ntPEpilinPAK but not ntPE.

FIG. 3 demonstrates the ability of a toxic form of the chimeric immunogen (PEpilinPAK) and of native PE to induce apoptosis in L929 (ATCC CLL-1) cells in vitro. The assay also demonstrates the absence of toxicity for the chimeric immunogen ntPEpilinPAK. This assay was performed as described in Ogata et al., 1990, *J. Biol. Chem.* 265:20678-85.

FIG. 4 presents pictures showing the cellular distribution of CD91 and uptake of biotin-labeled ntPEpilinPAK in mouse nasal mucosa. FIG. 4A shows isolated naïve nasal tissue demonstrated extensive labeling in epithelial cells and specific cells in submucosal region consistent with phagocytic cell distribution. FIG. 4B illustrates negative control tissue, which was handled identically except that an irrelevant primary isotype antibody was used and the same detection format using colorimetric substrate conversion by horseradish peroxidase coupled to streptavidin (HRP-strep). FIG. 4C shows distribution of biotin detected by HRP-strep 30 min following intranasal application of biotin-labeled ntPEpilinPAK.

FIG. 5 presents anti-immunogen antibody responses in serum and saliva. Standard format ELISA protocols were used to measure anti-ntPEpilinPAK serum IgG, salivary IgG, salivary IgA and serum IgA antibody levels for mice dosed intranasally (IN) with 1, 10 or 100 μg ntPEpilinPAK (n=8 per group). Negative controls received an equal volume of carrier buffer (PBS) by IN instillation and positive controls received 10 μg ntPEpilinPAK injected subcutaneously in a regime of complete and incomplete Freund's adjuvant. Statistical assessment was performed using one-way ANOVA and data is expressed as mean±SEM; ($P<0.001$, ***) compared to PBS IN values.

FIG. 6 demonstrates induction of anti-pilin antibody responses following administration of a chimeric immunogen. Serum IgG antibodies specific for the PAK pilin loop sequence was determined using a standard ELISA format for mice dosed intranasally with 1, 10 or 100 μg ntPEpilinPAK. Negative control animals received an equal volume of carrier buffer (PBS) by intranasal instillation and positive controls received 10 μg ntPEpilinPAK injected subcutaneously in a regime of complete and incomplete Freund's adjuvant (n=8 per group). Statistical assessment was performed using one-way ANOVA and data is expressed as mean±SEM; ($P<0.001$, ***) compared to PBS IN values.

FIG. 7 demonstrates that saliva from mice immunized with a pilin peptide-containing chimeric immunogen blocks pilin-mediated bacteria binding. A549 cell lawns, grown to near confluent densities on Lab-Tek II 8-chamber slides were exposed to 50 *Ps. aeruginosa* PAK strain bacteria for 2 hr prior to washing, mild fixation and Geimsa staining. Fifty cells in each well were visually inspected using a light microscope to determine the average number of bacteria associated with each A549 cell. FIG. 7A shows that adherence of bacteria was selectively inhibited by increasing concentrations of ntPEpilinPAK but not by ntPE lacking the pilin loop insert (n=4). FIG. 7B indicates that saliva obtained from mice immunized with ntPEpilinPAK by intranasal (IN) instillation or by subcutaneous injection with a cocktail of compete/incomplete Freund's adjuvant (SubQ+Freund's) and diluted 1:100 reduced bacteria adherence relative to mice dosed IN with PBS (n=4). FIG. 7C shows amount of unbound *Ps. aeruginosa* found in A549-bacteria media following 2 hr incubation with PAK strain of *Ps. aeruginosa* with saliva samples (diluted 1:100 in cell culture media) obtained from mice immunized IN with 1, 10 or 100 μg ntPEpilinPAK. Unbound bacteria were quantitated by real-time polymerase chain reaction performed in duplicate. Statistical assessment was performed using one-way ANOVA and data is expressed as mean±SEM; ($P<0.001$, ***) compared to PBS IN values.

FIG. 8 demonstrates that saliva from mice immunized with a pilin peptide containing-chimeric immunogen blocks pilin-mediated cytotoxicity. FIG. 8 presents a time course of resistance (normalized to values at the time of bacterial addition) following the introduction of ~50 Ps. aeruginosa PAK strain bacteria per A549 cell grown in electrode chambers to perform electric cell-substrate impedance sensing. Saliva obtained from mice following subcutaneous injection of 10 μg ntPEpilinPAK with a complete/incomplete Freund's adjuvant cocktail (SubQ+Freund's) or intranasal (IN) immunization with 100 μg ntPEpilinPAK or IN instillation of an equal volume of PBS was added in a dilution of 1:100 with antibiotic-free medium. Decline in resistance, derived from original impedance measurements, demonstrates rounding and lifting of A549 from substrate.

Figure 9:
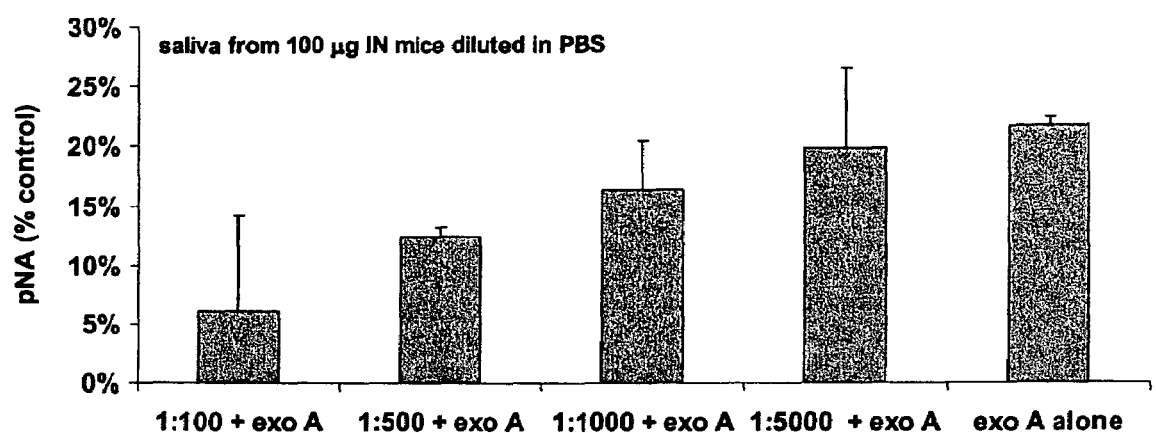

FIG. 9 demonstrates that saliva from mice immunized with a pilin peptide-containing chimeric immunogen attenuates exotoxin A-induced caspase-3 activation. Saliva obtained from mice following intranasal (IN) immunization with 100 μg ntPEpilinPAK was added to confluent A549 cells at a dilution of 1:100, 1:500, 1:1,000, and 1:5,000 in the presence of 10 μg/ml exotoxin A for 24 hrs at 37° C. in a 5% $CO_2$/95% air atmosphere. Caspase-3 activity was assayed by measuring p-nitroaniline (pNA). Data is presented as % control.

Figure 10:
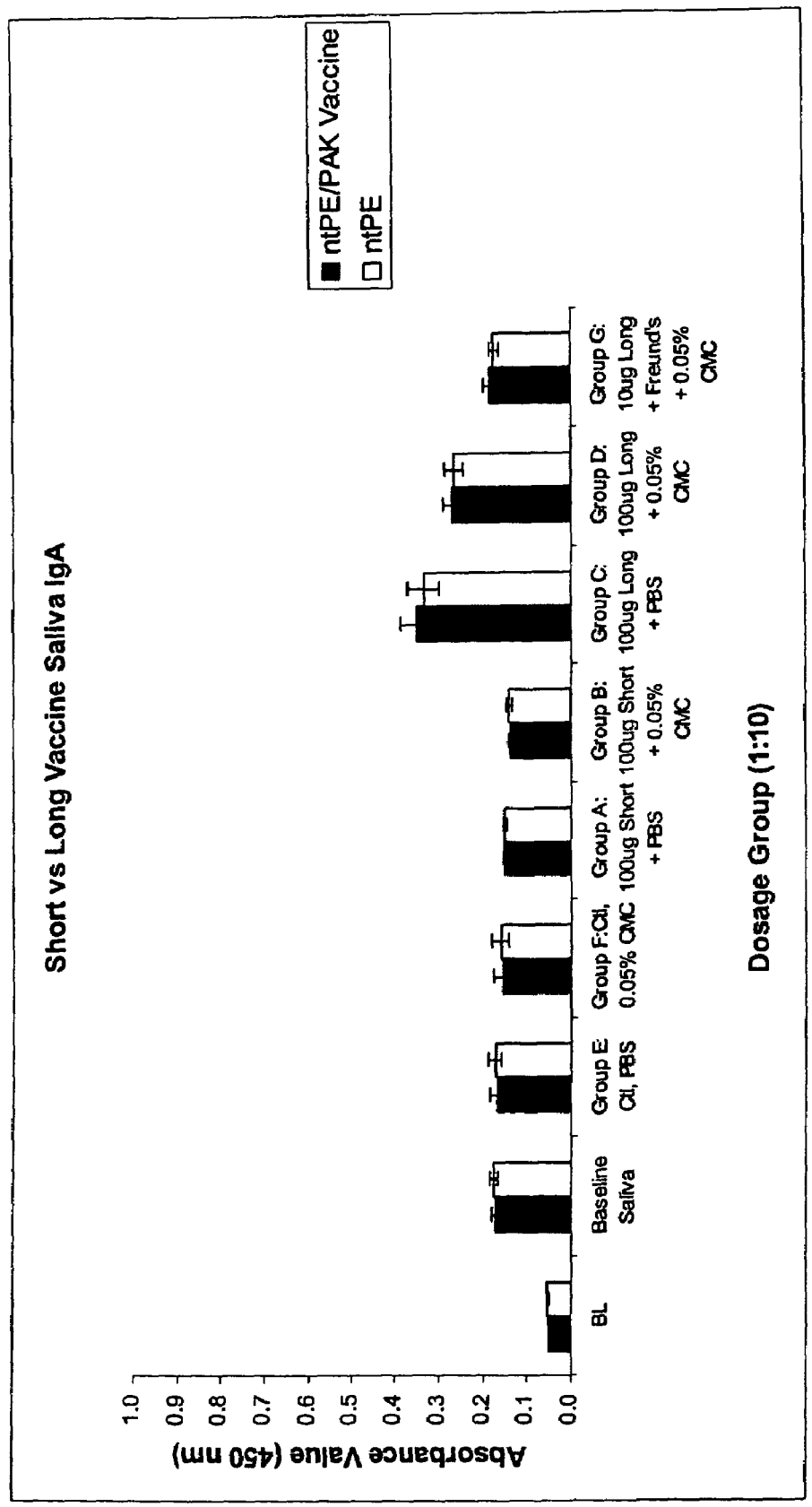

FIG. 10 presents the results of ELISA assays comparing amounts of salivary IgA induced following administration of a chimeric immunogen comprising a pilin peptide corresponding to residues 128-144 of the Ps. aeruginosa strain PAK pilin protein (the "short" chimeric immunogen) and a chimeric immunogen comprising a pilin peptide corresponding to residues 121-144 of Ps. aeruginosa pilin peptide (the "long" chimeric immunogen).

Figure 11:
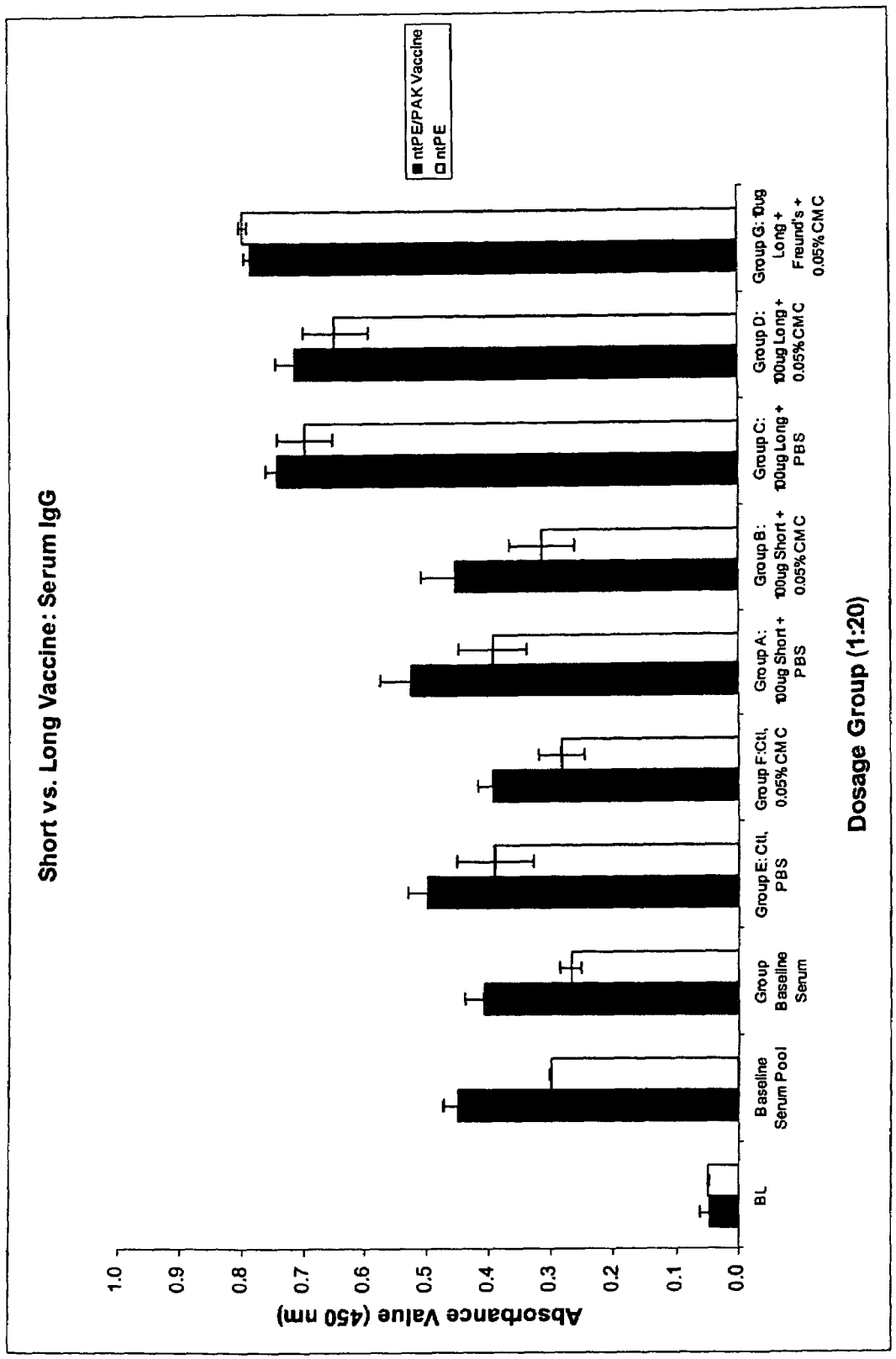

FIG. 11 presents the results of ELISA assays comparing amounts of serum IgG induced following administration of a chimeric immunogen comprising a pilin peptide corresponding to residues 128-144 of the Ps. aeruginosa strain PAK pilin protein (the "short" chimeric immunogen) and a chimeric immunogen comprising a pilin peptide corresponding to residues 121-144 of Ps. aeruginosa pilin peptide (the "long" chimeric immunogen).

FIG. 12 demonstrates that saliva obtained from mice immunized with an immunogen that contains a pilin peptide from Pseudomonas aeruginosa strain K can also prevent adherence of other strains of Pseudomonas to A549 cells in an assay performed according to the protocol presented in the description of FIG. 7.

FIG. 13 presents an exemplary amino acid sequence of Pseudomonas aeruginosa exotoxin A.

5. DETAILED DESCRIPTION OF THE INVENTION

5.1. Definitions

Unless defined otherwise, all technical and scientific terms used herein have the meaning commonly understood by a person skilled in the art to which this invention belongs. As used herein, the following terms have the meanings ascribed to them unless specified otherwise.

A "ligand" is a compound that specifically binds to a target molecule. Exemplary ligands include, but are not limited to, an antibody, a cytokine, a substrate, a signaling molecule, and the like.

A "receptor" is compound that specifically binds to a ligand.

A ligand or a receptor (e.g., an antibody) "specifically binds to" or "is specifically immunoreactive with" another molecule when the ligand or receptor functions in a binding reaction that indicates the presence of the molecule in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to another polynucleotide comprising a complementary sequence and an antibody specifically binds under immunoassay conditions to an antigen bearing an epitope used to induce the antibody.

"Immunoassay" refers to a method of detecting an analyte in a sample involving contacting the sample with an antibody that specifically binds to the analyte and detecting binding between the antibody and the analyte. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. In one example, an antibody that binds a particular antigen with an affinity ($K_m$) of about 10 μM specifically binds the antigen.

"Vaccine" refers to an agent or composition containing an agent effective to confer an at least partially prophylactic or therapeutic degree of immunity on an organism while causing only very low levels of morbidity or mortality. Methods of making vaccines are, of course, useful in the study of the immune system and in preventing and treating animal or human disease.

An "immune response" refers to one or more biological activities mediated by cells of the immune system in a subject. Such biological activities include, but are not limited to, production of antibodies; activation and proliferation of immune cells, such as, e.g., B cells, T cells, macrophages, leukocytes, lymphocytes, etc.; release of messenger molecules, such as cytokines, chemokines, interleukins, tumor necrosis factors, growth factors, etc.; and the like. An immune response is typically mounted when a cell of the immune system encounters non-self antigen that is recognized by a receptor present on the surface of the immune cell. The immune response preferably protects the subject to some degree against infection by a pathogen that bears the antigen against which the immune response is mounted.

An immune response may be "elicited," "induced," or "induced against" a particular antigen. Each of these terms is intended to be synonymous as used herein and refers to the ability of the chimeric immunogen to generate an immune response upon administration to a subject.

An "immunogen" is a molecule or combination of molecules that can induce an immune response in a subject when the immunogen is administered to the subject.

"Immunizing" refers to administering an immunogen to a subject.

An "immunogenic amount" of a compound is an amount of the compound effective to elicit an immune response in a subject.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences,* 19*th Ed.* 1995, Mack Publishing Co., Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

Preferred pharmaceutical carriers depend upon the intended mode of administration of the active agent. Typical modes of administration include enteral (e.g., oral, intranasal, rectal, or vaginal) or parenteral (e.g., subcutaneous, intramuscular, intravenous or intraperitoneal injection; or topical, transdermal, or transmucosal administration).

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

A "subject" of diagnosis, treatment, or administration is a human or non-human animal, including a mammal, such as a rodent (e.g., a mouse or rat), a lagomorph (e.g., a rabbit), or a primate. A subject of diagnosis, treatment, or administration is preferably a primate, and more preferably a human.

"Treatment" refers to prophylactic treatment or therapeutic treatment. A "prophylactic" treatment is a treatment administered to a subject who does not exhibit signs of a disease or exhibits only early signs for the purpose of decreasing the risk of developing pathology. A "therapeutic" treatment is a treatment administered to a subject who exhibits signs of pathology for the purpose of diminishing, slowing the progression, eliminating, or halting those signs.

"*Pseudomonas* exotoxin A" or "PE" is secreted by *Pseudomonas aeruginosa* as a 67 kD protein composed of three prominent globular domains (Ia, II, and III) and one small subdomain (Ib) that connects domains II and III. See A. S. Allured et al., 1986, *Proc. Natl. Acad. Sci.* 83:1320-1324, and FIG. 1, which presents the amino acid sequence of native PE. Without intending to be bound to any particular theory or mechanism of action, domain Ia of PE is believed to mediate cell binding because domain Ia specifically binds to the low density lipoprotein receptor-related protein ("LRP"), also known as the α2-macroglobulin receptor ("α2-MR") and CD-91. See M. Z. Kounnas et al., 1992, *J. Biol. Chem.* 267: 12420-23. Domain Ia spans amino acids 1-252. Domain II of PE is believed to mediate translocation to the interior of a cell following binding of domain Ia to the α2-MR. Domain II spans amino acids 253-364. Domain Ib has no known function and spans amino acids 365-399. Domain III mediates cytotoxicity of PE and includes an endoplasmic reticulum retention sequence. PE cytotoxicity is believed to result from ADP ribosylation of elongation factor 2, which inactivates protein synthesis. Domain III spans amino acids 400-613 of PE. Deleting amino acid E553 ("ΔE553") from domain III eliminates EF2 ADP ribosylation activity and detoxifies PE. PE having the mutation ΔE553 is referred to herein as "PEΔE553." Genetically modified forms of PE are described in, e.g., U.S. Pat. Nos. 5,602,095; 5,512,658 and 5,458,878. *Pseudomonas* exotoxin, as used herein, also includes genetically modified, allelic, and chemically inactivated forms of PE within this definition. See, e.g., Vasil et al., 1986, *Infect.* *Immunol.* 52:538-48. Further, reference to the various domains of PE is made herein to the reference PE sequence presented as FIG. 13. However, one or more domain from modified PE, e.g., genetically or chemically modified PE, or a portion of such domains, can also be used in the chimeric immunogens of the invention so long as the domains retain functional activity. One of skill in the art can readily identify such domains of such modified PE based on, for example, homology to the PE sequence exemplified in FIG. 2 and test for functional activity using, for example, the assays described below.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions. Thus, the polynucleotide whose sequence 5'-TATAC-3' is complementary to a polynucleotide whose sequence is 5'-GTATA-3'.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.,* 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Arg (R), Asn (N), Asp (D), Glu (E), Gln (O), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, *J. Mol. Biol.* 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and RNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Amplification" refers to any means by which a polynucleotide sequence is copied and thus expanded into a larger number of polynucleotide molecules, e.g., by reverse transcription, polymerase chain reaction, ligase chain reaction, and the like.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids can be found in Tijssen, 1993, *Laboratory Techniques in Biochemistry and Molecular Biology—Hybridization with Nucleic Acid Probes*, part I, chapter 2, "Overview of principles of hybridization and the strategy of nucleic acid probe assays", Elsevier, N.Y.; Sambrook et al., 2001, *Molecular Cloning: A Laboratory Manual*, Cold Spring Harbor Laboratory, 3$^{rd}$ ed., NY; and Ausubel et al., eds., Current Edition, *Current Protocols in Molecular Biology*, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

One example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. Conventional notation is used herein to portray polypeptide sequences; the beginning of a polypeptide sequence is the amino-terminus, while the end of a polypeptide sequence is the carboxyl-terminus.

The term "protein" typically refers to large polypeptides, for example, polypeptides comprising more than about 50 amino acids. The term "protein" can also refer to dimers, trimers, and multimers that comprise more than one polypeptide.

The term "peptide" typically refers to short polypeptides, for example, polypeptides comprising about 50 or less amino acids.

"Conservative substitution" refers to the substitution in a polypeptide of an amino acid with a functionally similar amino acid. The following six groups each contain amino acids that are conservative substitutions for one another:
Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W).

5.2. Chimeric Immunogens

Generally, the chimeric immunogens of the present invention are polypeptides that comprise structural domains corresponding to domains Ia and II of PE. The chimeric immunogens can optionally comprise structural domains corresponding to the other domains of PE, domains Ib and III. These structural domains perform certain functions, including, but not limited to, cell recognition, translocation and endoplasmic reticulum retention, that correspond to the functions of the domains of PE. By including or omitting the optional domains of PE, the character of the induced immune response can be modulated, as described below.

In addition to the portions of the molecule that correspond to PE functional domains, the chimeric immunogens of this invention further comprise a heterologous antigen. The heterologous antigen can be introduced into or replace some or all of the Ib domain of PE, or the heterologous antigen can be introduced into or replace any other portion of the molecule that does not disrupt a cell-binding or translocation activity. An immune response specific for the heterologous antigen is elicited upon administration of the chimeric immunogen to a subject.

Accordingly, the chimeric immunogens of the invention generally comprise the following structural elements, each element imparting particular functions to the chimeric immunogen: (1) a "receptor binding domain" that functions as a ligand for a cell surface receptor and that mediates binding of the protein to a cell; (2) a "translocation domain" that mediates translocation from the exterior of the cell to the interior of the cell; (3) the heterologous antigen; and, optionally, (4) an "endoplasmic reticulum ("ER") retention domain" that translocates the chimeric immunogen from the endosome to the endoplasmic reticulum, from which it enters the cytosol. The chimeric immunogen can still induce an immune response in the absence of the ER retention domain, though this absence changes the nature of the induced immune response, as described below.

The domains of the chimeric immunogens other than the heterologous antigen can be present in the order set forth above, i.e., domain Ia is closest to the N-terminus, then the translocation domain, then the ER retention domain. In fact, this arrangement is preferred. However, the domains of the chimeric immunogen can be in any order as long as the domains retain their functional activities. Several representative assays to test such functional activities are set forth below.

Such chimeric immunogens offer several advantages over conventional immunogens. To begin with, certain embodiments of the chimeric immunogens can be constructed and expressed in recombinant systems. These systems eliminate any requirement to crosslink the heterologous antigen to a carrier protein. Recombinant technology also allows one to make a chimeric immunogen having an insertion site designed for introduction of any desired heterologous antigen. Such insertion sites allow the skilled artisan to quickly and easily produce chimeric immunogens that comprise either known variants of a heterologous antigen or emerging variants of evolving heterologous antigens.

Further, the chimeric immunogens can be engineered to alter the function of their domains in order to tailor the activity of the immunogen to its intended use. For example, by selecting the appropriate receptor binding domain, the skilled artisan can target the chimeric immunogen to bind to a desired cell or cell line.

In addition, because certain embodiments of the chimeric immunogens include a constrained cysteine-cysteine loop, heterologous antigens that are so constrained in nature can be presented in native or near-native conformation. By doing so, the induced immune response is specific for antigen in its native conformation, and can more effectively protect the subject from infection by the pathogen. For example, a turn-turn-helix motif can be observed in peptides constrained by a disulfide bond, but not in linear peptides. See Ogata et al., 1990, *Biol. Chem.* 265:20678-85.

Moreover, the chimeric immunogens can be used to elicit a humoral, a cell-mediated or a secretory immune response. Depending on the pathway by which the chimeric immunogen is processed in an antigen-presenting cell, the chimeric immunogen can induce an immune response mediated by either class I or class II MHC. See Becerrra et al., 2003, *Surgery* 133:404-410 and Lippolis et al., 2000, *Cell. Immunol.* 203:75-83. Further, if the PE chimeras are administered to a mucosal surface of the subject, a secretory immune response involving IgA can be induced. See, e.g., Mrsny et al., 1999, *Vaccine* 17:1425-1433 and Mrsny et al., 2002, *Drug Discovery Today* 7:247-258.

The chimeric immunogens of the invention can also be used to elicit a protective immune response without using attenuated or inactivated pathogens. The inactivation or attenuation of such pathogens can sometimes be incomplete, or the pathogen can revert to be fully infectious, leading to infection by the pathogen upon administration of the vaccine. For example, administration of attenuated polio vaccine actually results in paralytic polio in about 1 in 4 million subjects receiving the vaccine. See Kuby, 1997, *Immunology Ch.* 18, W.H. Freeman and Company, New York.

Thus, in certain aspects, the invention provides a chimeric immunogen that comprises a receptor binding domain, a translocation domain, and a *Pseudomonas* pilin peptide comprising an amino acid sequence that is TAADGLWKCTS-DQDEQFIPKGCSK (SEQ ID NO.:1). This particular pilin peptide corresponds to residues 121-144 of *Ps. aeruginosa* PAK pilin protein. In certain embodiments, the chimeric immunogen, when administered to a subject, can induce an immune response in the subject that is effective to reduce adherence of a microorganism that expresses said *Pseudomonas* pilin peptide to epithelial cells of the subject. In other embodiments, the chimeric immunogen, when administered to a subject, generates an immune response in the subject that reduces the cytotoxicity of *Pseudomonas* exotoxin A to the subject. In certain embodiments, the chimeric immunogen, when administered to a subject, can induce an immune response in the subject that is effective to reduce the incidence of infection by a microorganism that expresses said *Pseudomonas* pilin peptide in the subject. In certain embodiments, the chimeric immunogen, when administered to a subject, can induce an immune response in the subject that is effective to prevent infection by a microorganism that expresses said *Pseudomonas* pilin peptide in the subject. In certain embodiments, the chimeric immunogen, when administered to a subject, can induce an immune response in the subject that is effective to treat infection by a microorganism that expresses said *Pseudomonas* pilin peptide in the subject.

In certain embodiments, the chimeric immunogen further comprises an endoplasmic reticulum retention domain. In certain embodiments, the *Pseudomonas* pilin peptide is located between said translocation domain and said endoplasmic reticulum retention domain. In certain embodiments, the endoplasmic reticulum retention domain is an enzymatically inactive domain III of *Pseudomonas* exotoxin A. In certain embodiments, the enzymatically inactive domain III of *Pseudomonas* exotoxin A is inactivated by deleting a glutamate at position 553.

In certain embodiments, the endoplasmic reticulum retention domain comprises an ER retention signal that has an amino acid sequence selected from the group of RDEL (SEQ ID NO.:2) or KDEL (SEQ ID NO.:3). In certain embodiments, the ER retention signal is sufficiently near the C-terminus of said endoplasmic reticulum retention domain to result in retention of the chimeric immunogen in the endoplasmic reticulum.

In certain embodiments, the chimeric immunogen comprises a translocation domain that is selected from the group consisting translocation domains from *Pseudomonas* exotoxin A, *diptheria* toxin, pertussis toxin, *cholera* toxin, heat-labile *E. coli* enterotoxin, shiga toxin, and shiga-like toxin. In further embodiments, the translocation domain is domain II of *Pseudomonas* exotoxin A. In yet further embodiments, the translocation domain comprises amino acids 280 to 364 of domain II of *Pseudomonas* exotoxin A.

In certain embodiments, the chimeric immunogen comprises more than one of said *Pseudomonas* pilin peptides.

In certain embodiments, the chimeric immunogen comprises a receptor binding domain that is selected from the group consisting of domain Ia of *Pseudomonas* exotoxin A; a receptor binding domains from *cholera* toxin, *diptheria* toxin, shiga toxin, or shiga-like toxin; a monoclonal antibody, a polyclonal antibody, or a single-chain antibody; TGFα, TGFβ, EGF, PDGF, IGF, or FGF; IL-1, IL-2, IL-3, or IL-6; and MIP-1a, MIP-1b, MCAF, or IL-8. In further embodiments, the receptor binding domain is domain Ia of *Pseudomonas* exotoxin A. In yet further embodiments, the domain Ia of *Pseudomonas* exotoxin A has an amino acid sequence that is SEQ ID NO.:4.

In certain embodiments, the receptor binding domain binds to α2-macroglobulin receptor, epidermal growth factor receptor, transferrin receptor, interleukin-2 receptor, interleukin-6 receptor, interleukin-8 receptor, Fc receptor, poly-IgG receptor, asialoglycopolypeptide receptor, CD3, CD4, CD8, chemokine receptor, CD25, CD11B, CD11C, CD80, CD86, TNFα receptor, TOLL receptor, M-CSF receptor, GM-CSF receptor, scavenger receptor, or VEGF receptor. In further embodiments, the receptor binding domain binds to α2-macroglobulin receptor.

In certain embodiments, the chimeric immunogen has an amino acid sequence that is SEQ ID NO:5.

5.2.1. Receptor Binding Domain

The chimeric immunogens of the invention generally comprise a receptor binding domain. The receptor binding domain can be any receptor binding domain that binds to a cell surface receptor without limitation. Such receptor binding domains are well-known to those of skill in the art. Preferably, the receptor binding domain binds specifically to the cell surface receptor. The receptor binding domain should bind to the cell surface receptor with sufficient affinity to hold the chimeric immunogen in proximity to the cell surface to allow endocytosis of the chimeric immunogen. Representative assays that can routinely be used by the skilled artisan to assess binding of the receptor binding domain to a cell surface receptor are described below.

In certain embodiments, the receptor binding domain can comprise a polypeptide, a peptide, a protein, a lipid, a carbohydrate, or a small organic molecule, or a combination thereof. Examples of each of these molecules that bind to cell surface receptors are well known to those of skill in the art. Suitable peptides, polypeptides, or proteins include, but are not limited to, bacterial toxin receptor binding domains, such as the receptor binding domains from PE, *cholera* toxin, *diptheria* toxin, shiga toxin, shiga-like toxin, etc.; antibodies, including monoclonal, polyclonal, and single-chain antibodies, or derivatives thereof, growth factors, such as TGFα, TGFβ, EGF, PDGF, IGF, FGF, etc.; cytokines, such as IL-1, IL-2, IL-3, IL-6, etc; chemokines, such as MIP-1a, MIP-1b, MCAF, IL-8, etc.; and other ligands, such as CD4, cell adhesion molecules from the immunoglobulin superfamily, integrins, ligands specific for the IgA receptor, etc. See, e.g., Pastan et al., 1992, *Annu. Rev. Biochem.* 61:331-54; and U.S. Pat. Nos. 5,668,255, 5,696,237, 5,863,745, 5,965,406, 6,022,950, 6,051,405, 6,251,392, 6,440,419, and 6,488,926. The skilled artisan can select the appropriate receptor binding domain based upon the expression pattern of the receptor to which the receptor binding domain binds.

Lipids suitable for receptor binding domains include, but are not limited to, lipids that themselves bind cell surface receptors, such as sphingosine-1-phosphate, lysophosphatidic acid, sphingosylphosphorylcholine, retinoic acid, etc.; lipoproteins such as apolipoprotein E, apolipoprotein A, etc., and glycolipids such as lipopolysaccharide, etc.; glycosphingolipids such as globotriaosylceramide and galabiosylceramide; and the like. Carbohydrates suitable for receptor binding domains include, but are not limited to, monosaccharides, disaccharides, and polysaccharides that comprise simple sugars such as glucose, fructose, galactose, etc.; and glycoproteins such as mucins, selectins, and the like. Suitable small organic molecules for receptor binding domains include, but are not limited to, vitamins, such as vitamin A, $B_1$, $B_2$, $B_3$, $B_6$, $B_9$, $B_{12}$, C, D, E, and K, amino acids, and other small molecules that are recognized and/or taken up by receptors present on the surface of epithelial cells.

In certain embodiments, the receptor binding domain can bind to a receptor found on an epithelial cell. In further embodiments, the receptor binding domain can bind to a receptor found on the apical membrane of an epithelial cell. In still further embodiments, the receptor binding domain can bind to a receptor found on the apical membrane of a mucosal epithelial cell. The receptor binding domain can bind to any receptor known to be present on the apical membrane of an epithelial cell by one of skill in the art without limitation. For example, the receptor binding domain can bind to α2-MR. An example of a receptor binding domain that can bind to α2-MR is domain Ia of PE. Accordingly, in certain embodiments, the receptor binding domain is domain Ia of PE. In other embodiments, the receptor binding domain is a portion of domain Ia of PE that can bind to α2-MR.

In certain embodiments, the receptor binding domain can bind to a receptor present on an antigen presenting cell, such as, for example, a dendritic cell or a macrophage. The receptor binding domain can bind to any receptor present on an antigen presenting cell without limitation. For example, the receptor binding domain can bind to any receptor identified as present on a dendritic or other antigen presenting cell identified in Figdor, 2003, *Pathol. Biol.* (*Paris*). 51(2):61-3; Coombes et al., 2001, *Immunol Lett.* 3; 78(2):103-11; Shortman K et al., 1997, *Ciba Found Symp.* 204:130-8; discussion 138-41; Katz, 1998, *Curr Opin Immunol.* 1(2):213-9; and Goldsby et al., 2003, *Immunology, 5th Edition* W.H. Freeman & Company, New York, N.Y. In particular, the receptor binding domain can bind to α2-MR, which is also expressed on the surface of antigen presenting cells. Thus, in certain embodiments, the receptor binding domain can bind to a receptor that is present on both an epithelial cell and on an antigen presenting cell.

In certain embodiments, the receptor binding domains can bind to a cell surface receptor that is selected from the group consisting of α2-macroglobulin receptor, epidermal growth factor receptor, transferrin receptor, interleukin-2 receptor, interleukin-6 receptor, interleukin-8 receptor, Fc receptor, poly-IgG receptor, asialoglycopolypeptide receptor, CD3, CD4, CD8, chemokine receptor, CD25, CD11B, CD11C, CD80, CD86, TNFα receptor, TOLL receptor, M-CSF receptor, GM-CSF receptor, scavenger receptor, and VEGF receptor.

In certain embodiments, the chimeric immunogens of the invention comprise more than one domain that can function as a receptor binding domain. For example, the chimeric immunogen could comprise PE domain Ia in addition to another receptor binding domain.

The receptor binding domain can be attached to the remainder of the chimeric immunogen by any method or means known by one of skill in the art to be useful for attaching such molecules, without limitation. In certain embodiments, the receptor binding domain is expressed together with the remainder of the chimeric immunogen as a fusion protein. Such embodiments are particularly useful when the receptor binding domain and the remainder of the immunogen are formed from peptides or polypeptides.

In other embodiments, the receptor binding domain is connected with the remainder of the chimeric immunogen with a linker. In yet other embodiments, the receptor binding domain is connected with the remainder of the chimeric immunogen without a linker. Either of these embodiments are useful when the receptor binding domain comprises a peptide, polypeptide, protein, lipid, carbohydrate, nucleic acid, or small organic molecule.

In certain embodiments, the linker can form a covalent bond between the receptor binding domain and the remainder of the chimeric immunogen. In other embodiments, the linker can link the receptor binding domain to the remainder of the chimeric immunogen with one or more non-covalent interactions of sufficient affinity. One of skill in the art can readily recognize linkers that interact with each other with sufficient affinity to be useful in the chimeric immunogens of the invention. For example, biotin can be attached to the receptor binding domain, and streptavidin can be attached to the remainder of the molecule. In certain embodiments, the linker can directly link the receptor binding domain to the remainder of the molecule. In other embodiments, the linker itself comprises two or more molecules that associate in order to link the receptor binding domain to the remainder of the molecule. Exemplary linkers include, but are not limited to, straight or branched-chain carbon linkers, heterocyclic carbon linkers, substituted carbon linkers, unsaturated carbon linkers, aromatic carbon linkers, peptide linkers, etc.

In embodiments where a linker is used to connect the receptor binding domain to the remainder of the chimeric immunogen, the linkers can be attached to the receptor binding domain and/or the remainder of the chimeric immunogen by any means or method known by one of skill in the art without limitation. For example, the linker can be attached to the receptor binding domain and/or the remainder of the chimeric immunogen with an ether, ester, thioether, thioester, amide, imide, disulfide or other suitable moiety. The skilled artisan can select the appropriate linker and means for attaching the linker based on the physical and chemical properties of the chosen receptor binding domain and the linker. The linker can be attached to any suitable functional group on the receptor binding domain or the remainder of the molecule. For example, the linker can be attached to sulfhydryl (—S), carboxylic acid (COOH) or free amine (—NH2) groups, which are available for reaction with a suitable functional group on a linker. These groups can also be used to connect the receptor binding domain directly connected with the remainder of the molecule in the absence of a linker.

Further, the receptor binding domain and/or the remainder of the chimeric immunogen can be derivatized in order to facilitate attachment of a linker to these moieties. For example, such derivatization can be accomplished by attaching suitable derivative such as those available from Pierce Chemical Company, Rockford, Ill. Alternatively, derivatization may involve chemical treatment of the receptor binding domain and/or the remainder of the molecule. For example, glycol cleavage of the sugar moiety of a carbohydrate or glycoprotein receptor binding domain with periodate generates free aldehyde groups. These free aldehyde groups may be reacted with free amine or hydrazine groups on the remainder of the molecule in order to connect these portions of the molecule. See U.S. Pat. No. 4,671,958. Further, the skilled artisan can generate free sulfhydryl groups on proteins to provide a reactive moiety for making a disulfide, thioether, theioester, etc. linkage. See U.S. Pat. No. 4,659,839.

Any of these methods for attaching a linker to a receptor binding domain and/or the remainder of a chimeric immunogen can also be used to connect a receptor binding domain with the remainder of the chimeric immunogen in the absence of a linker. In such embodiments, the receptor binding domain is coupled with the remainder of the immunogen using a method suitable for the particular receptor binding domain. Thus, any method suitable for connecting a protein, peptide, polypeptide, nucleic acid, carbohydrate, lipid, or small organic molecule to the remainder of the chimeric immunogen known to one of skill in the art, without limitation, can be used to connect the receptor binding domain to the remainder of the immunogen. In addition to the methods for attaching a linker to a receptor binding domain or the remainder of an immunogen, as described above, the receptor binding domain can be connected with the remainder of the immunogen as described in U.S. Pat. Nos. 6,673,905; 6,585,973; 6,596,475; 5,856,090; 5,663,312; 5,391,723; 6,171,614; 5,366,958; and 5,614,503.

In certain embodiments, the receptor binding domain can be a monoclonal antibody or antigen-binding portion of an antibody. In some of these embodiments, the chimeric immunogen is expressed as a fusion protein that comprises an immunoglobulin heavy chain from an immunoglobulin specific for a receptor on a cell to which the chimeric immunogen is intended to bind, or antigen-binding portion thereof. The light chain of the immunoglobulin, or antigen-binding portion thereof, then can be co-expressed with the chimeric immunogen, thereby forming an antigen-binding light chain-heavy chain dimer. In other embodiments, the antibody, or antigen-binding portion thereof, can be expressed and assembled separately from the remainder of the chimeric immunogen and chemically linked thereto.

5.2.2. Translocation Domain

The chimeric immunogens of the invention also comprise a translocation domain. The translocation domain can be any translocation domain known by one of skill in the art to effect translocation of chimeric proteins that have bound to a cell surface receptor from outside the cell to inside the cell, e.g., the outside of an epithelial cell, such as, for example, a polarized epithelial cell. In certain embodiments, the translocation domain is a translocation domain from PE, *diptheria* toxin, pertussis toxin, *cholera* toxin, heat-labile *E. coli* enterotoxin, shiga toxin, or shiga-like toxin. See, for example, U.S. Pat. Nos. 5,965,406, and 6,022,950. In preferred embodiments, the translocation domain is domain II of PE. In certain embodiments, the translocation domain of domain II of PE has an amino acid sequence that is SEQ ID NO:6.

The translocation domain need not, though it may, comprise the entire amino acid sequence of domain II of native PE, which spans residues 253-364 of PE. For example, the translocation domain can comprise a portion of PE that spans residues 280-344 of domain II of PE. The amino acids at positions 339 and 343 appear to be necessary for translocation. See Siegall et al., 1991, *Biochemistry* 30:7154-59. Further, conservative or nonconservative substitutions can be made to the amino acid sequence of the translocation domain, as long as translocation activity is not substantially eliminated. A representative assay that can routinely be used by one of skill in the art to determine whether a translocation domain has translocation activity is described below.

Without intending to be limited to any particular theory or mechanism of action, the translocation domain is believed to perform at least two important functions in the chimeric immunogens of the invention. First, the translocation domain permits the trafficking of the chimeric immunogen through a polarized epithelial cell into the bloodstream after the immunogen binds to a receptor present on the apical surface of the polarized epithelial cell. This trafficking results in the release of the chimeric immunogen from the basal-lateral membrane of the polarized epithelial cell. Second, the translocation domain facilitates endocytosis of the chimeric immunogen into an antigen presenting cell after the immunogen binds to a receptor present on the surface of the antigen presenting cell.

5.2.3. Heterologous Antigen

The chimeric immunogens of the invention also comprise a heterologous antigen. The antigen is "heterologous" because it is heterologous to a portion of the remainder of the immunogen; i.e., not ordinarily found in a molecule from which one of the other domains of the chimeric immunogen is derived. The heterologous antigen can be any molecule, macromolecule, combination of molecules, etc. against which an immune response is desired. Thus, the heterologous antigen can be any peptide, polypeptide, protein, nucleic acid, lipid, carbohydrate, or small organic molecule, or any combination thereof, against which the skilled artisan wishes to induce an immune response. Preferably, the heterologous antigen is an antigen that is present on a pathogen. More preferably, the heterologous antigen is an antigen that, when administered to a subject as part of a chimeric immunogen, results in an immune response against the heterologous antigen that protects the subject from infection by a pathogen from which the heterologous antigen is derived.

The heterologous antigen can be attached to the remainder of the chimeric immunogen by any method known by one of skill in the art without limitation. In certain, embodiments, the heterologous antigen is expressed together with the remainder of the chimeric immunogen as a fusion protein. In such embodiments, the heterologous antigen can be inserted into or replace any portion of the chimeric immunogen, so long as the receptor binding domain, the translocation domain, and the optional ER retention signal domain retain their activities, and the immune response induced against the heterologous antigen retains specificity. Methods for assessing the specificity of the immune response against the heterologous antigen are extensively described below. The heterologous antigen is preferably inserted into or replaces all or a portion of the Ib loop of PE, into the ER retention domain, or attached to or near the C-terminal end of the translocation domain.

In native PE, the Ib loop (domain Ib) spans amino acids 365 to 399, and is structurally characterized by a disulfide bond between two cysteines at positions 372 and 379. This portion of PE is not essential for any known activity of PE, including cell binding, translocation, ER retention or ADP ribosylation activity. Accordingly, domain Ib can be deleted entirely, or modified to contain a heterologous antigen.

Thus, in certain embodiments, the heterologous antigen can be inserted into domain Ib. If desirable, the heterologous antigen can be inserted into domain Ib wherein the cysteines at positions 372 and 379 are not crosslinked. This can be accomplished by reducing the disulfide linkage between the cysteines, by deleting one or both of the cysteines entirely from the Ib domain, by mutating one or both of the cysteines to other residues, such as, for example, serine, or by other similar techniques. Alternatively, the heterologous antigen can be inserted into the Ib loop between the cysteines at positions 372 and 379. In such embodiments, the disulfide linkage between the cysteines can be used to constrain the heterologous antigen domain.

This arrangement offers several advantages. The chimeric immunogens can be used in this manner to present heterologous antigens that naturally comprise a cysteine-cysteine disulfide bond in native or near-native conformation. Further, without intending to be bound to any particular theory or mechanism of action, it is believed that charged amino acid residues in the native Ib domain result in a hydrophilic structure that protrudes from the molecule and into the solvent. Thus, inserting the heterologous antigen into the Ib loop gives immune system components unfettered access to the antigen, resulting in more effective antigen presentation. Such access is particularly useful the heterologous antigen is a B cell antigen for inducing a humoral immune responses. Further, changes, including mutations or insertions, to domain Ib do not appear to affect activity of the other PE domains. Accordingly, although native Ib domain has only six amino acids between the cysteine residues, much longer sequences can be inserted into the loop without disrupting the other functions of the chimeric immunogen.

In other embodiments, the heterologous antigen can be inserted into the optional ER retention domain of the chimeric immunogen. Without intending to be bound to any particular theory or mechanism of action, it is believed that the nature of the immune response against the heterologous antigen varies depending on the degree of separation between the antigen and the ER retention signal. In particular, the degree to which the heterologous antigen is processed by the Class I or II MHC pathways can vary depending on this degree of separation. By placing the heterologous antigen close to the ER retention signal, e.g., inserting the heterologous antigen into the ER retention domain of the chimeric immunogen near the ER retention signal, more of the heterologous antigen can be directed into the Class I MHC processing pathway thereby inducing a cellular immune response. Conversely, when the heterologous antigen is further from the ER retention signal, more of the antigen is directed into the Class II MHC processing pathway, thereby facilitating induction of a humoral immune response. If the immune response is intended to be primarily humoral, with essentially no Class I MHC cell mediated response, the ER retention domain can be deleted entirely, and the heterologous antigen attached to the immunogen in another location, such as, for example, to the C terminus of the translocation domain. Thus, by controlling the spatial relationship between the heterologous antigen and the ER retention signal, the skilled artisan can modulate the immune response that is induced against the heterologous antigen.

In embodiments where the heterologous antigen is expressed together with another portion of the chimeric immunogen as a fusion protein, the heterologous antigen can be can be inserted into the chimeric immunogen by any method known to one of skill in the art without limitation. For example, amino acids corresponding to the heterologous antigen can be directly into the chimeric immunogen, with or without deletion of native amino acid sequences. In certain embodiments, all or part of the Ib domain of PE can be deleted and replaced with the heterologous antigen. In certain embodiments, the cysteine residues of the Ib loop are deleted so that the heterologous antigen remains unconstrained. In other embodiments, the cysteine residues of the Ib loop are linked with a disulfide bond and constrain the heterologous antigen.

In embodiments where the heterologous antigen is not expressed together with the remainder of the chimeric immunogen as a fusion protein, the heterologous antigen can be connected with the remainder of the chimeric immunogen by any suitable method known by one of skill in the art, without limitation. More specifically, the exemplary methods described above for connecting a receptor binding domain to the remainder of the molecule are equally applicable for connecting the heterologous antigen to the remainder of the molecule.

In certain embodiments, the heterologous antigen is a peptide, polypeptide, or protein. The heterologous antigen can be any peptide, polypeptide, or protein against which an immune response is desired to be induced. In certain embodiments, the heterologous antigen is a peptide that comprises about 5, about 8, about 10, about 12, about 15, about 17, about 20, about 25, about 30, about 40, about 50, or about 60, about 70, about 80, about 90, about 100, about 200, about 400, about 600, about 800, or about 1000 amino acids. In certain embodiments, the heterologous antigen is a polypeptide derived from *Pseudomonas aeruginosa*. In certain embodiments, the heterologous antigen is *Pseudomonas* pilin protein, or a portion thereof. In further embodiments, the heterologous antigen is a peptide derived from *Pseudomonas* pilin protein. In certain embodiments, the peptide derived from *Pseudomonas* pilin peptide is not a peptide that is amino acid residues 128-144 of a type IV pilin protein. In certain embodiments, the peptide derived from *Pseudomonas* pilin peptide does not have an amino acid sequence that is KCTSDQDEQFIPKGCSK (SEQ ID NO.:7). In a preferred embodiment, the heterologous antigen is a peptide that has an amino acid sequence that is TAADGLWKCTSDQDEQFIPKGCSK (SEQ ID NO.:1.)

In certain embodiments, the heterologous antigen is a carbohydrate. The heterologous antigen can be any carbohydrate against which an immune response is desired to be induced. In certain embodiments, the heterologous antigen is a carbohydrate that comprises about 1, about 2, about 3, about 4, about 5, about 8, about 10, about 12, about 15, about 17, about 20, about 25, about 30, about 40, about 50, or about 60, about 70, about 80, about 90, or about 100 sugar monomers. In certain embodiments, the heterologous antigen is a carbohydrate derived from *Pseudomonas aeruginosa*.

In other embodiments, the heterologous antigen can be a glycoprotein, or a portion thereof. The heterologous antigen can be any glycoprotein, or portion of a glycoprotein, against which an immune response is desired to be induced. In certain embodiments, the heterologous antigen is a glycoprotein or glycoprotein portion that comprises about 5, about 8, about 10, about 12, about 15, about 17, about 20, about 25, about 30, about 40, about 50, or about 60, about 70, about 80, about 90, about 100, about 200, about 400, about 600, about 800, or about 1000 amino acids. In certain embodiments, the heterologous antigen is a glycoprotein or glycoprotein portion derived from *Pseudomonas aeruginosa*.

In addition to the protein component, the glycoprotein or glycoprotein portion also comprises a carbohydrate moiety. The carbohydrate moiety of the glycoprotein or glycoprotein portion comprises about 1, about 2, about 3, about 4, about 5, about 8, about 10, about 12, about 15, about 17, about 20, about 25, about 30, about 40, about 50, or about 60, about 70, about 80, about 90, or about 100 sugar monomers.

In general, the skilled artisan may select the heterologous antigen at her discretion, guided by the following discussion. One important factor in selecting the heterologous antigen is the type of immune response that is to be induced. For example, when a humoral immune response is desired, the heterologous antigen should be selected to be recognizable by a B-cell receptor and to be antigenically similar to a region of the source molecule that is available for antibody binding.

Important factors to consider when selecting a B-cell antigen include, but are not limited to, the size and conformation of the antigenic determinant to be recognized, both in the context of the chimeric immunogen and in the native molecule from which the heterologous antigen is derived; the hydrophobicity or hydrophilicity of the heterologous antigen; the topographical accessibility of the antigen in the native molecule from which the heterologous antigen is derived; and the flexibility or mobility of the portion of the native molecule from which the heterologous antigen is derived. See, e.g., Kuby, 1997, *Immunology Chapter* 4, W.H. Freeman and Company, New York. Based on these criteria, the skilled artisan can, when appropriate, select a portion of a large molecule, such as a protein, to be the heterologous antigen. If the source of the heterologous antigen cannot be effectively represented by selecting a portion of it, then the skilled artisan can select the entire molecule to be the heterologous antigen. Such embodiments are particularly useful in the cases of B-cell antigens that are formed by non-sequential amino acids, i.e., antigens formed by amino acids that are not adjacent in the primary structure of the source protein.

Similarly, if the skilled artisan wishes to deliver a heterologous antigen to activate T cells, several factors must be considered in the selection of the heterologous antigen. Principle among such factors is whether helper T cells or cytotoxic T cells are to be stimulated. As described below, helper T cells recognize antigen presented by Class II MHC molecules, while cytotoxic T cells recognize antigen present by Class I MHC. Accordingly, in order to selectively activate these populations, the skilled artisan should select the heterologous antigen to be presentable by the appropriate type of MHC. For example, the skilled artisan can select the heterologous antigen to be a peptide that is presented by Class I MHC when a response mediated by cytotoxic T cells is desired. Similarly, the skilled artisan can select the heterologous antigen to be a peptide that is presented by Class II MHC when a response mediated by helper T cells is desired.

Further, both Class I and Class II MHC exhibit significant allelic variation in studied populations. Much is known about Class I and II MHC alleles and the effects of allelic variation on antigens that can be presented by the different alleles. For example, rules for interactions between Class I MHC haplotype and antigens that can be effectively presented by these molecules are reviewed in Stevanovic, 2002, *Transpl Immunol* 10:133-136. Further guidance on selection of appropriate peptide antigens for Class I and II MHC molecules may be found in U.S. Pat. Nos. 5,824,315 and 5,747,269, and in Germain et al., 1993, *Annu. Rev. Immunol.* 11:403-450; Sinigaglia et al., 1994, *Curr. Opin. Immunol.* 6:52-56; Margalit et al., 2003, *Novartis Found Symp.* 254:77-101, 216-22, and 250-252; Takahashi, 2003, *Comp Immunol Microbiol Infect Dis.* 26:309-328; Yang, 2003, *Microbes Infect.* 5:39-47; and Browning et al., 1996, *HLA and MHC: Genes, Molecules and Function* (Davenport and Hill, eds.) A BIOS Scientific Publishers, Oxford. An empirical system for identifying peptide antigens for presentation on Class II MHC, and that can be adapted for identifying peptide antigens for presentation on Class I MHC, is presented in U.S. Pat. No. 6,500,641.

Further, the chimeric immunogen can comprise one or more antigens in addition to the antigen from *Pseudomonas* pilin protein that can be a molecule that potentiates an immune response. Any antigen that can act as immune stimulant known by one of skill in the art without limitation can be used as an antigen in such embodiments. For example, the heterologous antigen can be a nucleic acid with an unmethylated CpG motif, with a methylated CpG motif, or without any CpG motifs, as described in U.S. Pat. Nos. 6,653,292 and 6,239,116 and Published U.S. Application 20040152649, lipopolysaccharide (LPS) or an LPS derivative such as mono- or diphosphoryl lipid A, or any of the LPS derivatives or other adjuvants described in U.S. Pat. Nos. 6,716,623, 6,720,146, and 6,759,241.

5.2.4. Endoplasmic Reticulum Retention Domain

The chimeric immunogens of the invention can optionally comprise an endoplasmic reticulum retention domain. This domain comprises an endoplasmic reticulum signal sequence, which functions in translocating the chimeric immunogen from the endosome to the endoplasmic reticulum, and from thence into the cytosol. Native PE comprises an ER retention domain in domain III. The ER retention domain comprises an ER retention signal sequence at its carboxy terminus. In native PE, this ER retention signal is REDLK (SEQ ID NO.:8). The terminal lysine can be eliminated (i.e., REDL (SEQ ID NO.:2)) without an appreciable decrease in activity. However, any ER retention signal sequence known to one of skill in the art without limitation can be used in the chimeric immunogens of the invention. Other suitable ER retention signal sequences include, but are not limited to, KDEL (SEQ ID NO.:3), or dimers or multimers of these sequences. See Ogata et al., 1990, *J. Biol. Chem.* 265:20678-85; U.S. Pat. No. 5,458,878; and Pastan et al., 1992, *Annu. Rev. Biochem.* 61:331-54.

In certain embodiments, the chimeric immunogen comprises domain III of native PE, or a portion thereof. Preferably, the chimeric immunogen comprises domain III of ΔE553 PE. In certain embodiments, domain III, including the ER retention signal, can be entirely eliminated from the chimeric immunogen. In other embodiments, the chimeric immunogen comprises an ER retention signal sequence and comprises a portion or none of the remainder of PE domain III. In certain embodiments, the portion of PE domain III other than the ER retention signal can be replaced by another amino acid sequence. This amino acid sequence can itself be non immunogenic, slightly immunogenic, or highly immunogenic. A highly immunogenic ER retention domain is preferable for use in eliciting a humoral immune response. For example, PE domain III is itself highly immunogenic and can be used in chimeric immunogens where a robust humoral immune response is desired. Chimeras in which the ER retention domain is only slightly immunogenic will be more useful when an Class I MHC-dependent cell-mediated immune response is desired.

ER retention domain activity can routinely be assessed by those of skill in the art by testing for translocation of the protein into the target cell cytosol using the assays described below.

In native PE, the ER retention sequence is located at the C-terminus of domain III. Native PE domain III has at least two observable activities. Domain III mediates ADP-ribosylation and therefore toxicity. Further, the ER retention signal present at the C-terminus directs endocytosed toxin into the endoplasmic reticulum and from thence, into the cytosol. Eliminating the ER retention sequence from the chimeric immunogens does not alter the activity of *Pseudomonas* exotoxin as a superantigen, but does prevent it from eliciting an MHC Class I-dependent cell-mediated immune response.

The PE domain that mediates ADP-ribosylation is located between about amino acids 400 and 600 of PE. This toxic activity of native PE is preferably eliminated in the chimeric immunogens of the invention. By doing so, the chimeric immunogen can be used as a vehicle for delivering heterologous antigens to be processed by the cell and presented on the cell surface with MHC Class I or Class II molecules, as desired, rather than as a toxin. ADP ribosylation activity can be eliminated by, for example, deleting amino acid E553. See, e.g., Lukac et al., 1988, *Infect. and Immun.* 56:3095-3098. Alternatively, the amino acid sequence of domain III, or portions of it, can be deleted from the protein. Of course, an ER retention sequence should be included at the C-terminus if a Class I MHC-mediated immune response is to be induced.

In certain embodiments, the ER retention domain is substantially identical to the native amino acid sequences of PE domain III, or a fragment thereof. In certain embodiments, the ER retention domain is domain III of PE. In other embodiments, the ER retention domain is domain III of ΔE553 PE. In still other embodiments, the ER retention domain comprises an amino acid sequence that is selected from the group consisting of RDELK, RDEL, and KDEL.

5.3. Methods for Inducing an Immune Response

In another aspect, the invention provides methods of inducing an immune response against an antigen. The methods allow one of skill in the art to induce a cellular, humoral, or secretory immune response. These methods generally rely on administration of a chimeric immunogen of the invention to a subject in whom the immune response is to be induced. As described above, the chimeric immunogens can be used to induce an immune response that is specific for a heterologous antigen. In certain embodiments, the immune response that is induced is a prophylactic immune response, i.e., the subject is not already afflicted with a disease from which the heterologous antigen is derived. In other embodiments, the immune response that is induced is therapeutic, i.e., the subject is already afflicted with a disease from which the heterologous antigen is derived.

Accordingly, the invention provides methods for inducing an immune response against a heterologous antigen. In certain embodiments, the methods comprise administering to a subject in whom the immune response is to be induced a chimeric immunogen bearing the heterologous antigen. The chimeric immunogen can be administered as a vaccine composition, as described below. The resultant immune responses protect against infection by a pathogen bearing the heterologous antigen or against cells that express the heterologous antigen. For example, if the pathology results from bacterial or parasitic protozoan infection, the immune response is mounted against the pathogens, themselves. If the pathogen is a virus, infected cells will express the heterologous antigens on their surface and become the target of a cell mediated immune response, though there can also be an immune response mounted against viral particles. Aberrant cells, such as cancer cells, that express antigens not present on the surface of normal cells also can be subject to a cell mediated immune response.

Accordingly, in certain aspects, the invention provides a method for inducing an immune response in a subject that comprises administering to the subject an effective amount of a chimeric immunogen comprising a receptor binding domain, a translocation domain, and a *Pseudomonas* pilin peptide that comprises an amino acid sequence that is TAADGLWKCTSDQDEQFIPKGCSK (SEQ ID NO.:1). In certain embodiments, administration of the chimeric immunogen induces an immune response in the subject that is effective to reduce adherence of a microorganism expressing the *Pseudomonas* pilin peptide to epithelial cells of the subject when the chimeric immunogen is administered to the subject. In certain embodiments, administration of the chimeric immunogen to the subject induces an immune response in the subject that reduces cytotoxicity of *Pseudomonas* exotoxin A.

In certain embodiments, the subject is a human. In certain embodiments, the chimeric immunogen is administered to said subject nasally or orally.

In certain embodiments, the chimeric immunogen is administered in the form of a pharmaceutical composition that comprises the chimeric immunogen and a pharmaceutically acceptable diluent, excipient, vehicle, or carrier. In certain embodiments, the pharmaceutical composition is formulated for nasal or oral administration.

In other embodiments, the invention provides a method for generating in a subject antibodies specific for a *Pseudomonas* pilin peptide having an amino acid sequence that is TAADGLWKCTSDQDEQFIPKGCSK (SEQ ID NO.:1). The method comprises administering to the subject an effective amount of a chimeric immunogen that comprises a receptor binding domain, a translocation domain, and a *Pseudomonas* pilin peptide that comprises an amino acid sequence that is TAADGLWKCTSDQDEQFIPKGCSK (SEQ ID NO.:1). Administration of such chimeric immunogens generates antibodies specific for the *Pseudomonas* pilin peptide. In certain embodiments, administration of the chimeric immunogen to the subject induces an immune response in the subject that reduces the cytotoxicity of *Pseudomonas* exotoxin A.

In certain embodiments, the subject is a mammal. In further embodiments, the subject is a rodent, lagomorph or primate. In a preferred embodiments, the subject is a human.

5.3.1. Humoral Immune Responses

In certain embodiments, the invention provides a method for inducing a humoral immune response against the heterologous antigen in a subject. The methods generally comprise administering to a subject a chimeric immunogen that is configured to produce a humoral immune response. Such immune responses generally involve the production of antibodies specific for the antigen. Certain embodiments of the chimeric immunogens have properties that allow the skilled artisan to induce a humoral immune response against the heterologous antigens. For example, when the heterologous antigen is inserted into PE domain Ib, the flanking cysteines cause the heterologous antigen to be extended from the remainder of the immunogen and facilitate recognition of the antigen by a B cell through an interaction with a B-cell receptor. Interaction between the heterologous antigen and the B cell receptor stimulates clonal expansion of the B cell bearing the receptor, eventually resulting in a population of plasma cells that secrete antibodies specific for the antigen.

In most circumstances, B cell recognition of antigen is necessary, but not sufficient, to induce a robust humoral immune response. The humoral response is greatly potentiated by CD4+ (helper) T cell signaling to B cells primed by antigen recognition. Helper T cells are activated to provide such signals to B cells by recognition of antigen processed through the Class II MHC pathway. The antigen recognized by the T cell can, but need not, be the same antigen recognized by the B cell. The chimeric immunogens of the invention can be targeted to such antigen presenting cells for processing in the Class II MHC pathway in order to stimulate helper T cells to activate B cells. By doing so, the chimeric immunogens can be used to stimulate a robust humoral immune response that is specific for the heterologous antigen.

Further, the chimeric immunogens are attractive vehicles for inducing a humoral immune response against heterologous antigens that are constrained within their native environment. By inserting the heterologous antigen into the Ib loop of PE antigens, the antigen can be presented to immune cells in near-native conformation. The resulting antibodies generally recognize the native antigen better than those raised against unconstrained versions of the heterologous antigen. The Ib loop can also be used to present B cell antigens that are not constrained in their native environment. In such embodiments, the antigen inserted into the Ib loop should be flanked by a sufficient number of amino acids that give conformational flexibility, such as, e.g., glycine, serine, etc., to allow the antigen to fold into its native form and avoid constraint by the disulfide linkage between the cysteines of the Ib loop.

The humoral immune response induced by the chimeric immunogens can be assessed using any method known by one of skill in the art without limitation. For example, an animal's immune response against the heterologous antigen can be monitored by taking test bleeds and determining the titer of antibody reactivity to the heterologous antigen. When appropriately high titers of antibody to the heterologous antigen are obtained, blood can be collected from the animal and antisera prepared. The antisera can be further enriched for antibodies reactive to the heterologous antigen, when desired. See, e.g., Coligan, 1991, *Current Protocols in Immunology*, Greene Publishing Associates and Wiley Interscience, NY; and Harlow and Lane, 1989, *Antibodies: A Laboratory Manual*, Cold Spring Harbor Press, NY.

Antibodies produced in response to administration of the chimeric immunogens can then be used for any purpose known by one of skill in the art, without limitation. The antibodies are believed to be equivalent to antibodies induced using conventional techniques, such as coupling peptides to an immunogen. For example, the antibodies can be used to make monoclonal antibodies, humanized antibodies, chimeric antibodies or antibody fragments. Techniques for producing such antibody derivatives may be found in, for example, Stites et al. eds., 1997, *Medical Immunology* (9th ed.), McGraw-Hill/Appleton & Lange, CA; Harlow and Lane, 1989, *Antibodies: A Laboratory Manual*, Cold Spring Harbor Press, NY; Goding, 1986, *Monoclonal Antibodies: Principles and Practice* (2d ed.), Academic Press, NY; Kohler and Milstein, 1975, *Nature* 256: 495-497; and U.S. Pat. No. 5,585,089.

5.3.2. Cell-Mediated Immune Responses

In other embodiments, the invention provides methods for eliciting a cell-mediated immune response against cells expressing the heterologous antigen. The methods generally comprise administering to a subject a chimeric immunogen that comprises the heterologous antigen that is configured to produce a cell-mediated immune response. Such immune responses generally involve the activation of cytotoxic T lymphocytes that can recognize and kill cells that display the antigen on their surfaces. However, certain aspects of humoral immune responses give rise to cell-mediated effects as well, as described below. Certain embodiments of the chimeric immunogens have properties that allow the skilled artisan to induce a cell-mediated immune response against the heterologous antigens.

In particular, heterologous antigens that are inserted into a chimeric immunogen near a ER retention signal tend to induce a cell-mediated immune response. Without intending to be bound to any particular theory or mechanism of action, it is believed that the ER retention signal causes the chimeric immunogen to be trafficked from an endosome to the ER, and from thence into the cytosol. Once in the cytosol, peptides from the immunogen, including the heterologous antigen, enter the Class I MHC processing pathway. The peptides associate with Class I MHC and are presented on the surface of the cell into which the immunogen has been introduced. CD8+ (cytotoxic) T lymphocytes then recognize the heterologous antigen in association with Class I MHC and thereby become activated and primed to kill cells that similarly have the heterologous antigen associated with Class I MHC on their surfaces.

Part of the processing that occurs during presentation on Class I MHC is believed to result in degradation of the chimeric immunogen into peptides that can associate with the MHC molecule. This proteolysis is believed to begin in the endosome and to continue in the cytosol. If, in the course of this process, the heterologous antigen is separated from the ER retention signal before the heterologous antigen is trafficked to the cytosol, it is believed that the heterologous antigen cannot associate with Class I MHC. In such circumstances, the heterologous antigen can remain in the endosome, and can be directed to the Class II MHC processing pathway. Accordingly, it is believed that the distance, e.g., the number of amino acids, between the heterologous antigen and the ER retention signal can affect the degree to which the antigen is presented in association with Class I or Class II MHC.

Features of peptides that associate with the various allelic forms of Class I MHC have been well characterized. For example, peptides bound by HLA-A1 generally comprise a first conserved residue of T, S or M, a second conserved residue of D or E, and a third conserved residue of Y, wherein the first and second residues are adjacent, and both are separated from the third residue by six or seven amino acids. Peptides that bind to other alleles of Class I MHC have also been characterized. Using this knowledge, the skilled artisan can select heterologous antigens that can associate with a Class I MHC allele that is expressed in the subject. By administering chimeric immunogens comprising such antigens near the ER retention signal, a cell-mediated immune response can be induced.

Cell-mediated immune responses can also arise as a consequence of humoral immune responses. Antibodies produced in the course of the humoral immune response bind to their cognate antigen; if this antigen is present on the surface of a cell, the antibody binds to the cell surface. Cells bound by antibodies in this manner are subject to antibody-dependent cell-mediated cytotoxicity, in which immune cells that bear Fc receptors attack the marked cells. For example, natural killer cells and macrophages have Fc receptors and can participate in this phenomenon.

5.3.3. Secretory Immune Response

In other embodiments, the invention provides methods for eliciting a secretory immune response against the heterologous antigen. The methods generally comprise administering to a mucous membrane of the subject a chimeric immunogen that comprises the heterologous antigen that is configured to bind to a receptor present on the mucous membrane. The mucous membrane can be any mucous membrane known by one of skill in the art to be present in the subject, without limitation. For example, the mucous membrane can be present in the eye, nose, mouth, trachea, lungs, esophagus, stomach, small intestine, large intestine, rectum, anus, sweat glands, vulva, vagina, or penis of the subject. Certain embodiments of the chimeric immunogens have properties that allow the skilled artisan to induce a secretory immune response against the heterologous antigens.

In particular, chimeric immunogens that comprise receptor binding domains that can bind to a receptor present on the apical membrane of an epithelial cell can be used to induce a secretory immune response. Such receptor binding domains are extensively described above. Without intending to be bound by any particular theory or mechanism of action, it is believed that the original encounter with the antigen at the mucosal surface directs the immune system to produce a secretory rather than humoral immune response.

Secretory immune responses are desirable for protecting against any pathogen that enters the body through a mucous membrane. Mucous membranes are primary entryways for many infectious pathogens, including, for example, HIV, herpes, vaccinia, cytomegalovirus, *yersinia, vibrio*, and *Pseudomonas* spp. Mucous membranes can be found in the mouth, nose, throat, lung, vagina, rectum and colon. As one defense against entry by these pathogens, the body secretes secretory IgA from mucosal epithelial membranes that can bind the pathogens and prevent or deter pathogenesis. Furthermore, antigens presented at one mucosal surface can trigger responses at other mucosal surfaces due to trafficking of antibody-secreting cells between the mucous membranes. The structure of secretory IgA appears to be crucial for its sustained residence and effective function at the luminal surface of a mucous membrane. "Secretory IgA" or "sIgA" generally refers to a polymeric molecule comprising two IgA immunoglobulins joined by a J chain and further bound to a secretory component. While mucosal administration of antigens can generate an IgG response, parenteral administration of immunogens rarely produces strong sIgA responses.

The chimeric immunogens can be administered to the mucous membrane of the subject by any suitable method or in any suitable formulation known to one of skill in the art without limitation. For example, the chimeric immunogens can be administered in the form of liquids or solids, e.g., sprays, ointments, suppositories or erodible polymers impregnated with the immunogen. Administration can involve applying the immunogen to a one or more different mucosal surfaces. Further, in certain embodiments, the chimeric immunogen can be administered in a single dose. In other embodiments, the chimeric immunogen can be administered in a series of two or more administrations. In certain embodiments, the second or subsequent administration of the chimeric immunogen is administered parenterally, e.g., subcutaneously or intramuscularly.

The sIgA response is strongest on mucosal surfaces exposed to the immunogen. Therefore, in certain embodiment, the immunogen is applied to a mucosal surface that is likely to be a site of exposure to the pathogen. Accordingly, chimeric immunogens against pathogens encountered on vaginal, anal, or oral mucous membranes are preferably administered to vaginal, anal or oral mucosal surfaces, respectively. However, nasal administration of the chimeric immunogens can also induce robust secretory immune responses from other mucous membranes. See, for example, Boyaka et al., 2003, *Cur. Pharm. Des.* 9:1965-1972.

Mucosal administration of the chimeric immunogens of this invention result in strong memory responses, both for IgA and IgG. These memory responses can advantageously be boosted by re-administering the chimeric immunogen after a period of time. Such booster administrations can be administered either mucosally or parenterally. The memory response can be elicited by administering a booster dose more than a year after the initial dose. For example, a booster dose can be administered about 12, about 16, about 20 or about 24 months after the initial dose.

5.4. Polynucleotides Encoding Chimeric Immunogens

In another aspect, the invention provides polynucleotides comprising a nucleotide sequence encoding a chimeric immunogen of the invention. These polynucleotides are useful, for example, for making the chimeric immunogens. In yet another aspect, the invention provides an expression system that comprises a recombinant polynucleotide sequence encoding a receptor binding domain, a translocation domain, an optional ER retention domain, and an insertion site for a polynucleotide sequence encoding a heterologous antigen. The insertion site can be anywhere in the polynucleotide sequence so long as the insertion does not disrupt the receptor binding domain, the translocation domain, or the optional ER retention domain. Preferably, the insertion site is between the translocation domain and the ER retention domain. In other equally preferred embodiments, the insertion site is in the ER retention domain.

In certain embodiments, the recombinant polynucleotides are based on polynucleotides encoding PE, or portions or derivatives thereof. In other embodiments, the recombinant polynucleotides are based on polynucleotides that hybridize to a polynucleotide that encodes PE under stringent hybridization conditions. A nucleotide sequence encoding PE is presented as SEQ ID NO.:9. This sequence can be used to prepare PCR primers for isolating a nucleic acid that encodes any portion of this sequence that is desired. For example, PCR can be used to isolate a nucleic acid that encodes one or more of the functional domains of PE. A nucleic acid so isolated can then be joined to nucleic acids encoding other functional domains of the chimeric immunogens using standard recombinant techniques.

Other in vitro methods that can be used to prepare a polynucleotide encoding PE, PE domains, or any other functional domain useful in the chimeric immunogens of the invention include, but are not limited to, reverse transcription, the polymerase chain reaction (PCR), the ligase chain reaction (LCR), the transcription-based amplification system (TAS), the self-sustained sequence replication system (3SR) and the QP replicase amplification system (QB). Any such technique known by one of skill in the art to be useful in construction of recombinant nucleic acids can be used. For example, a polynucleotide encoding the protein or a portion thereof can be isolated by polymerase chain reaction of cDNA using primers based on the DNA sequence of PE or another polynucleotide encoding a receptor binding domain.

Guidance for using these cloning and in vitro amplification methodologies are described in, for example, U.S. Pat. No. 4,683,195; Mullis et al., 1987, *Cold Spring Harbor Symp. Quant. Biol.* 51:263; and Erlich, ed., 1989, *PCR Technology*, Stockton Press, NY. Polynucleotides encoding a chimeric immunogen or a portion thereof also can be isolated by screening genomic or cDNA libraries with probes selected from the sequences of the desired polynucleotide under stringent, moderately stringent, or highly stringent hybridization conditions.

Construction of nucleic acids encoding the chimeric immunogens of the invention can be facilitated by introducing an insertion site for a nucleic acid encoding the heterologous antigen into the construct. In certain embodiments, an insertion site for the heterologous antigen can be introduced between the nucleotides encoding the cysteine residues of domain Ib. In other embodiments, the insertion site can be introduced anywhere in the nucleic acid encoding the immunogen so long as the insertion does not disrupt the functional domains encoded thereby. In certain embodiments, the insertion site can be in the ER retention domain. In certain embodiments, the insertion site is introduced into the nucleic acid encoding the chimeric immunogen. In other embodiments, the nucleic acid comprising the insertion site can replace a portion of the nucleic acid encoding the immunogen, as long s the replacement does not disrupt the receptor binding domain or the translocation domain.

In more specific embodiments, the insertion site comprises that includes a cloning site cleaved by a restriction enzyme. In certain embodiments, the cloning site can be recognized and cleaved by a single restriction enzyme, for example, by PstI. In such examples, a polynucleotide encoding heterologous antigen that is flanked by PstI sequences can be inserted into the vector. In other embodiments, the insertion site comprises a polylinker that comprises about one, about two, about three, about four, about five, about ten, about twenty or more cloning sites, each of which can be cleaved by one or more restriction enzymes.

Further, the polynucleotides can also encode a secretory sequence at the amino terminus of the encoded chimeric immunogen. Such constructs are useful for producing the chimeric immunogens in mammalian cells as they simplify isolation of the immunogen.

Furthermore, the polynucleotides of the invention also encompass derivative versions of polynucleotides encoding a chimeric immunogen. Such derivatives can be made by any method known by one of skill in the art without limitation. For example, derivatives can be made by site-specific mutagenesis, including substitution, insertion, or deletion of one, two, three, five, ten or more nucleotides, of polynucleotides encoding the chimeric immunogen. Alternatively, derivatives can be made by random mutagenesis. One method for randomly mutagenizing a nucleic acid comprises amplifying the nucleic acid in a PCR reaction in the presence of 0.1 mM $MnCl_2$ and unbalanced nucleotide concentrations. These conditions increase the misincorporation rate of the polymerase used in the PCR reaction and result in random mutagenesis of the amplified nucleic acid.

Several site-specific mutations and deletions in chimeric molecules derived from PE have been made and characterized. For example, deletion of nucleotides encoding amino acids 1-252 of PE yields a construct referred to as "PE40." Deleting nucleotides encoding amino acids 1-279 of PE yields a construct referred to as "PE37." See U.S. Pat. No. 5,602,095. In both of these constructs, the receptor binding domain of PE, i.e., domain Ia, has been deleted. Nucleic acids encoding a receptor binding domain can be ligated to these constructs to produce chimeric immunogens that are targeted to the cell surface receptor recognized by the receptor binding domain. Of course, these constructs are particularly useful for expressing chimeric immunogens that have a receptor binding domain that is not domain Ia of PE. The constructs can optionally encode an amino-terminal methionine to assist in expression of the construct. In certain embodiments, the receptor binding domain can be ligated to the 5' end of the polynucleotide encoding the translocation domain and optional ER retention domain. In other embodiments, the polynucleotide can be inserted into the constructs in the nucleotide sequence encoding the ER retention domain.

Other nucleic acids encoding mutant forms of PE that can be used as a source of nucleic acids for constructing the chimeric immunogens of the invention include, but are not limited to, PEΔ553 and those described in U.S. Pat. Nos. 5,602,095; 5,512,658 and 5,458,878, and in Vasil et al., 1986, Infect. Immunol. 52:538-48.

Accordingly, in certain aspects, the invention provides a polynucleotide that encodes a chimeric immunogen that comprises a receptor binding domain, a translocation domain, and a Pseudomonas pilin peptide that comprises an amino acid sequence that is TAADGLWKCTSDQDEQFIPKGCSK (SEQ ID NO.:1). In certain embodiments, the chimeric immunogen, when administered to a subject, induces an immune response in the subject that is effective to reduce adherence of a microorganism that expresses the Pseudomonas pilin peptide to epithelial cells of the subject. In certain embodiments, the chimeric immunogen, when administered to the subject, generates an immune response in the subject that reduces the cytotoxicity of Pseudomonas exotoxin A.

In certain embodiments, polynucleotide encodes a chimeric immunogen further comprising an endoplasmic reticulum retention domain. In further embodiments, the Pseudomonas pilin peptide is located between the translocation domain and the endoplasmic reticulum retention domain. In certain embodiments, the endoplasmic reticulum retention domain is an enzymatically-inactive domain III of Pseudomonas exotoxin A. In certain embodiments, the enzymatically inactive domain III of Pseudomonas exotoxin A is inactivated by deleting a glutamate at position 553. In certain embodiments, the endoplasmic reticulum retention domain comprises an amino acid sequence that is selected from the group of RDEL (SEQ ID NO.:2) or KDEL (SEQ ID NO.:3) that is sufficiently near the C-terminus of said endoplasmic reticulum retention domain to result in retention of said chimeric immunogen in the endoplasmic reticulum.

In certain embodiments, the polynucleotide encodes a translocation domain that is selected from the group consisting translocation domains from Pseudomonas exotoxin A, diptheria toxin, pertussis toxin, cholera toxin, heat-labile E. coli enterotoxin, shiga toxin, and shiga-like toxin. In certain embodiments, the translocation domain is domain II of Pseudomonas exotoxin A. In further embodiments, the translocation domain comprises amino acids 280 to 364 of domain II of Pseudomonas exotoxin A.

In certain embodiments, the polynucleotide encodes a chimeric immunogen that comprises more than one of the Pseudomonas pilin peptides.

In certain embodiments, the polynucleotide encodes a receptor binding domain that is selected from the group consisting of domain Ia of Pseudomonas exotoxin A; a receptor binding domains from cholera toxin, diptheria toxin, shiga toxin, or shiga-like toxin; a monoclonal antibody, a polyclonal antibody, or a single-chain antibody; TGFα, TGFβ, EGF, PDGF, IGF, or FGF; IL-1, IL-2, IL-3, or IL-6; and MIP-1a, MIP-1b, MCAF, or IL-8. In certain embodiments, the receptor binding domain is domain Ia of Pseudomonas exotoxin A. In further embodiments, the domain Ia of Pseudomonas exotoxin A has an amino acid sequence that is SEQ ID NO.:4.

In certain embodiments, the receptor binding domain binds to α2-macroglobulin receptor, epidermal growth factor receptor, transferrin receptor, interleukin-2 receptor, interleukin-6 receptor, interleukin-8 receptor, Fc receptor, poly-IgG receptor, asialoglycopolypeptide receptor, CD3, CD4, CD8, chemokine receptor, CD25, CD11B, CD11C, CD80, CD86, TNFα receptor, TOLL receptor, M-CSF receptor, GM-CSF receptor, scavenger receptor, or VEGF receptor. In certain embodiments, the receptor binding domain binds to α2-macroglobulin receptor.

In certain embodiments, the polynucleotide encodes a chimeric immunogen that has an amino acid sequence that is SEQ ID NO.:5. In other embodiments, the polynucleotide hybridizes under stringent hybridization conditions to a polynucleotide that encodes a chimeric immunogen has an amino acid sequence that is SEQ ID NO.:5

5.5. Expression Vectors

In still another aspect, the invention provides expression vectors for expressing the chimeric immunogens. Generally, expression vectors are recombinant polynucleotide molecules comprising expression control sequences operatively linked to a nucleotide sequence encoding a polypeptide. Expression vectors can readily be adapted for function in prokaryotes or eukaryotes by inclusion of appropriate promoters, replication sequences, selectable markers, etc. to result in stable transcription and translation of mRNA. Techniques for construction of expression vectors and expression of genes in cells comprising the expression vectors are well known in the art. See, e.g., Sambrook et al., 2001, *Molecular Cloning—A Laboratory Manual*, $3^{rd}$ edition, Cold Spring Harbor Laboratory, Cold Spring Harbor, N.Y., and Ausubel et al., eds., *Current Edition, Current Protocols in Molecular Biology*, Greene Publishing Associates and Wiley Interscience, NY.

Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, a tetracycline-inducible CMV promoter (such as the human immediate-early CMV promoter), and a constitutive CMV promoter.

The expression vectors should contain expression and replication signals compatible with the cell in which the chimeric immunogens are expressed. Expression vectors useful for expressing chimeric immunogens include viral vectors such as retroviruses, adenoviruses and adenoassociated viruses, plasmid vectors, cosmids, and the like. Viral and plasmid vectors are preferred for transfecting the expression vectors into mammalian cells. For example, the expression vector pcDNA1 (INVITROGEN™, San Diego, Calif.), in which the expression control sequence comprises the CMV promoter, provides good rates of transfection and expression into such cells.

The expression vectors can be introduced into the cell for expression of the chimeric immunogens by any method known to one of skill in the art without limitation. Such methods include, but are not limited to, e.g., direct uptake of the molecule by a cell from solution; facilitated uptake through lipofection using, e.g., liposomes or immunoliposomes; particle-mediated transfection; etc. See, e.g., U.S. Pat. No. 5,272,065; Goeddel et al., eds, 1990, *Methods in Enzymology*, vol. 185, Academic Press, Inc., CA; Krieger, 1990, *Gene Transfer and Expression—A Laboratory Manual*, Stockton Press, NY; Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, NY.

The expression vectors can also contain a purification moiety that simplifies isolation of the protein. For example, a polyhistidine moiety of, e.g., six histidine residues, can be incorporated at the amino terminal end of the protein. The polyhistidine moiety allows convenient isolation of the protein in a single step by nickel-chelate chromatography. In certain embodiments, the purification moiety can be cleaved from the remainder of the chimeric immunogen following purification. In other embodiments, the moiety does not interfere with the function of the functional domains of the chimeric immunogen and thus need not be cleaved.

5.6. Cell for Expressing a Chimeric Immunogen

In yet another aspect, the invention provides a cell comprising an expression vector for expression of the chimeric immunogens, or portions thereof. The cell is preferably selected for its ability to express high concentrations of the chimeric immunogen to facilitate purification of the protein. In certain embodiments, the cell is a prokaryotic cell, for example, *E. coli*. As described in the examples, the chimeric immunogens are properly folded and comprise the appropriate disulfide linkages when expressed in *E. coli*.

In other embodiments, the cell is a eukaryotic cell. Useful eukaryotic cells include yeast and mammalian cells. Any mammalian cell known by one of skill in the art to be useful for expressing a recombinant polypeptide, without limitation, can be used to express the chimeric immunogens. For example, Chinese hamster ovary (CHO) cells can be used to express the chimeric immunogens.

5.7. Vaccines Comprising Chimeric Immunogens

In yet another aspect, the invention provides vaccines comprising one or more chimeric immunogens. The vaccines are useful for eliciting a protective immune response against the heterologous antigen, particularly against pathogens or cells bearing the heterologous antigen. A vaccine can include one or a plurality of chimeric immunogens. For example, a vaccine can include chimeric immunogens with heterologous antigens from several circulating strains of a pathogen. As the pathogen changes, additional chimeric immunogens can be constructed that include the altered antigens, for example, from breakthrough viruses.

5.7.1. Vaccine Compositions

The vaccines of the invention can be formulated as compositions. The compositions are generally formulated appropriately for the immediate use intended for the vaccine. For example, if the vaccine is not to be administered immediately, the vaccine can be formulated in a composition suitable for storage. One such composition is a lyophilized preparation of the vaccine together with a suitable stabilizer. Alternatively, the vaccine composition can be formulated for storage in a solution with one or more suitable stabilizers. Any such stabilizer known to one of skill in the art without limitation can be used. For example, stabilizers suitable for lyophilized preparations include, but are not limited to, sugars, salts, surfactants, proteins, chaotropic agents, lipids, and amino acids. Stabilizers suitable for liquid preparations include, but are not limited to, sugars, salts, surfactants, proteins, chaotropic agents, lipids, and amino acids. Specific stabilizers than can be used in the compositions include, but are not limited to, trehalose, serum albumin, phosphatidylcholine, lecithin, and arginine. Other compounds, compositions, and methods for stabilizing a lyophilized or liquid preparation of the delivery constructs may be found, for example, in U.S. Pat. Nos. 6,573,237, 6,525,102, 6,391,296, 6,255,284, 6,133,229, 6,007,791, 5,997,856, and 5,917,021.

Further, the vaccine compositions of the invention can be formulated for administration to a subject. The formulation can be suitable for administration to a nasal, oral, vaginal, rectal, or other mucosal surface. Such vaccine compositions generally comprise one or more chimeric immunogens of the invention and a pharmaceutically acceptable excipient, diluent, carrier, or vehicle. Any such pharmaceutically acceptable excipient, diluent, carrier, or vehicle known to one of skill in the art without limitation can be used. Examples of a suitable excipient, diluent, carrier, or vehicle can be found in *Remington's Pharmaceutical Sciences*, 19*th Ed.* 1995, Mack Publishing Co., Easton.

In certain embodiments, the vaccine compositions comprise about 1, about 5, about 10, about 20, about 30, about 40, or about 50 mM sodium chloride. *Pseudomonas* appears to bind epithelial cells via the pilin-asialo-GM1 interaction more efficiently in environments comprising 100 mM NaCl. By reducing the salt concentration, the chimeric immunogen is believed to be more likely to bind to an epithelial cell through its receptor binding domain rather through a pilin-asialo-GM1 interaction. By increasing the proportion bound via the receptor binding domain, a higher concentration of immunogen is delivered to the bloodstream of the subject.

The vaccine compositions can also include an adjuvant that potentiates an immune response when used in administered in conjunction with the chimeric immunogen. Useful adjuvants, particularly for administration to human subjects, include, but are not limited to, alum, aluminum hydroxide, aluminum phosphate, CpG-containing oligonucleotides (both methylated and unmethylated), bacterial nucleic acids, lipopolysaccharide and lipopolysaccharide derivatives such as monophosphoryl lipid A, oil-in-water emulsions, etc. Other suitable adjuvants are described in Sheikh et al., 2000, *Cur. Opin. Mol. Ther.* 2:37-54. Adjuvants are most useful when the vaccine composition is to be injected rather than administered to a mucosal membrane of the subject. However, certain of the above adjuvants are also known in the art to be useful in compositions to be administered to mucosal surface.

In certain embodiments, the vaccine compositions are formulated for oral administration. In such embodiments, the vaccine compositions are formulated to protect the chimeric immunogen from acid and/or enzymatic degradation in the stomach. Upon passage to the neutral to alkaline environment of the duodenum, the chimeric immunogen then contacts a mucous membrane and is transported across the polarized epithelial membrane. The delivery constructs may be formulated in such compositions by any method known by one of skill in the art, without limitation.

In certain embodiments, the oral formulation comprises a chimeric immunogen and one or more compounds that can protect the chimeric immunogen while it is in the stomach. For example, the protective compound should be able to prevent acid and/or enzymatic hydrolysis of the chimeric immunogen. In certain embodiments, the oral formulation comprises a chimeric immunogen and one or more compounds that can facilitate transit of the immunogen from the stomach to the small intestine. In certain embodiments, the one or more compounds that can protect the chimeric immunogen from degradation in the stomach can also facilitate transit of the immunogen from the stomach to the small intestine. Preferably, the oral formulation comprises one or more compounds that can protect the chimeric immunogen from degradation in the stomach and facilitate transit of the immunogen from the stomach to the small intestine. For example, inclusion of sodium bicarbonate can be useful in facilitating the rapid movement of intra-gastric delivered materials from the stomach to the duodenum as described in Mrsny et al., 1999, *Vaccine* 17:1425-1433.

Other methods for formulating compositions so that the chimeric immunogens can pass through the stomach and contact polarized epithelial membranes in the small intestine include, but are not limited to, enteric-coating technologies as described in DeYoung, 1989, *Int J Pancreatol.* 5 Suppl:31-6, and the methods provided in U.S. Pat. Nos. 6,613,332, 6,174, 529, 6,086,918, 5,922,680, and 5,807,832.

Accordingly, in certain aspects, the invention provides a composition comprising a chimeric immunogen that comprises a receptor binding domain, a translocation domain, and a *Pseudomonas* pilin peptide that has an amino acid sequence that is TAADGLWKCTSDQDEQFIPKGCSK (SEQ ID NO.: 1). In certain embodiments, the chimeric immunogen, when administered to a subject, induces an immune response in the subject that is effective to reduce adherence of a microorganism that expresses the *Pseudomonas* pilin peptide to epithelial cells of the subject. In certain embodiments, the chimeric immunogen, when administered to a subject, induces an immune response in the subject that reduces cytotoxicity of *Pseudomonas* exotoxin A.

In certain embodiments, the composition further comprises a pharmaceutically acceptable diluent, excipient, vehicle, or carrier. In certain embodiments, the composition is formulated for nasal or oral administration.

5.7.2. Dosage

Generally, a pharmaceutically effective amount of the vaccine compositions of the invention is administered to a subject. The skilled artisan can readily determine if the dosage of the vaccine composition is sufficient to elicit an immune response by monitoring the immune response so elicited, as described below. In certain embodiments, an amount of vaccine composition corresponding to between about 1 µg and about 1000 µg of chimeric immunogen is administered. In other embodiments, an amount of vaccine composition corresponding to between about 10 µg and about 500 µg of chimeric immunogen is administered. In still other embodiments, an amount of vaccine composition corresponding to between about 10 µg and about 250 µg of chimeric immunogen is administered. In yet other embodiments, an amount of vaccine composition corresponding to between about 10 µg and about 100 µg of chimeric immunogen is administered. In still other embodiments, an amount of vaccine composition corresponding to about 40 µg of chimeric immunogen is administered. In still other embodiments, an amount of vaccine composition corresponding to about 200 µg of chimeric immunogen is administered. In still other embodiments, an amount of vaccine composition corresponding to about 1000 µg of chimeric immunogen is administered. Preferably, an amount of vaccine composition corresponding to between about 10 µg and about 50 µg of chimeric immunogen is administered. Further guidance on selecting an effective dose of the vaccine compositions may be found, for example, in Rose and Friedman, 1980, *Manual of Clinical Immunology*, American Society for Microbiology, Washington, D.C.

The volume of vaccine composition administered will generally depend on the concentration of chimeric immunogen and the formulation of the composition. In certain embodiments, a unit dose of the vaccine is between about 0.05 ml and about 1 ml, preferably about 0.5 ml. The vaccine compositions can be prepared in dosage forms containing between 1 and 50 doses (e.g., 0.5 ml to 25 ml), more usually between 1 and 10 doses (e.g., 0.5 ml to 5 ml)

The vaccine compositions of the invention can be administered in one dose or in multiple doses. A dose can be followed by one or more doses spaced by about 4 to about 8 weeks, by about 1 to about 3 months, or by about 1 to about 6 months. Additional booster doses can be administered as needed. In certain embodiments, booster doses are administered in about 1 to about 10 years.

5.7.3. Administration of Vaccine Compositions

The vaccine compositions of the invention can be administered to a subject by any method known to one of skill in the art. In certain embodiments, the vaccine compositions are contacted to a mucosal membrane of the subject. In other embodiments, the vaccine compositions are injected into the subject. By selecting one of these methods of administering the vaccine compositions, a skilled artisan can modulate the immune response that is elicited. These methods are described extensively below.

Thus, in certain embodiments, the vaccine compositions are contacted to a mucosal membrane of a subject. Any mucosal membrane known by one of skill in the art, without limitation, can be the target of such administration. For example, the mucosal membrane can be present in the eye, nose, mouth, lungs, esophagus, stomach, small intestine, large intestine, rectum, anus, vagina, or penis of the subject. Preferably, the mucosal membrane is a nasal mucous membrane.

In other embodiments, the vaccine composition is delivered by injection. The vaccine composition can be injected subcutaneously or intramuscularly. In such embodiments, the vaccine composition preferably comprises an adjuvant, as described above.

5.7.4. Kits Comprising Vaccine Compositions

In yet another aspect, the invention provides a kit comprising a vaccine composition of the invention. In certain embodiments, the kit further comprises instructions directing a medical professional to administer the vaccine composition to a subject to be vaccinated. In further embodiments, the instructions direct the medical professional to administer the vaccine composition of a mucous membrane of the subject to be vaccinated.

5.8. Making and Testing the Chimeric Immunogens

The chimeric immunogens of the invention are preferably produced recombinantly, as described below. However, the chimeric immunogens may also be produced by chemical synthesis using methods known to those of skill in the art. Alternatively, the chimeric immunogens can be produced using a combination of recombinant and synthetic methods.

5.8.1. Manufacture of Chimeric Immunogens

Methods for expressing and purifying the chimeric immunogens of the invention are described extensively in the examples below. Generally, the methods comprise introducing an expression vector encoding the chimeric immunogen into a cell that can express the chimeric immunogen from the vector. The chimeric immunogen can then be purified for administration to a subject following expression of the immunogen.

5.8.2. Verification of Chimeric Immunogens

Having selected the domains of the chimeric immunogen, the function of these domains, and of the chimeric immunogens as a whole, can routinely be tested to ensure that the immunogens can induce the desired immune response. For example, the chimeric immunogens can be tested for cell recognition, cytosolic translocation and immunogenicity using routine assays. The entire chimeric protein can be tested, or, the function of various domains can be tested by substituting them for native domains of the wild-type toxin.

5.8.2.1. Receptor Binding/Cell Recognition

Receptor binding domain function can be tested by monitoring the chimeric immunogen's ability to bind to the target receptor. Such testing can be accomplished using cell-based assays, with the target receptor present on a cell surface, or in cell-free assays. For example, chimeric immunogen binding to a target can be assessed with affinity chromatography. The chimera can be attached to a matrix in an affinity column, and binding of the receptor to the matrix detected, or vice versa. Alternatively, if antibodies have been identified that bind to either the receptor binding domain or its cognate receptor, the antibodies can be used, for example, to detect the receptor binding domain in the chimeric immunogen by immunoassay, or in a competition assay for the cognate receptor. An exemplary cell-based assay that detects chimeric immunogen binding to receptors on cells comprises labeling the chimera and detecting its binding to cells by, e.g., fluorescent cell sorting, autoradiography, etc.

5.8.2.2. Translocation

The function of the translocation domain can be tested as a function of the chimeric immunogen's ability to gain access to the interior of a cell. Because access first requires binding to the cell, these assays can also be used to assess the function of the cell recognition domain.

The chimeric immunogen's ability to enter the cell can be assessed, for example, by detecting the physical presence of the chimera in the interior of the cell. For example, the chimeric immunogen can be labeled with, for example, a fluorescent marker, and the chimeric immunogen exposed to the cell. Then, the cells can be washed, removing any chimeric immunogen that has not entered the cell, and the amount of label remaining determined. Detecting the label in this fraction indicates that the chimeric immunogen has entered the cell.

5.8.2.3. ER Retention and Translocation to the Cytosol

A related assay can be used to assess the ability of the chimeric immunogen to traffic to the ER and from there into the cytosol of a cell. In such assays, the chimeric immunogen can be labeled with, for example, a fluorescent marker, and the chimeric immunogen exposed to the cell. The cells can then be washed and treated to liberate the cellular contents. The cytosolic fraction of this preparation can then be isolated and assayed for the presence of the label. Detecting the label in this fraction indicates that the chimeric immunogen has entered the cytosol.

In another method, the ability of the translocation domain and ER retention domain to effect translocation to the cytosol can be tested with a construct containing a domain III having ADP ribosylation activity. Briefly, cells expressing a receptor to which the construct binds are seeded in tissue culture plates and exposed to the chimeric protein or to an engineered PE exotoxin containing the modified translocation domain or ER retention sequence in place of the native domains. ADP ribosylation activity can be determined as a function of inhibition of protein synthesis by, e.g., monitoring the incorporation of 3H-leucine.

5.8.2.4. Immunogenicity

The ability of the chimeric immunogens to elicit an immune response against the heterologous antigen can be assessed by determining the chimeric immunogen's immunogenicity. Both humoral and cell-mediated immunogenicity can be assessed. For example, a humoral immune response can tested by inoculating an animal with the chimeric immunogen and detecting the production of antibodies specific for the heterologous immunogen with a suitable immunoassay. Such detection is well within the ordinary skill of those in the art.

In addition, cell-mediated immunogenicity can be tested by immunizing an animal with the chimeric immunogen, isolating cytotoxic T cells from the animal, and detecting their ability to kill cells whose MHC Class I molecules bear peptides sharing amino acid sequences with the heterologous antigen. This assay can also be used to test the activity of the cell recognition domain, the translocation domain and the ER retention domain because generation of a cell mediated response requires binding of the chimera to the cell, trafficking to the ER, and translocation to the cytosol.

6. EXAMPLES

The following examples merely illustrate the invention, and are not intended to limit the invention in any way.

6.1. Construction of a Chimeric Immunogen Expression Vector

A chimeric immunogen expression vector, ntPEpilinPAK was generated in a multistep process. A 78-bp DNA oligonucleotide duplex encoding the desired 24 amino acids of the PAK strain pilin protein of *Ps. aeruginosa* was digested with SpeI and ApaI and gel purified (QIAGEN™ Inc., Valencia, Calif.). A DNA fragment of PE encoding amino acids 1-360 was generated by PCR using pPE64pSTA553 as a template. See Hertle et al., 2001, *Infect. Immun.* 69(15): 6962-6969. The PCR fragment was digested with HindIII and SpeI and gel purified (QIAGEN™ Inc., Valencia, Calif.). The two purified fragments, the pilin oligoduplex and PCR-fragment, were ligated into the HindIII-ApaI site of pPE64pSTA553. Incorporation of this DNA resulted in the destruction of the PstI restriction site and introduction of a unique SpeI site. The final construct, termed pPilinovax-A, and its correct orientation of the insert were verified by restriction enzyme digestion.

In addition, a toxic form of this chimera, PEpilinPAK, was constructed by ligating the pilin oligonucleotide duplex and PCR fragment in to the HindIII-ApaI site of pPE64-PstI, and was verified by restriction enzyme digestion.

6.2. Expression of a Chimeric Immunogen

*E. coli* DH5α cells (Gibco/BRL) were transformed using a standard heat-shock method in the presence of the appropriate plasmid to generate ntPEpilinPAK, PEpilinPAK or native *Ps. aeruginosa* exotoxin A (PE). Transformed cells, selected on antibiotic-containing media, were isolated and grown in Luria-Bertani broth (Difco; Becton Dickinson, Franklin Lakes, N.J.) with antibiotic and induced for protein expression by the addition of 1 mM isopropyl-D-thiogalactopyranoside (IPTG). Two hours following IPTG induction, cells were harvested by centrifugation at 5000 rpm. Inclusion bodies were isolated following cell lysis and proteins were solubilized in 6M guanidine HCl and 2 mM EDTA (pH 8.0) plus 65 mM dithioerythreitol. Following refolding and purification, as previously described (Buchner et al., 1992, *Anal. Biochem.* 205:263-70; Hertle et al., 2001, *Infect. Immun.* 69(15): 6962-6969), proteins were stored in PBS (pH 7.4) lacking $Ca^{2+}$ and $Mg^{2+}$ at −80° C.

6.3. Expression and Purification of *Pseudmonas* Pilin Protein

Pilin protein was isolated from PAK strain *Ps. aeruginosa* grown overnight in Luria-Bertani broth (DIFCO™) at 37° C. at 75 rpm in a rotary shaker to an optical density at 600 nm (OD600) of 0.6. Bacteria were pelleted at 6,000 rpm for 10 min at room temperature, resuspended in PBS and vortexed aggressively 6 times for 15 sec with 10 sec rests. Bacteria were pelleted at 12,000×g for 10 min and the supernatant containing sheared pili was overnight against 10 mM sodium acetate (pH 4.5) and isolated using SP ion exchange column (HITRAP™ SP HP; Amersham Biosciences, USA) and eluted with 200 mM NaCl.

6.4. Characterization of a Chimeric Immunogen

The chimeric immunogen ntPEpilinPAK was prepared by genetically grafting the terminal 24 amino acids of the *Ps. aeruginosa* PAK strain pilin protein in place of 20 amino acids normally present in ntPE (FIG. 1) as described above. Purified proteins used in these studies were assessed by size-exclusion chromatography using a ZORBAX® GF-450 column (Agilent Technologies, Palo Alto, Calif.) and demonstrated to be greater than 95% monomeric. Purified ntPEpilinPAK, isolated from inclusion bodies and renatured in a redox shuffling buffer protocol as described above, had the anticipated molecular weight of ~68 kDa, similar to that observed for similarly purified and refolded ntPE (FIG. 2A). Additionally, isolated ntPEpilinPAK used in the experiments described herein was determined to have the anticipated mass and composition using amino acid analysis and SDS-PAGE, an isoelectric point of ~5.1, the correct N-terminal sequence, 6.5 ng host cell protein/mg ntPEpilinPAK, <2 pg host cell DNA/mg ntPEpilinPAK, and ~6.3 EU endotoxin/mg ntPEpilinPAK. A monoclonal antibody that recognized the C-terminal loop of PAK pilin also recognized ntPEpilin PAK (FIG. 2B) suggesting a near-native conformational form of the inserted C-terminal pilin loop.

Figure 3:
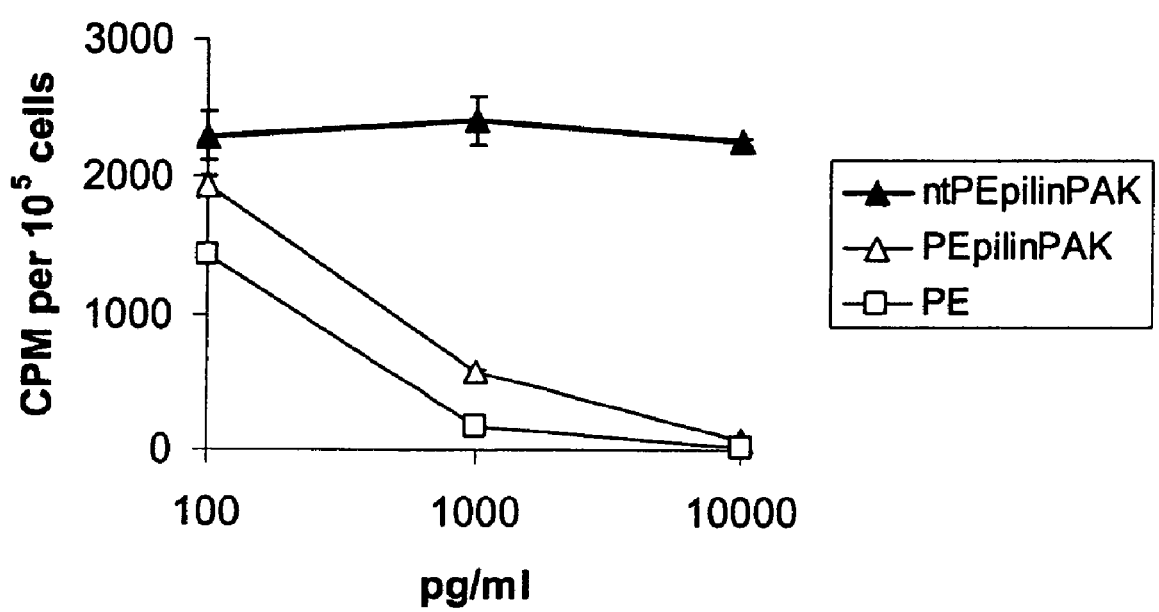
Figure 6:
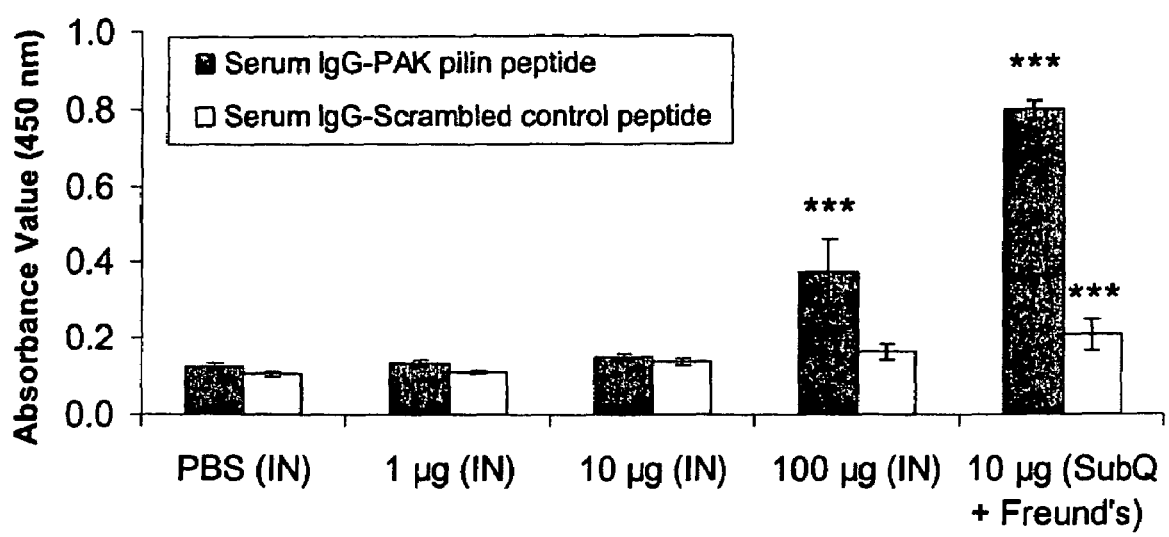

Cytotoxicity due to inhibition of protein synthesis was examined by exposing L929 (ATCC CCL-1) cells to PE as described previously. See Ogata et al., 1990, *J. Biol. Chem.* 265:20678-85. Incubation of PE-sensitive L929 cells with either PE or PEpilinPAK produced similar toxicity profiles (FIG. 3), suggesting that modifications made in the ntPE framework to accommodate pilin PAK sequence elements did not produce untoward perturbation of native toxin structure and function related to cellular uptake and intracellular processing. This assay was also used to demonstrate a complete lack of cytotoxicity by ntPEpilinPAK (FIG. 3).

6.5. Vaccination Using a Chimeric Immunogen

Eight/group BALB/c mice (Charles River Laboratories, Wilmington, Mass.), 6-8 weeks at initial dosing, were used in these studies since age-related suppression of immune function has been demonstrated in this species. See Linton & Dorshkind, 2004, *Nat. Immunol.* 5:133-9. Intranasal inoculation was performed to mice lightly anesthetized with isoflurane. All intranasal (IN) administrations were performed under mild anesthesia since fluid introduced into the nares of awake mice that is in excess of its cavity volume is rapidly ingested while suppression of this reflex occurs under anesthesia. Thus, administration to anesthetized mice results in preferential delivery to the trachea rather than the esophagus following IN administration. See Janakova et al., 2002, *Infect. Immun.* 70:5479-84. Mice received 10 μl of ntPE-pilin (5 μl/nares) in PBS for each immunization. Variations in concentration from 100 μg/ml to 10 mg/ml were prepared for dosing studies to assess immune responses over the range of 1 to 100 μg of ntPE-pilin.

Mice receiving an IN inoculation dose schedule of 0, 7, 14, and 28 days with 1, 10 or 100 μg ntPEpilinPAK were evaluated for mucosal and systemic humoral immune responses, with similar IN delivery of PBS to mice serving as a negative control. Animals receiving a subcutaneous (SubQ) injection of 10 μg ntPEpilinPAK in a standard protocol using Freund's complete/incomplete adjuvant materials served as a positive control.

IN administration of ntPEpilinPAK resulted in anti-vaccine serum IgG responses at the lowest dose examined of 1 μg (FIG. 5). Serum IgG responses achieved with 100 μg IN were comparable to that obtained by subQ injection of 10 μg vaccine with a Freund's adjuvant cocktail. Although in this particular study the 10 μg group was not consistent with a dose-dependent immune response, a dose-dependent response was typically observed. Assessment of anti-vaccine IgG antibodies present in saliva samples demonstrated detectable levels only in the 100 μg IN and 10 μg/Freund's subQ groups. These results suggest that IN administration of ntPEpilinPAK can generate a potent anti-vaccine systemic immune response that compare closely to those observed using a subQ injection protocol involving a regime of complete/incomplete Freund's adjuvant. Thus, IN dosing of ntPEpilinPAK stimulated both mucosal (as demonstrated by antigen-specific salivary IgA antibodies) and systemic immunity (as demonstrated by antigen-specific serum IgG antibodies) in a dose-dependent fashion and potent induction of immune outcomes was achieved in mice with IN doses in the range of 10-100 μg.

Efforts to measure anti-vaccine IgA antibodies in saliva were compromised by the lack of an antibody that selectively recognized mouse secretory IgA (sIgA) rather than serum IgA (FIG. 6). Using the secondary antibody determined to have the greatest capacity to cross-react with sIgA, salivary IgA antibodies specific for ntPEpilinPAK could be observed only in the 100 μg IN dosed mouse group. No similar responses could be detected in either the 1 or 10 μg IN dose groups or in the 10 μg subQ group administered with Freund's adjuvant. Assessment of anti-vaccine IgA antibodies in serum similarly showed that only the 100 μg IN dose group generated detectable antibodies with these characteristics. A detailed study of immune responses to *Chlamydia pneumoniae* demonstrated that active infection resulted in approximately 40-fold less pathogen-specific serum IgA antibodies than serum IgG antibodies. See Wald et al., 2000, *BMJ* 321: 204-7. Although the ELISA assays used in our studies can not be directly compared, mucosal immunization with 100 μg ntPEpilinPAK produced a similar relationship of observed serum IgG and serum IgA responses.

Mucosal immunization with ntPEpilinPAK is believed to provide immunity against both exotoxin A and the terminal pilin loop domain of *Ps. aeruginosa*. Immune responses to ntPEpilinPAK chimera should be dominated by antigenic epitopes present on ntPE relative to the engrafted 24 amino acid domain from pilin. However, much of the potential effectiveness of this vaccine approach relates to blocking pilin-mediated bacteria-host cell interactions that could occur at epithelial surfaces of the oral-pharyngeal cavity and trachea. While the dominant IgA isotype in saliva was assumed to represent sIgA resulting from active transport of dimeric IgA following interaction with the poly Ig receptor, IgG present in the saliva is presumed to exude from the serum. See Song et al., 1994, *Proc. Natl. Acad. Sci. U.S.A.* 91:163-6 and Forrest et al., 1991, *Infect. Immun.* 59:1206-9. Pilin-specific serum IgG responses were detectable in both 100 μg IN and 10 μg subQ/Freund's adjuvant groups, although the immune response generated by injection also demonstrated a non-specific immune response as demonstrated by increased recognition of a control (scrambled) peptide used for this assay (FIG. 6).

The level of insert-specific systemic immunity demonstrated in these studies was comparable to that previously observed using an ntPE-based mucosal vaccine that incorporated the V3 loop of HIV gp120 protein. See Mrsny et al., 1999, *Vaccine* 17:1425-33. Additionally, anti-vaccine salivary IgA response was significantly increased after three exposures but was not dramatically increased by a fourth IN exposure, while increased serum IgG responses recognizing synthetic PAK pilin peptide increased from the third to the fourth IN dose. These results suggest that specific mucosal and systemic immune responses can be achieved with ntPEpilinPAK after only a few (e.g., one, two, three or four) IN exposures.

6.6. Isolation of Secreted Antibodies

Mouse saliva (typically 50-100 μl) was collected over a 10 min period using a polypropylene Pasteur pipette following the induction of hyper-salivation by an intra-peritoneal injection of 0.1 mg pilocarpine per animal. Serum samples (100 μl) were obtained using serum separators with blood collected from periorbital bleeds. Serum and saliva samples were then aliquoted in 10 μl volumes and stored at −70° C. until analysis. Secreted antibodies thus obtained were characterized in the assays described below.

6.7. ELISA Assays

Antibodies against ntPEpilinPAK vaccine candidate were measured by enzyme-linked immunosorbent assay (ELISA). Costar 9018 E.I.A./R.I.A. 96-well plates were coated overnight with 0.6 μg/well of ntPEpilinPAK in 0.2M $NaHCO_3$—$Na_2CO_3$, pH 9.4. Each 96-well plate was washed four times with PBS containing 0.05% Tween 20-0.01% thimerosal (wash buffer); and then blocked for 1 h with PBS/Tween 20 containing 0.5% BSA-0.01% thimerosal (assay buffer). Serum and saliva samples were diluted with assay buffer, loaded onto a 96-well plate, and incubated for 2 h for serum IgG and overnight for saliva and serum IgA. Each 96-well plate was then washed four times with wash buffer, and horseradish peroxidase ("HRP") conjugated goat anti-mouse serum IgG (Pierce Chemical Company, Rockford, Ill.) or serum IgA (Kirkegaard & Perry Laboratories, Gaithersburg, Md.) was added, then the plates were incubated for 1 and 4 h, respectively. All incubation and coating steps were performed at room temperature covered with parafilm on a shaker at 4 rpm for the specified times. TMB (3,3',5,5'tetramethylbenzidine), substrate for HRP, was used to quantify bound antibody at 450 nm.

Specific immune responses against biotinylated pilin PAK peptide were assessed by coating each plate overnight with 1 μg/well of streptavidin. Pilin PAK peptide (Biotin-KCTSDQDEQFIPKGCSK-$NH_2$; SEQ ID NO:7) and scrambled control peptide (Biotin-KCDDFKQGTQEPISCSK-$NH_2$; SEQ ID NO:12) were manufactured at SYNPEP™ (Dublin, Calif.). Each plate was then blocked with assay buffer for 1 h, and 1 μg/well of pilin PAK and scrambled control peptides were added and incubated for 1 h. The remainder of the ELISA procedure was performed as described immediately above.

6.8. *Pseudomonas* Attachment Assays

PAK strain *Pseudomonas aeruginosa* (ATCC 53308) used for adherence and detachment studies was carefully cultured to late log phase to retain pili on *bacterium*. Briefly, PAK was grown overnight in Luria Bertani broth (DIFCO™; Becton Dickinson, Franklin Lakes, N.J.) at 37° C., 75 rpm rotary shaking to an optical density at 600 nm (OD600) of 0.6, approximately 1×109 colony forming units (Cfu) per ml. Bacteria was collected via microfuge centrifugation at 6000 rpm for 10 min at room temperature and resuspended in antibiotic-free Ham's F-12 media.

PAK was opsonized for 30 min at room temperature with rotary shaking before adding to confluent layers of A549 cells at a multiplicity of infection of 50. IN-immunized sera samples were diluted to 1:100 or to various dose-dependent dilutions to assess prophylactic abilities. Final volumes in each well were 200 μl following addition of bacteria and all reagents.

A549 (human lung epithelial-like carcinoma cells; ATCC CCL-185) cells were maintained in Ham's F-12 medium (Ham's F12) supplemented with 10% heat-inactivated fetal bovine serum (HI-FBS), 2.5 mM glutamine, 100 U/ml penicillin, and 100 μg/ml streptomycin in 5% $CO_2$ at 37° C. Cells were transferred to antibiotic-free Ham's F-12 medium to seed in chamber slides or electrode arrays for assays.

*Ps. aeruginosa* adherence to A549 cells was quantified as follows. A549 cells were grown in LAB-TEK™ II 8-chamber slides (LAB-TEK™ Plastics Co., Westmont, Ill. USA) in antibiotic-free medium to a density of approximately $1\times10^5$ cells per chamber using culture conditions described in Ogata et al., 1990, *J. Biol. Chem.* 265:20678-85. Spent media was removed before adding bacteria opsonized with test samples. Chamber slides were incubated for 2 h at 37° C. and 5% $CO_2$.

Cells were gently washed three times with Hanks' balanced salt solution to remove unbound bacteria, fixed for 1 h in 3.7% paraformaldehyde in phosphate buffered saline (PBS), pH 7.2, washed twice with saline and stained with 10% Giemsa stain for 10 min. After washing to remove excess Giemsa stain, adherent bacteria were determined by counting cell-associated bacteria per 50 A549 cells under light microscopy at 1000× magnification. All samples were tested in duplicate.

In addition, quantitative real-time PCR was used to detect and quantitate the presence of PAK bacteria adhering to A549 cells. Supernatants were spun @ 5000×g for 5 min and aspirated. The bacterial pellet was saved @ −70° C. until further processing. Real-time detection of PCR was performed using the APPLIED BIOSYSTEMS™ 7300 Real Time PCR system (APPLIED BIOSYSTEMS™, Foster City, Calif.). The differential displays of mRNAs for PAK pilin was determined. Total RNA from bacteria was isolated according to the RNeasy™ Protect Mini Kit (QIAGEN™). Total RNA was used to generate cDNA for oligo dT oligodeoxynucleotide primer (T12-18) following the protocol for OMNISCRIPT™ Reverse Transcriptase (QIAGEN™). The following primers were designed using PRIMER EXPRESS™ software (APPLIED BIOSYSTEMS™) and synthesized by OPERON™ (Alameda, Calif.): PAK pilin (forward): AGGTACAGAGGACGCTACTAAGAAAGA (SEQ ID NO.:10); PAK pilin (reverse): TCAGCAGGATCGGGTTTGA (SEQ ID NO:11). Equal amounts of cDNA were used in duplicates and amplified with the SYBR™ Green I Master Mix (APPLIED BIOSYSTEMS™). The thermal cycling parameters were as follows: thermal activation for 10 min at 95° C., and 40 cycles of PCR (melting for 15 s at 95° C. and annealing/extension for 1 min at 60° C.). A standard curve was constructed with a dilution curve (1:5, 1:10, 1:20, 1:40, 1:80, 1:160, 1:320, 1:640) of total RNA from PAK for PAK pilin. A "no template control" was included with each PCR.

Cell-substrate detachment was measured using a non-invasive electric cell-substrate impedance sensing (ECIS) method. See Wegener et al., 2000, *Exp. Cell. Res.* 259:158-66. A549s were seeded onto 8-well one electrode culture arrays (8W1E) (Applied Biophysics, Troy, N.Y.), with a working electrode area of $5\times10^{-4}$ cm$^2$ and a counter electrode area of 0.15 cm$^2$, in a humidified incubator at 37° C. in 5% $CO_2$.

Cell attachment was monitored for 22 h to ensure confluent lawns of approximately $1\times10^5$ cells/well with a resistance reading of 2-3 kOhms. Cells were further stabilized by replenishing with fresh media for 2-3 h prior to introduction of bacteria preparations and initiation of detachment monitored at 0.5 min timepoints, 40 kHz. Detachment assays were followed for 24 h and values normalized to electrode check values at the start of the experiment to 1.0.

Using these protocols, interaction of PAK strain *Ps. aeruginosa* with A549 cell lawns through pilin-specific contacts was assessed using increasing amounts of ntPEpilinPAK and a monoclonal antibody (ID10) that recognizes the C-terminal pilin loop as a control. Such increasing amounts of ntPEpilinPAK were able to reduce the interaction of PAK strain *Ps. aeruginosa* with A549 cells in this in vitro assay (FIG. 7A). Since this interaction was not significantly disrupted by ntPE (lacking the pilin loop insert), this assay described a pilin-dependent interaction between PAK strain *Ps. aeruginosa* and A549 cells.

Saliva samples collected from ntPEpilinPAK-immunized mice and diluted 1:100 in PBS were able to significantly decrease the number of PAK strain *Ps. aeruginosa* that attached to A549 cell lawns in vitro (FIG. 7B) and these data correlated with monoclonal antibody-mediated disruption of these interactions. Inhibition of binding exhibited a dose-dependency not only based upon the amount of ntPEpilinPAK used for IN vaccination but also for dilution of saliva samples obtained from IN immunized mice as evidenced by the amount of bacteria not adhering to A549 cell lawns (FIG. 7C). Importantly, a 1:100 dilution with PBS of saliva from mice in the 10 µg subQ group administered with Freund's adjuvant also blocked A549-*Ps. aeruginosa* interactions. Based upon measured anti-vaccine and anti-pilin loop responses, it is believed that a sIgA response was primarily responsible for protection elicited by the IN dosed mice although this could not be verified due to insufficient sIgA ELISA sensitivity. Similarly, while IgG exudates from serum into saliva may have provided protective actions for the subQ/Freund's adjuvant group, it is believed that sIgA in saliva from these animals also participated in these observed outcomes.

Also, an in vitro system that relies upon the tendency of A549 to cells round up and lift from their substrate following several hours of contact with a piliated PAK strain of *Ps. aeruginosa* was used to assess the ability of saliva-samples from IN immunized mice to prevent *Ps. aeruginosa* adherence to A549 cells. In order to monitor this event we employed electric cell-substrate impedance sensing (ECIS). This technique uses an electrode array to continuously monitor cell-substrate interactions as described in Wegener et al., 2000, *Exp. Cell. Res.* 259:158-66. Increasing amounts of *Ps. aeruginosa* PAK strain, from 20-200 bacteria per A549 cell, demonstrated accelerated rates of cell lifting as demonstrated by ECIS and corroborated by microscopic assessment. Four hours following inoculation with 50 bacteria per A549 cell there was extensive rounding of A549 cells and loss of epithelial cell-substrate association characterized by reduction of resistive properties of the system (FIG. 8). Simultaneous introduction of saliva samples (diluted 1:100 with PBS) obtained from ntPEpilinPAK-immunized mice blocked this *Ps. aeruginosa*-induced A549 cell rounding and lifting event (FIG. 8). Although the exact mechanism(s) involved in the lifting response observed in A549 cells remains obscure, such a morphological outcome is generally associated with cytotoxic events and results obtained with saliva from immunized mice suggests that disruption of pilin-mediated interactions can reduce this detrimental event.

6.9. Exotoxin A Neutralization Assays

The ability of the secreted and serum antibodies induced as described above to neutralize the protein synthesis inhibitory activity of *Pseudomonas* exotoxin A was tested according to the following protocol. A549 cells were grown in Dulbecco's modified Eagle's medium F12 (DMEM F12) supplemented with 10% HI-FBS, 2.5 mM glutamine, 100 U/ml penicillin, and 100 µg/ml streptomycin in 5% CO2 at 37° C. Cell toxicity assays using A549 cells were performed essentially as previously performed using L929 cells. Apoptosis was assessed by measuring caspase-3 activity according to manufacturer's instructions. (APOALERT™ Caspase-3 Colorimetric Assay Kit, BD™, Frankin Lakes, N.J.).

Expression of some *Ps. aeruginosa* virulence factors might be induced following pili-mediated adherence as is seen with uropathogenic *E. coli*. See, e.g., Zhang & Normark, 1996, *Science* 273:1234-6. PE secreted from *Ps. aeruginosa*, considered one of the most potent virulence factors secreted by *Ps. aeruginosa* infection, can be highly cytotoxic. See Fogle et al., 2002, *J. Surg. Res.* 106:86-98. PAK strain-induced A549 cell lifting, as described above, did not appear to involve actions of this enzyme since no PE was ever detected in any incubation, consistent with an observation that PE is secreted by *Ps. aeruginosa* under times of iron-deficient stress and culture media used in A549 lifting assays was not iron-deficient. See Sokol et al., 1982, *J. Bacteriol.* 151:783-7. PE, however, still represents a potent virulence factor for *Ps. aeruginosa* infection and previous studies, where ntPEpilinPAK vaccine with an abbreviated pilin sequence was injected into rabbits, demonstrated serum immune responses capable of neutralizing the toxicity of PE in vitro. See Hertle et al., 2001, *Infect. Immun.* 69:6962-6969.

A549 cells challenged with PE had increased caspase-3 expression after 24 hr in vitro (FIG. 9), indicating induction of apoptosis—the mechanism by which PE kill cells. See Morimoto & Bonavida, 1992, *J. Immunol.* 149:2089-94. Introduction of saliva from IN immunized mice neutralized the toxicity of PE in vitro (FIG. 9). Interestingly, saliva from mice immunized with 10 µg subQ group administered with Freund's adjuvant failed to neutralize under the same conditions, which could be due, for example, to variations in antibody isotypes or affinities.

6.10. Comparison of Immune Response Induced by Chimeric Immunogens Comprising Short and Long Pilin Peptides The ELISA assay described in Section 6.7, above, was used to assess the immune responses induced by chimeric immunogens comprising residues 128-144 (the "short" pilin peptide; KCTSDQDEQFIPKGCSK; SEQ ID NO.:7) or residues 121-144 (the "long" pilin peptide, TAADGLWKCTSDQDEQFIPKGCSK SEQ ID NO.1) of *Ps. aeruginosa* PAK pilin protein. Briefly, 100 µg chimeric immunogen comprising the short or the long peptide were administered IN in phosphate buffered saline (PBS) or PBS plus 0.05% carboxymethyl cellulose (CMC). PBS or PBS plus 0.05% CMC were administered IN as negative controls, while 10 µg chimeric immunogen comprising the long peptide with 0.05% CMC and Freund's complete/incomplete adjuvant cocktail was administered subcutaneously as a positive control. Both salivary IgA and serum IgG immune responses were assessed.

FIG. 10 demonstrates that a chimeric immunogen comprising the long pilin peptide was surprisingly more effective than a chimeric immunogen comprising the short pilin peptide at inducing a salivary IgA response specific for ntPEpilinPAK. Specifically, mice in groups C and D, administered a chimeric immunogen comprising the long pilin peptide, secreted more IgA specific for ntPEpilinPAK into saliva than mice administered a chimeric immunogen comprising the short pilin peptide. Similarly, FIG. 11 demonstrates that chimeric immunogen comprising the long pilin peptide also more effectively induced a serum IgG response specific for ntPEpilinPAK than the chimeric immunogen comprising the short pilin peptide. Taken together, these results demonstrate that chimeric immunogens comprising the long pilin peptide more effectively induce immune responses against ntPEpilinPAK than chimeric immunogens comprising the short pilin peptide.

6.11. Clinical Evaluation of ntPEpilinPAK

This example describes clinical evaluation of the safety and immunogenicity of ntPEpilinPAK in a Phase I, randomized, double-blind, placebo-controlled, dose-escalation study in healthy adult subjects. In the trial, each volunteer receives three intranasal administrations of ntPEpilinPAK at a single dose level with 28 days between immunizations.

In this human study, ntPEpilinPAK is evaluated according to three criteria: safety and tolerability of the three escalating doses of immunogen; absorption of the immunogen as determined by serum concentration of ntPEpilinPAK from a pharmacokinetic assessment (following the first vaccination in each dose cohort); and the immune response to ntPEpilinPAK prior to dosing and at various times after administration. In regard to measuring immunogenicity, serum, saliva and nasal wash samples obtained from healthy subjects are analyzed for antibodies against the C-terminal pilin loop and against PE. All immunological assessments will be performed using a standard ELISA assay 6.11.1. Study Design and Cohort Selection Three sequential cohorts of 12 subjects each are enrolled, for a total of 36 subjects. Randomization within each cohort of 12 subjects assures that nine individuals receive ntPEpilinPAK and three individuals receive a placebo that is indistinguishable from the chimeric immunogen. Each subject receives three intranasal immunizations of ntPEpilinPAK or control at one of three dose levels, beginning with the lowest dose cohort. The three study immunizations are administered at 28 day intervals on Days 0, 28, and 56.

Subjects for this study are healthy adults, aged 18 to 45 years. Subjects are evaluated prior to administration of ntPEpilinPAK to assure that they are in good general health, free from significant illness or disease as indicated by history, physical examination (PE), and laboratory tests. In particular, subjects undergo a medical history, physical examination, and laboratory evaluation (urinalysis, clinical chemistry and hematology). Blood is obtained for assessment of serologic status for HBV, HCV, and HIV and immune responses directed against *P. aeruginosa*. An oropharyngeal (OP) culture is obtained for *P. aeruginosa*. Serum, saliva and nasal secretions are collected for assessment of the presence of antibodies directed against *P. aeruginosa* antigens.

6.11.2. Clinical Administration of a Chimeric Immunogen

Either ntPEpilinPAK or placebo formulated in Phosphate Buffered Saline (PBS) is administered to the subject. Subjects are administered 40, 200 or 1000 µg/administration for the Low, Intermediate and High Dose cohorts, respectively. The study dose of 0.2 ml administered to each subject is delivered as a spray, and administered as two doses of 0.1 ml in each nostril using a single BD™ ACCUSPRAY™ device (BD™ Medical-Pharmaceutical Systems, Franklin Lakes, N.J.).

Four subjects from each dose cohort receive the first administration of study product in a blinded manner on the same day. Provided there are no clinically significant adverse events in this initial cohort, the remaining eight subjects from the same dose cohort receive the first administration at least 7 days after the initial cohort has received their first dose.

Subjects remain in the clinical research unit for at least 6 hours following immunization during which time frequent vital signs will be obtained and subjects are questioned regarding local symptoms (e.g., nasal pain, nasal congestion, nasal irritation, rhinorrhea, bloody or blood-tinged nasal secretions, sinus pain, ear pain and sore throat) and systemic symptoms (e.g., fever, chills, shortness of breath, wheezing, cough, malaise, headache, nausea, myalgia, arthralgia, and rash). Interim cranial nerve exam (including olfactory exam) is performed prior to discharge from the study site. A diary card is dispensed and instructions given on its daily completion through Day 7 following administration.

Provided there are no clinically significant adverse events in this initial cohort, the remaining eight subjects are scheduled for attendance no less than 7 days later and within 14 days of their screening visit. These subjects will undergo the same assessment and dosing procedures as for the first four subjects in the initial Low Dose cohort.

All subjects in each dose cohort have blood drawn immediately prior to vaccination (0 minutes) and at 10, 20, 30, 45, 90 minutes and 2, 4 and 6 hours following administration of the first vaccination to measure serum concentration of ntPEpilinPAK. Samples are processed (see Section 6.11.4: Determination of Pharmacokinetics and Immunogen Absorption Profile, below.), stored at −70° C. on site and shipped on dry ice for analysis. Serum, saliva and nasal wash samples for immunogenicity testing are obtained at baseline and processed on site (see Section 6.11.5: Sample Collection, below.), stored at −70° C. until shipped on dry ice to for immunogenicity analysis. In addition, blood samples for hematology and chemistry laboratories, and urine for urinalysis are obtained at baseline (as well as Days 2, 14 and 28) and analyzed on site.

Interim outpatient visits occur on Days 2, 7, 14 and 28 after immunization for evaluation of local and systemic adverse events and/or immune response to the intranasal immunization (see Schedule of Study Procedures). Samples for immunogenicity analysis will be collected, processed and shipped as described above and below.

The Low Dose cohort return on Day 28+/−2 days, at which time they are evaluated for adverse events, health status and continued study eligibility. If the first administration does not result in immunogen-associated clinically significant adverse events, then subjects in the Low Dose cohort receive their second intranasal administration with the same dose level as that received at their first administration (placebo or Low Dose of the chimeric immunogen). Subjects remain in the clinical research unit for at least 2 hours following immunization and have interim follow-up visits on Days 30, 35, 42 and 56 for evaluation of local and systemic reactions and/or immune response.

Subjects in the Low Dose cohort then return on Day 56, at which time they are evaluated for adverse events, health status and continued study eligibility. If there are no clinically significant safety concerns, they receive their third intranasal administration with the same dose level as administered at the first two administrations (placebo or Low Dose of chimeric immunogen). Subjects remain in the clinical research unit for at least 2 hours following immunization and have interim follow-up visits on Days 58, 63, 70, and 84 for evaluation of local and systemic reactions and/or immune response.

A final telephone follow-up occurs at Day 180 (Days 168-195) for the Low Dose cohort and subjects are queried regarding persistent symptoms since Day 84 (Visit 14), hospitalizations, new diagnoses or major medical problems.

Enrollment of the Intermediate Dose cohort proceeds once the Low Dose cohort has completed the Day 14 visit. Safety data (adverse events, use of concomitant medications and results of safety laboratory testing) obtained during the first two weeks after the first intranasal administration in the Low Dose cohort are evaluated in a blinded manner by the principal investigator and medical monitor. If the Low Dose cohort is without clinically significant safety concerns, then the first four subjects in the Intermediate Dose cohort will be admitted to the study center and undergo the same admission process and study product administration as for the Low Dose cohort. Subjects in the Intermediate Dose cohort are randomized to receive either placebo or the Intermediate Dose of ntPEpilinPAK. Provided there are no clinically significant adverse events for this initial cohort, the remaining eight subjects are scheduled for attendance no less than 7 days later and within 14 days of their screening. These subjects undergo the same assessment and dosing procedures as the first four subjects in the initial Intermediate Dose cohort.

Safety evaluation of the Intermediate Dose cohort through the first two weeks after first administration occurs in a manner identical to the Low Dose cohort, with subsequent admission and administration of the High Dose cohort so long as there are no clinically significant safety concerns in the Intermediate Dose cohort. Individuals randomized to receive ntPEpilinPAK in the High Dose cohort receive the highest study dose of ntPEpilinPAK.

The evaluation of safety data following the second and third intranasal immunizations are performed in a manner identical to that of the first immunization. The second and third immunizations for the Intermediate and High Dose cohorts proceed only if there are no clinically significant safety concerns identified during the first two weeks after the second and third administrations of the preceding cohort.

6.11.3. Safety Evaluation

All safety data from Days 0-14, including adverse events and laboratory safety parameters, are reviewed prior to enrolling the next dose cohort. The following events result in a temporary halt to dose escalation to determine whether the protocol should proceed, be modified, or be terminated 1). Any serious adverse event (SAE) possibly related to the Study Product (without a clear alternative etiology); and (2) Any severe adverse event (including laboratory parameters), as defined in the draft FDA guidance entitled "Grading Scales for Monitored Clinical Parameters: Guidelines for Vaccine Clinical Trials Enrolling Healthy Adults, age 18-40 years" (August 2003).

6.11.4. Determination of Pharmacokinetics and Immunogen Absorption Profile.

Subjects in each dose cohort provide blood samples following the first administration for the analysis of ntPEpilinPAK absorption from the nasal mucosa into the systemic circulation. Blood is collected from a venous catheter from either forearm prior to administration, (0 minutes), and at 10, 20, 30, 45, 90 minutes and 2, 4 and 6 hours after the first administration only (for each of the three dose levels). An approximate volume of 4-6 ml of blood is collected to give a minimum serum volume of 2-3 ml at each of these time points.

The samples are processed by first collecting blood into standard serum collecting tubes, allowing clotting for 30-60 minutes at room temperature and then centrifuging at 4° C. to separate the serum. A minimum of 2-3 ml of serum is transferred (split) into 1-1.5 ml aliquots each into two duplicate polypropylene tubes, snap frozen and stored at −70° C. in a freezer with a temperature recording device until shipped on dry ice in batch shipments (of the first for each duplicate sample) for analysis. There are three batch shipments, each corresponding to the completion of the first administration for all subjects in each of the dose cohorts. This will be followed by the final shipment of the remaining duplicate samples for all subjects.

Standard pharmacokinetic analysis of the audited tabulated data is analyzed by determining standard pharmacokinetic parameters (e.g., half life, Cmax, etc.).

6.11.5. Sample Collection and Processing

Sample collection for the immune assays and the *P. aeruginosa* culture takes place prior to the first administration and 14 and 28 days after each study product administration, i.e. on Days 14, 28, 42, 56, 70 and 84. Samples are collected in the following order: (1) Nasal wash; (2) Saliva; and (3) Blood.

6.11.5.1. Nasal Wash Collection

The first 5.0 ml of a 10 ml sterile lactated ringers or normal saline solution, supplied by the study site, is aspirated into a sterile bulb syringe and the volunteer is asked to hold their breath while the solution is gently sprayed into the nostril of the volunteer (to avoid swallowing). The tip of the syringe is inserted about 1 cm into the nostril. A sterile 12 cc syringe with a sterile rubber tip may be substituted for the bulb syringe. The subject then blows the nasal fluid into a plastic cup without swallowing. The remaining 5.0 ml of sterile saline solution is then sprayed into the nostril that has not previously been washed and the sample collected into the same collection container. Thus, the samples from each nostril are collected in a single container. The sample is then transferred as equal aliquots (~1.5 ml) into two 15 ml conical tubes each containing 50 µl of protease inhibitor. The sample is then processed as described below in Section 6.5.11.5: "Processing of Collected Saliva and Nasal Washes."

6.11.5.2. Saliva Collection

Approximately 3 ml of free-running saliva is obtained by having the subject pool saliva in the mouth and then spit into a 50 ml sterile plastic specimen container or collection cup until the minimum volume is obtained. The sample is not an expectorated sample from the throat or lower respiratory tract. This volume of saliva is immediately transferred from the 50 ml sterile plastic specimen container or collection cup into the protease inhibitor containing tube (50 µl of protease inhibitor previously aliquoted into a 15 ml sterile conical tube). The tube is briefly finger-vortexed (mixed or swirled) and placed on ice for processing as described in Section 6.11.5.6: "Processing of Collected Saliva and Nasal Washes," below.

6.11.5.3. Serum Collection

Blood is collected by placing a venous catheter in either arm (or according to normal blood collect practice at the site) and withdrawing a volume of at least 20 ml that would give a minimum of 10 ml of serum after processing. Blood is collected into two or more ~10 ml serum separating tubes routinely used for this purpose. Blood collected is placed on ice and processed within 30 minutes of collection. The sample is processed as described in Section 6.11.5.5: "Processing of Collected Blood samples" as described below.

6.11.5.4. Swabbing Nasopharyngeal Cavity for Culture

Oropharyngeal cultures are obtained by swabbing the posterior oropharyngeal wall and tonsillar pillars with a cotton-tipped swab. The sample collection is documented on the standard site form available for this purpose and the information that the sample was collected and the subsequent results recorded on the appropriate CRF.

6.11.5.5. Processing of Collected Blood Samples

Samples are centrifuged at 5,000×g at 4° C. for 15 min. The supernatant is aspirated and equal volumes transferred to four duplicate labeled cryovials and placed on ice until snap frozen using liquid $N_2$.

6.11.5.6. Processing of Collected Saliva and Nasal Washes

A minimum of 2 ml of saliva and 3 ml of nasal wash is collected. Each sample is centrifuged at 5000 g at 4° C. for 15 minutes to sediment any particulate matter. The supernatant is then aliquoted. From each sample collected, half of the volume collected (i.e., each of ~1 ml for saliva and ~1.5 ml for nasal wash) is aliquoted to each of two 5 ml cryovials Once the samples have been split equally into duplicate tubes, they are immediately flash frozen using liquid $N_2$. Flash frozen duplicate samples are stored at in −70° C. freezer with a temperature monitoring chart.

6.11.6. Clinical Criteria for Evaluation

The clinical and laboratory endpoints measured and analyzed for safety and tolerability include: (1) adverse events (AEs) and serious adverse events (SAEs); (2) concomitant medication use; (3) changes over time in renal function as measured by urinalysis, BUN and creatinine (Cr); (4) changes over time in hepatic function as measured by alkaline phosphatase, ALT and AST; (5) changes over time in hematology parameters including red blood cell (RBC) counts, white blood cell (WBC) counts with differential, and platelets; (6) changes over time in clinical chemistries (electrolytes, glucose etc.); and (7) changes in vital signs (blood pressure (BP) and heart rate (HR)).

The laboratory endpoints to be measured and analyzed for assessment of *P. aeruginosa* status and immunogenicity of include: (1) serum concentration of ntPEpilinPAK over a 6 hour period following administration; (2) immune response as measured by anti-pilin and anti-exotoxin A serum IgG and IgA and anti-pilin and anti-exotoxin A mucosal (nasal wash and saliva) IgA and IgG; and (3) culture of nasal secretions for *P. aeruginosa*.

6.11.7. Immunological Assessment of Serum, Saliva and Nasal Wash Samples

To assess the immune responses to ntPEpilinPAK, the following anti-ntPEpilinPAK antibodies are measured by Enzyme-Linked Immunosorbant Assay (ELISA): (1) serum IgG and IgA to the pilin peptide; serum IgG and IgA to the PE; (3) salivary IgA and IgG to the pilin peptide; salivary IgA and IgG to PE; (5) nasal wash IgA and IgG to the pilin peptide; (6) nasal wash IgA and IgG to PE; and (7) total secretory saliva and nasal wash IgA. Representative ELISA protocols for evaluating such antibody responses are extensively described above.

The present invention provides, inter alia, chimeric immunogens and methods of inducing an immune response in a subject. While many specific examples have been provided, the above description is intended to illustrate rather than limit the invention. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. Citation of these documents is not an admission that any particular reference is "prior art" to this invention.

What is claimed is:

1. A chimeric immunogen, comprising
a)—a receptor binding domain,
b)—a translocation domain, and
c)—a *Pseudomonas* pilin peptide consisting of the amino acid sequence that is TAADGLWKCTSDQDEQFIPKGCSK (SEQ ID NO.: 1),
wherein said chimeric immunogen, when administered to a subject, induces an immune response in said subject that is effective to reduce adherence of a *Pseudomonas* bacterium that expresses said *Pseudomonas* pilin peptide to epithelial cells of said subject.

2. The chimeric immunogen of claim 1, wherein said chimeric immunogen, when administered to said subject, generates an immune response in said subject that reduces the cytotoxicity of *Pseudomonas* exotoxin A to the subject.

3. The chimeric immunogen of claim 1, wherein said chimeric immunogen further comprises an endoplasmic reticulum retention domain.

4. The chimeric immunogen of claim 3, wherein said *Pseudomonas* pilin peptide is located between said translocation domain and said endoplasmic reticulum retention domain.

5. The chimeric immunogen of claim 3, wherein said endoplasmic reticulum retention domain is an enzymatically inactive domain III of *Pseudomonas* exotoxin A.

6. The chimeric immunogen of claim 5, wherein said enzymatically inactive domain III of *Pseudomonas* exotoxin A is inactivated by deleting a glutamate at position 553.

7. The chimeric immunogen of claim 3, wherein said endoplasmic reticulum retention domain comprises an amino acid sequence that is selected from the group of RDEL (SEQ ID NO.:2) or KDEL (SEQ ID NO.:3).

8. The chimeric immunogen of claim 1, wherein said translocation domain is selected from the group consisting translocation domains from *Pseudomonas* exotoxin A, *diptheria* toxin, pertussis toxin, *cholera* toxin, heat-labile *E. coli* enterotoxin, shiga toxin, and shiga-like toxin.

9. The chimeric immunogen of claim 5, wherein said translocation domain is domain II of *Pseudomonas* exotoxin A.

10. The chimeric immunogen of claim 1, wherein said translocation domain comprises amino acids 280 to 364 of domain II of *Pseudomonas* exotoxin A.

11. The chimeric immunogen of claim 1, wherein said chimeric immunogen comprises more than one of said *Pseudomonas* pilin peptides.

12. The chimeric immunogen of claim 1, wherein said receptor binding domain is selected from the group consisting of domain Ia of *Pseudomonas* exotoxin A; a receptor binding domains from *cholera* toxin, *diptheria* toxin, shiga toxin, or shiga-like toxin; a monoclonal antibody, a polyclonal antibody, or a single-chain antibody; TGFα, TGFβ, EGF, PDGF, IGF, or FGF; IL-1, IL-2, IL-3, or IL-6; and MIP-1a, MIP-1b, MCAF, or IL-8.

13. The chimeric immunogen of claim 12, wherein said receptor binding domain is domain Ia of *Pseudomonas* exotoxin A.

14. The chimeric immunogen of claim 13, wherein said domain Ia of *Pseudomonas* exotoxin A has an amino acid sequence that is SEQ ID NO.:4.

15. The chimeric immunogen of claim 1, wherein said receptor binding domain binds to α2-macroglobulin receptor, epidermal growth factor receptor, transferrin receptor, interleukin-2 receptor, interleukin-6 receptor, interleukin-8 receptor, Fc receptor, poly-IgG receptor, asialoglycopolypeptide receptor, CD3, CD4, CD8, chemokine receptor, CD25, CD11B, CD11C, CD80, CD86, TNFα receptor, TOLL receptor, M-CSF receptor, GM-CSF receptor, scavenger receptor, or VEGF receptor.

16. The chimeric immunogen of claim 15, wherein said receptor binding domain binds to α2-macroglobulin receptor.

17. The chimeric immunogen of claim 1, wherein said chimeric immunogen has an amino acid sequence that is SEQ ID NO.:5.

18. A composition comprising a chimeric immunogen, wherein said chimeric immunogen comprises:
a)—a receptor binding domain,
b)—a translocation domain, and
c)—a *Pseudomonas* pilin peptide that has an amino acid sequence that is TAADGLWKCTSDQDEQFIPKGCSK (SEQ ID NO.: 1)
wherein said chimeric immunogen, when administered to a subject, induces an immune response in said subject that is effective to reduce adherence of a *Pseudomonas* bacterium that expresses said *Pseudomonas* pilin peptide to epithelial cells of said subject.

19. The composition of claim 18, wherein said composition further comprises a pharmaceutically acceptable diluent, excipient, vehicle, or carrier.

20. A kit comprising the composition of claim 18, wherein said composition is in a single-unit dosage form.

21. A method for inducing an immune response in a subject, comprising administering to said subject an effective amount of a chimeric immunogen comprising a receptor binding domain, a translocation domain, and a *Pseudomonas* pilin peptide that consists of the amino acid sequence that is TAADGLWKCTSDQDEQFIPKGCSK (SEQ ID NO.: 1), wherein said chimeric immunogen induces an immune response in said subject that is effective to reduce adherence of a microorganism expressing the *Pseudomonas* pilin peptide to epithelial cells of said subject when said chimeric immunogen is administered to said subject.

22. A method for generating in a subject antibodies specific for a *Pseudomonas* pilin peptide consisting of the amino acid sequence that is TAADGLWKCTSDQDEQFIPKGCSK (SEQ ID NO.:1), comprising administering to said subject an effective amount of a chimeric immunogen comprising a receptor binding domain, a translocation domain, and a *Pseudomonas* pilin peptide that consists of the amino acid sequence that is TAADGLWKCTSDQDEQFIPKGCSK (SEQ ID NO.: 1), thereby generating antibodies specific for said *Pseudomonas* pilin peptide.

* * * * *

UNITED STATES PATENT AND TRADEMARK OFFICE
CERTIFICATE OF CORRECTION

PATENT NO. : 7,611,714 B2  Page 1 of 1
APPLICATION NO. : 11/244348
DATED : November 3, 2009
INVENTOR(S) : Mrsny It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 324 days.

Delete the phrase "by 324 days" and insert -- by 719 days --

Signed and Sealed this

Fourth Day of May, 2010

David J. Kappos
*Director of the United States Patent and Trademark Office*